(12) United States Patent
Wang et al.

(10) Patent No.: US 10,799,308 B2
(45) Date of Patent: Oct. 13, 2020

(54) VIRTUAL REALITY SURGICAL TOOLS SYSTEM

(71) Applicant: Vicarious Surgical Inc., Cambridge, MA (US)

(72) Inventors: Daniel Wang, Cambridge, MA (US); Sammy Khalifa, Medford, MA (US); Adam Sachs, Cambridge, MA (US)

(73) Assignee: VICARIOUS SURGICAL INC., Cambridge, MA (US)

( * ) Notice: Subject to any disclaimer, the term of this patent is extended or adjusted under 35 U.S.C. 154(b) by 431 days.

(21) Appl. No.: 15/891,865

(22) Filed: Feb. 8, 2018

(65) Prior Publication Data

US 2018/0221102 A1    Aug. 9, 2018

Related U.S. Application Data

(60) Provisional application No. 62/532,054, filed on Jul. 13, 2017, provisional application No. 62/456,926, filed on Feb. 9, 2017.

(51) Int. Cl.
    *A61B 34/00*    (2016.01)
    *A61B 17/29*    (2006.01)
    (Continued)

(52) U.S. Cl.
    CPC .............. *A61B 34/71* (2016.02); *A61B 17/29* (2013.01); *A61B 34/30* (2016.02);
    (Continued)

(58) Field of Classification Search
    CPC ......... A61B 34/30; A61B 34/70; A61B 17/29; A61B 2017/2931; A61B 2017/2939;
    (Continued)

(56) References Cited

U.S. PATENT DOCUMENTS

| 2,053,868 A | 9/1936 | Grosso |
| 2,313,164 A | 3/1943 | Nelson |

(Continued)

FOREIGN PATENT DOCUMENTS

| WO | WO-2007/111571 A1 | 10/2007 |
| WO | WO-2010/067267 A1 | 6/2010 |

(Continued)

OTHER PUBLICATIONS

Kim, K. Y., et al., "A Novel Surgical Manipulator with Workspace-Conversion Ability for Telesurgery," IEEE/ASME Transactions on Mechatronics, vol. 18, No. 1, pp. 200-211 (Feb. 2013).

(Continued)

*Primary Examiner* — Daniel W Fowler
*Assistant Examiner* — Caitlyn E May
(74) *Attorney, Agent, or Firm* — Wilson Sonsini Goodrich & Rosati

(57) ABSTRACT

A method and system for use in surgery, which includes a grasper having a jaw, and a grasper housing having a proximal end and distal end and defining a docking opening, and a tool having a tool housing having a proximal end, a distal end and defining an inner surface, and a robotic device operably coupled to the proximal end of the grasper housing, and configured to actuate the jaw of the grasper. The tool housing having an operative assembly at the distal end of the tool housing, and the tool housing defining a docking assembly at the proximal end of the tool housing. The operative assembly having a fulcrum operably coupled to the tool housing, a first lever operably connected to the fulcrum, an instrument operably coupled to the first lever, and an actuator operably coupled to the tool housing and the first lever.

28 Claims, 52 Drawing Sheets

(51) Int. Cl.
  *A61B 34/30* (2016.01)
  *A61B 17/3201* (2006.01)
  *A61B 17/00* (2006.01)
  *A61B 18/14* (2006.01)

(52) U.S. Cl.
  CPC ....... *A61B 17/3201* (2013.01); *A61B 18/1445* (2013.01); *A61B 2017/00477* (2013.01); *A61B 2017/00876* (2013.01); *A61B 2017/294* (2013.01); *A61B 2017/2931* (2013.01); *A61B 2017/2939* (2013.01)

(58) Field of Classification Search
  CPC ........ A61B 2017/294; A61B 2034/301; A61B 2034/302; A61B 34/32; A61B 34/35; A61B 34/37; A61B 17/28
  See application file for complete search history.

(56) References Cited

U.S. PATENT DOCUMENTS

| | | |
|---|---|---|
| 4,563,812 A | 1/1986 | Goddard-Watts |
| 4,573,452 A | 3/1986 | Greenberg |
| 4,620,362 A | 11/1986 | Reynolds |
| 4,676,142 A | 6/1987 | McCormick et al. |
| 4,843,921 A | 7/1989 | Kremer |
| 5,203,646 A | 4/1993 | Landsberger et al. |
| 5,368,015 A | 11/1994 | Wilk |
| 5,507,297 A | 4/1996 | Slater et al. |
| 5,515,478 A | 5/1996 | Wang |
| 5,546,508 A | 8/1996 | Jain et al. |
| 5,593,402 A | 1/1997 | Patrick |
| 5,755,661 A | 5/1998 | Schwartzman |
| 5,797,900 A | 8/1998 | Madhani et al. |
| 5,825,982 A | 10/1998 | Wright et al. |
| 5,876,325 A | 3/1999 | Mizuno et al. |
| 5,911,036 A | 6/1999 | Wright et al. |
| 6,132,368 A | 10/2000 | Cooper |
| 6,162,172 A | 12/2000 | Cosgrove et al. |
| 6,377,011 B1 | 4/2002 | Ben-Ur |
| 6,441,577 B2 | 8/2002 | Blumenkranz et al. |
| 6,459,926 B1 | 10/2002 | Nowlin et al. |
| 6,491,701 B2 | 12/2002 | Tierney et al. |
| 6,556,741 B1 | 4/2003 | Fan |
| 6,587,750 B2 | 7/2003 | Gerbi et al. |
| 6,594,552 B1 | 7/2003 | Nowlin et al. |
| 6,659,939 B2 | 12/2003 | Moll et al. |
| 6,676,684 B1 | 1/2004 | Morley et al. |
| 6,682,287 B2 | 1/2004 | Glass et al. |
| 6,714,841 B1 | 3/2004 | Wright et al. |
| 6,725,866 B2 | 4/2004 | Johnson et al. |
| 6,783,524 B2 | 8/2004 | Anderson et al. |
| 6,788,018 B1 | 9/2004 | Blumenkranz |
| 6,817,974 B2 | 11/2004 | Cooper et al. |
| 6,858,003 B2 | 2/2005 | Evans et al. |
| 6,860,878 B2 | 3/2005 | Brock |
| 6,963,792 B1 | 11/2005 | Green |
| 6,965,812 B2 | 11/2005 | Wang et al. |
| 6,969,385 B2 | 11/2005 | Moreyra |
| 7,042,184 B2 | 5/2006 | Oleynikov et al. |
| 7,121,781 B2 | 10/2006 | Sanchez |
| 7,125,403 B2 | 10/2006 | Julian et al. |
| 7,126,303 B2 | 10/2006 | Farritor et al. |
| 7,185,657 B1 | 3/2007 | Johnson et al. |
| 7,199,545 B2 | 4/2007 | Oleynikov et al. |
| 7,208,005 B2 | 4/2007 | Frecker et al. |
| 7,239,940 B2 | 7/2007 | Wang et al. |
| 7,297,142 B2 * | 11/2007 | Brock .................. A61B 5/0086 348/65 |
| 7,339,341 B2 | 3/2008 | Oleynikov et al. |
| 7,367,973 B2 | 5/2008 | Manzo et al. |
| 7,372,229 B2 | 5/2008 | Farritor et al. |
| 7,594,912 B2 | 9/2009 | Cooper et al. |
| 7,691,058 B2 | 4/2010 | Rioux et al. |
| 7,717,890 B2 | 5/2010 | Drogue et al. |
| 7,736,356 B2 | 6/2010 | Cooper et al. |
| 7,763,015 B2 | 7/2010 | Cooper et al. |
| 7,772,796 B2 | 8/2010 | Farritor et al. |
| 7,778,733 B2 | 8/2010 | Nowlin et al. |
| 7,831,292 B2 | 11/2010 | Quaid et al. |
| 7,854,738 B2 | 12/2010 | Lee et al. |
| 7,862,502 B2 | 1/2011 | Pool et al. |
| 7,862,580 B2 | 1/2011 | Cooper et al. |
| 7,950,306 B2 | 5/2011 | Stuart |
| 7,981,025 B2 | 7/2011 | Pool et al. |
| 8,016,845 B1 | 9/2011 | Sauer |
| 8,066,644 B2 | 11/2011 | Sarkar et al. |
| RE43,049 E | 12/2011 | Grace |
| 8,073,335 B2 | 12/2011 | Labonville et al. |
| 8,088,062 B2 | 1/2012 | Zwolinski |
| 8,120,301 B2 | 2/2012 | Goldberg et al. |
| 8,123,740 B2 | 2/2012 | Madhani et al. |
| 8,142,421 B2 | 3/2012 | Cooper et al. |
| 8,241,271 B2 | 8/2012 | Millman et al. |
| 8,246,533 B2 | 8/2012 | Chang et al. |
| 8,303,576 B2 | 11/2012 | Brock |
| 8,317,778 B2 | 11/2012 | Spaide |
| 8,333,780 B1 | 12/2012 | Pedros et al. |
| 8,343,171 B2 | 1/2013 | Farritor et al. |
| 8,375,808 B2 | 2/2013 | Blumenkranz et al. |
| 8,377,044 B2 | 2/2013 | Coe et al. |
| 8,398,541 B2 | 3/2013 | DiMaio et al. |
| 8,398,634 B2 | 3/2013 | Manzo et al. |
| 8,400,094 B2 | 3/2013 | Schena |
| 8,409,234 B2 | 4/2013 | Stahler et al. |
| 8,418,073 B2 | 4/2013 | Mohr et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,518,024 B2 | 8/2013 | Williams et al. |
| 8,540,748 B2 | 9/2013 | Murphy et al. |
| 8,551,076 B2 | 10/2013 | Duval et al. |
| 8,551,114 B2 | 10/2013 | Ramos de la Pena |
| 8,600,551 B2 | 12/2013 | Itkowitz et al. |
| 8,604,742 B2 | 12/2013 | Farritor et al. |
| 8,613,230 B2 | 12/2013 | Blumenkranz et al. |
| 8,620,473 B2 | 12/2013 | Diolaiti et al. |
| 8,623,028 B2 | 1/2014 | Rogers et al. |
| 8,641,700 B2 | 2/2014 | Devengenzo et al. |
| 8,667,860 B2 | 3/2014 | Helmer et al. |
| 8,679,096 B2 | 3/2014 | Farritor et al. |
| 8,682,489 B2 | 3/2014 | Itkowitz et al. |
| 8,706,301 B2 | 4/2014 | Zhao et al. |
| 8,715,159 B2 | 5/2014 | Pool et al. |
| 8,721,539 B2 | 5/2014 | Shohat et al. |
| 8,747,394 B2 | 6/2014 | Belson et al. |
| 8,758,391 B2 | 6/2014 | Swayze et al. |
| 8,761,930 B2 | 6/2014 | Nixon |
| 8,768,516 B2 | 7/2014 | Diolaiti et al. |
| 8,776,632 B2 | 7/2014 | Gao et al. |
| 8,792,951 B1 | 7/2014 | Mao et al. |
| 8,808,163 B2 | 8/2014 | Pool et al. |
| 8,827,988 B2 | 9/2014 | Belson et al. |
| 8,827,996 B2 | 9/2014 | Scott et al. |
| 8,828,024 B2 | 9/2014 | Farritor et al. |
| 8,834,488 B2 | 9/2014 | Farritor et al. |
| 8,844,789 B2 | 9/2014 | Shelton, IV et al. |
| 8,852,174 B2 | 10/2014 | Burbank |
| 8,858,538 B2 | 10/2014 | Belson et al. |
| 8,876,857 B2 | 11/2014 | Burbank |
| 8,882,660 B2 | 11/2014 | Phee et al. |
| 8,894,633 B2 | 11/2014 | Farritor et al. |
| 8,911,428 B2 | 12/2014 | Cooper et al. |
| 8,912,746 B2 | 12/2014 | Reid et al. |
| 8,919,348 B2 | 12/2014 | Williams et al. |
| 8,932,208 B2 | 1/2015 | Kendale et al. |
| 8,936,544 B2 | 1/2015 | Shahoian et al. |
| 8,942,828 B1 | 1/2015 | Schecter |
| 8,944,997 B2 | 2/2015 | Fernandez et al. |
| 8,945,095 B2 | 2/2015 | Blumenkranz et al. |
| 8,945,163 B2 | 2/2015 | Voegele et al. |
| 8,945,174 B2 | 2/2015 | Blumenkranz |
| 8,956,351 B2 | 2/2015 | Ravikumar et al. |
| 8,968,332 B2 | 3/2015 | Farritor et al. |

(56) References Cited

U.S. PATENT DOCUMENTS

| | | | |
|---|---|---|---|
| 8,974,374 B2 | 3/2015 | Schostek et al. |
| 8,979,857 B2 | 3/2015 | Stad et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,565 B2 | 3/2015 | Brisson et al. |
| 8,992,566 B2 | 3/2015 | Baldwin |
| 8,996,173 B2 | 3/2015 | Itkowitz et al. |
| 9,002,518 B2 | 4/2015 | Manzo et al. |
| 9,005,112 B2 | 4/2015 | Hasser et al. |
| 9,011,434 B2 | 4/2015 | Kappel et al. |
| 9,028,468 B2 | 5/2015 | Scarfogliero et al. |
| 9,028,494 B2 | 5/2015 | Shelton, IV et al. |
| 9,039,685 B2 | 5/2015 | Larkin et al. |
| 9,044,256 B2 | 6/2015 | Cadeddu et al. |
| 9,052,710 B1 | 6/2015 | Farwell |
| 9,055,960 B2 | 6/2015 | Stoy et al. |
| 9,060,678 B2 | 6/2015 | Larkin et al. |
| 9,060,770 B2 | 6/2015 | Shelton, IV et al. |
| 9,077,973 B2 | 7/2015 | Aguren |
| 9,078,684 B2 | 7/2015 | Williams |
| 9,078,695 B2 | 7/2015 | Hess et al. |
| 9,089,352 B2 | 7/2015 | Jeong |
| 9,089,353 B2 | 7/2015 | Farritor et al. |
| 9,095,317 B2 | 8/2015 | Cooper et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,107,686 B2 | 8/2015 | Moon et al. |
| 9,119,655 B2 | 9/2015 | Bowling et al. |
| 9,144,452 B2 | 9/2015 | Scott et al. |
| 9,155,764 B1 | 10/2015 | Ahn et al. |
| 9,173,643 B2 | 11/2015 | Morley et al. |
| 9,173,707 B2 | 11/2015 | Singh |
| 9,173,915 B1 | 11/2015 | Kador |
| 9,179,912 B2 | 11/2015 | Yates et al. |
| 9,179,979 B2 | 11/2015 | Jinno |
| 9,186,215 B2 | 11/2015 | Singh |
| 9,186,220 B2 | 11/2015 | Stefanchik et al. |
| 9,194,403 B2 | 11/2015 | Neyme |
| 9,198,714 B2 | 12/2015 | Worrell et al. |
| 9,216,062 B2 | 12/2015 | Duque et al. |
| 9,220,567 B2 | 12/2015 | Sutherland et al. |
| 9,226,750 B2 | 1/2016 | Weir et al. |
| 9,226,751 B2 | 1/2016 | Shelton, IV et al. |
| 9,226,761 B2 | 1/2016 | Burbank |
| 9,241,766 B2 | 1/2016 | Duque et al. |
| 9,259,274 B2 | 2/2016 | Prisco |
| 9,259,275 B2 | 2/2016 | Burbank |
| 9,261,172 B2 | 2/2016 | Solomon et al. |
| 9,271,857 B2 | 3/2016 | Pool et al. |
| 9,272,166 B2 | 3/2016 | Hartman et al. |
| 9,301,759 B2 | 4/2016 | Spivey et al. |
| 9,303,212 B2 | 4/2016 | Flegal |
| 9,305,123 B2 | 4/2016 | Leotta et al. |
| 9,308,011 B2 | 4/2016 | Chao et al. |
| 9,308,145 B2 | 4/2016 | Jackson |
| 9,309,094 B2 | 4/2016 | Hoffend, III |
| 9,314,153 B2 | 4/2016 | Stein et al. |
| 9,314,239 B2 | 4/2016 | Brown |
| 9,315,235 B1 | 4/2016 | Wood |
| 9,326,823 B2 | 5/2016 | McMillan et al. |
| 9,327,081 B2 | 5/2016 | Gobron et al. |
| 9,333,003 B2 | 5/2016 | Kappel et al. |
| 9,333,041 B2 | 5/2016 | Yeung et al. |
| 9,358,031 B2 | 6/2016 | Manzo |
| 9,358,075 B2 | 6/2016 | Kim et al. |
| 9,360,093 B2 | 6/2016 | Garner |
| 9,366,862 B2 | 6/2016 | Haddick et al. |
| 9,375,288 B2 | 6/2016 | Robinson et al. |
| 9,386,983 B2 | 7/2016 | Swensgard et al. |
| 9,393,017 B2 | 7/2016 | Flanagan et al. |
| 9,398,911 B2 | 7/2016 | Auld |
| 9,399,298 B2 | 7/2016 | Kang |
| 9,399,558 B2 | 7/2016 | Guernsey et al. |
| 9,402,688 B2 | 8/2016 | Min et al. |
| 9,403,281 B2 | 8/2016 | Farritor et al. |
| 9,404,734 B2 | 8/2016 | Ramamurthy et al. |
| 9,408,369 B2 | 8/2016 | Dubinsky |
| 9,408,607 B2 | 8/2016 | Cartledge et al. |
| 9,408,668 B2 | 8/2016 | Durant et al. |
| 9,456,735 B2 | 10/2016 | Hrayr et al. |
| 9,457,168 B2 | 10/2016 | Moll et al. |
| 9,460,880 B2 | 10/2016 | Melecio Ramirez et al. |
| 9,463,015 B2 | 10/2016 | Hausen |
| 9,463,059 B2 | 10/2016 | Suon et al. |
| 9,464,643 B2 | 10/2016 | Shu |
| 9,476,245 B2 | 10/2016 | Hansen |
| 9,566,709 B2 | 2/2017 | Kwon et al. |
| 9,579,163 B2 | 2/2017 | Valdastri et al. |
| 9,801,618 B2 | 10/2017 | Sachs et al. |
| 2005/0096502 A1 | 5/2005 | Khalili |
| 2005/0283137 A1* | 12/2005 | Doyle ............... A61B 17/1222 |
| | | 606/1 |
| 2006/0052669 A1 | 3/2006 | Hart |
| 2006/0178556 A1 | 8/2006 | Hasser et al. |
| 2006/0199999 A1 | 9/2006 | Ikeda et al. |
| 2007/0074584 A1 | 4/2007 | Talarico et al. |
| 2008/0000317 A1 | 1/2008 | Patton et al. |
| 2008/0004634 A1 | 1/2008 | Farritor et al. |
| 2008/0064931 A1 | 3/2008 | Schena et al. |
| 2008/0147090 A1* | 6/2008 | Seibold ............... A61B 34/71 |
| | | 606/130 |
| 2008/0221591 A1 | 9/2008 | Farritor et al. |
| 2009/0076536 A1 | 3/2009 | Rentschler et al. |
| 2009/0112229 A1 | 4/2009 | Omori et al. |
| 2009/0157076 A1 | 6/2009 | Athas et al. |
| 2009/0171373 A1 | 7/2009 | Farritor et al. |
| 2009/0177452 A1 | 7/2009 | Ullrich et al. |
| 2009/0209947 A1* | 8/2009 | Gordin ............... A61B 1/122 |
| | | 606/1 |
| 2009/0245600 A1 | 10/2009 | Hoffman et al. |
| 2009/0248041 A1 | 10/2009 | Williams et al. |
| 2010/0041938 A1 | 2/2010 | Stoianovici et al. |
| 2010/0160929 A1 | 6/2010 | Rogers et al. |
| 2010/0245549 A1 | 9/2010 | Allen et al. |
| 2010/0331858 A1 | 12/2010 | Simaan et al. |
| 2011/0071347 A1 | 3/2011 | Rogers et al. |
| 2011/0202070 A1 | 8/2011 | Dario et al. |
| 2011/0230894 A1 | 9/2011 | Simaan et al. |
| 2011/0238080 A1 | 9/2011 | Ranjit et al. |
| 2012/0046525 A1 | 2/2012 | Russell et al. |
| 2012/0078053 A1 | 3/2012 | Phee et al. |
| 2012/0190920 A1 | 7/2012 | Hasser et al. |
| 2012/0209314 A1 | 8/2012 | Weir et al. |
| 2012/0265214 A1 | 10/2012 | Bender et al. |
| 2012/0310256 A1 | 12/2012 | Brisson |
| 2012/0316575 A1 | 12/2012 | Farin et al. |
| 2012/0323256 A1* | 12/2012 | Privitera ............... A61B 34/30 |
| | | 606/130 |
| 2013/0023860 A1 | 1/2013 | Nagashimada |
| 2013/0085510 A1 | 4/2013 | Stefanchik et al. |
| 2013/0107665 A1 | 5/2013 | Fletcher et al. |
| 2013/0131695 A1 | 5/2013 | Scarfogliero et al. |
| 2013/0281924 A1 | 10/2013 | Shellenberger |
| 2013/0321262 A1 | 12/2013 | Schecter |
| 2014/0005640 A1 | 1/2014 | Shelton, IV et al. |
| 2014/0012287 A1 | 1/2014 | Oyola et al. |
| 2014/0066955 A1 | 3/2014 | Farritor et al. |
| 2014/0107665 A1 | 4/2014 | Shellenberger et al. |
| 2014/0114327 A1 | 4/2014 | Boudreaux et al. |
| 2014/0222020 A1 | 8/2014 | Bender et al. |
| 2014/0276667 A1 | 9/2014 | Shellenberger et al. |
| 2014/0276944 A1 | 9/2014 | Farritor et al. |
| 2015/0026537 A1 | 1/2015 | Romanovskyy et al. |
| 2015/0038984 A1 | 2/2015 | Hiroe et al. |
| 2015/0119638 A1 | 4/2015 | Yu et al. |
| 2015/0130599 A1 | 5/2015 | Berkley et al. |
| 2015/0250546 A1 | 9/2015 | Larkin et al. |
| 2016/0184032 A1 | 6/2016 | Romo et al. |
| 2016/0332305 A1 | 11/2016 | Gonzalez et al. |
| 2017/0181802 A1 | 6/2017 | Sachs et al. |

(56) References Cited

U.S. PATENT DOCUMENTS

FOREIGN PATENT DOCUMENTS

| WO | WO-2010/126127 A1 | 11/2010 |
| WO | WO-2011/040769 A2 | 4/2011 |
| WO | WO-2011/060046 A2 | 5/2011 |
| WO | WO-2011/135503 A1 | 11/2011 |
| WO | WO-2011/137336 A1 | 11/2011 |
| WO | WO-2012/044334 A2 | 4/2012 |
| WO | WO-2012/060586 A2 | 5/2012 |
| WO | WO-2013/180773 A1 | 12/2013 |
| WO | WO-2014/011969 A1 | 1/2014 |
| WO | WO-2014/073121 A1 | 5/2014 |
| WO | WO-2015/063524 A1 | 5/2015 |
| WO | WO-2015/115887 A1 | 8/2015 |
| WO | WO-2015/171614 A1 | 11/2015 |
| WO | WO-2016/083189 A1 | 6/2016 |

OTHER PUBLICATIONS

Can, S., et al., "The "Highly Versatile Single Port System" for laparpscopic surgery: Introduction and first clinical application," 4th European Conference of the International Federation for Medical and Biological Engineering, vol. 22, pp. 1650-1654 (2009).

Oppenheimer, et al., "Immersive Surgical Robotic Interfaces," Human Interface Technology Lab, University of Washington, Paper presented at *Medicine Meets Virtual Reality* (MMVR 1999), Jan. 20-23, 1999, San Francisco, California, 7 pages.

Song, et al., "The Development of Human-Arm Like Manipulator for Laparoscopic Surgery With Force Sensing," 2006 IEEE International Conference on Industrial Technology, Mumbai, 2006, pp. 1258-1262, 5 pages.

Ali Talasaz, "Haptics-Enabled Teleoperation for Robotics-Assisted Minimally Invasive Surgery," May 2012, *Electronic Thesis and Dissertation Repository*, Paper 498, 175 pages.

* cited by examiner

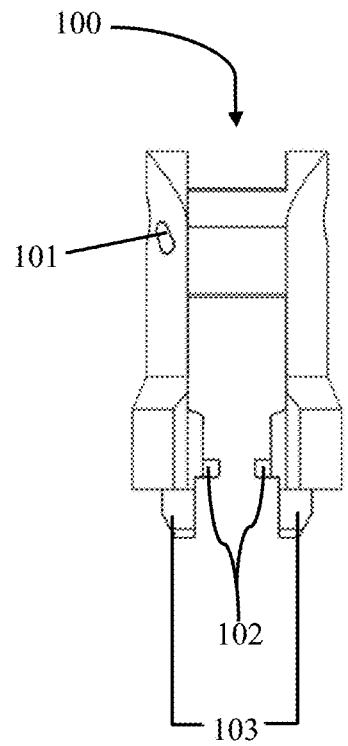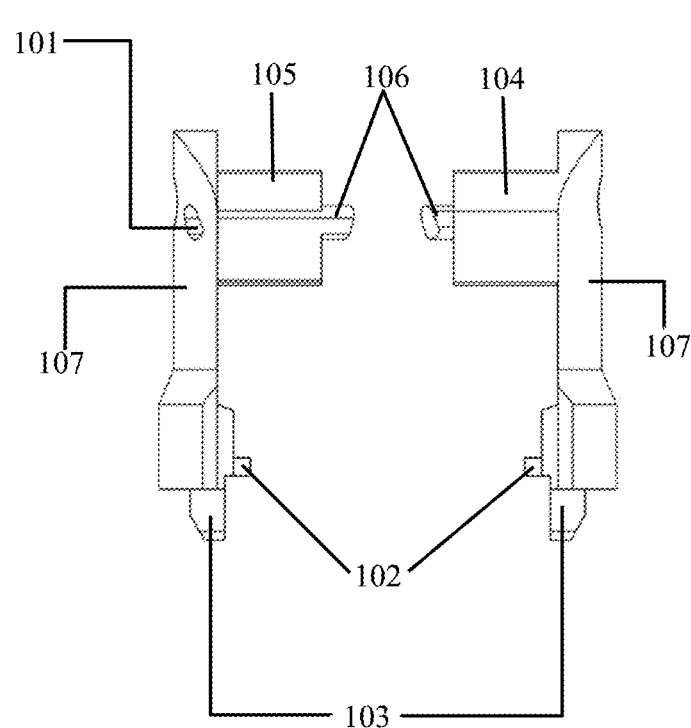
FIG. 2A          FIG. 2B
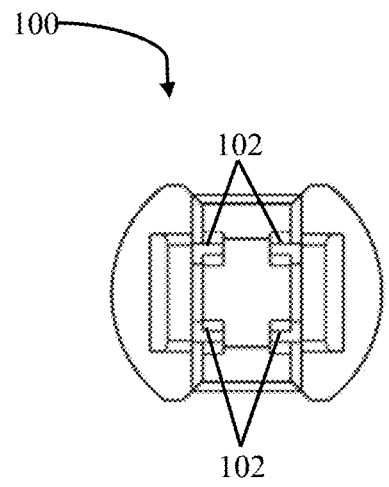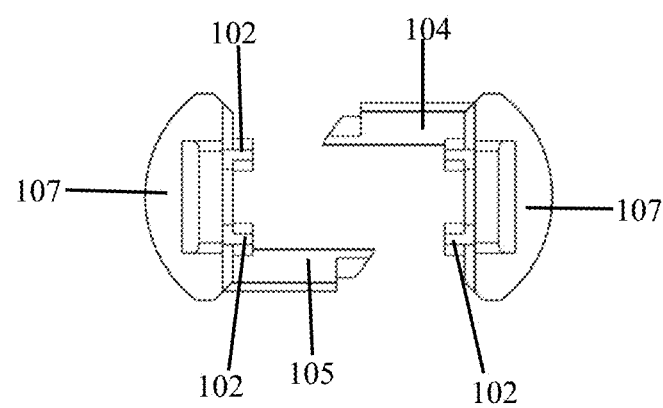
FIG. 2C          FIG. 2D

VIRTUAL REALITY SURGICAL TOOLS SYSTEM

CROSS-REFERENCES TO RELATED APPLICATIONS

This application claims the benefit under 35 U.S.C. § 119(e) to U.S. Provisional Patent Application No. 62/456,926, entitled Virtual Reality Surgical Tools System filed on Feb. 9, 2017, and U.S. Provisional Patent Application No. 62/532,054, entitled Virtual Reality Surgical Tools System filed on Jul. 13, 2017, which are hereby incorporated by reference in their entirety.

BACKGROUND

Field of Invention

This application generally relates to minimally invasive surgery, minimally invasive surgical tools and virtual reality minimally invasive surgical systems.

Description of Related Art

From its onset in the 1990's the minimally invasive surgical field has developed and grown expeditiously, with said developments and growth producing improved results for patients. As a result of the growth and developments in the field, more and more types of procedures are now being conducted using minimally invasive surgery techniques and systems. One of the major differences between conventional "open" surgery and minimally invasive surgery is how the surgeon obtains access to the surgical site. In a conventional "open" surgery, typically a rather large incision is made from below the patient's breastbone to the patient's navel or beyond. In comparison, during a minimally invasive surgery, a series of small incisions are made, which allows a surgeon to insert an endoscope or other type of camera through one of the small incisions and insert different surgical tools and/or instruments through the other incisions. While minimally invasive surgery has provided patients with improved outcomes, it has come at an expense to the surgeon's ability to operate with precision and ease, as a surgeon is constrained by its insertion point both in movement of their instruments and the number of instruments that can be inserted at a surgical site at a given time.

During both a conventional "open" surgery and minimally invasive surgery, a surgeon utilizes numerous different tools, to perform different surgical functions. Such tools can include but are not limited to, tools for needle driving, grasping, ablation, cautery, clip application, stabling, sharp dissection, irrigation, and suction. As stated above, in typical minimally invasive surgeries, a surgeon utilizes multiple small incisions in a patient's body to insert different surgical instruments and tools to perform different surgical functions. While more appealing than conventional "open" surgeries, the multiple incisions necessary to perform a minimally invasive surgery leave a lot to be desired, as multiple incisions leaves a patient vulnerable to multiple infections and hernias, as well as skin and soft tissue trauma.

Surgeons have attempted to relieve some of these issues by utilizing surgical robotic devices to physically perform the operation. However, many surgical robotic devices require multiple incision points to allow a surgeon access to multiple surgical tools. Furthermore, surgical robotic devices create an increased disconnect between the surgeon and the surgical instruments of the robotic device. This disconnect has led to injuries as a surgeon is not fully aware of the motion and/or force being applied by the robotic device. As a result of being unaccustomed to the multiple degrees of freedom of many of existing robotic devices, surgeons must exhaustively train on robotic simulators before operating on a patient to decrease the possibility of an inadvertent injury.

In an attempt to avoid the need for multiple incision points, some surgeons have utilized single incision surgical robotic devices. However, existing single incision surgical robotic devices have many drawbacks, resulting from the size of their actuation mechanisms, which have been incorporated into their in vivo robot. Currently some single incision robotic devices incorporate servomotors, gearboxes, and encoders, among other actuation mechanisms within the in vivo robot. The incorporation of the actuator mechanisms into an in vivo robot has resulted in large robots with narrow capabilities. The implementation of large single-incision robotic devices have resulted in the need for large incisions to be made, which comes with an increase in patient's susceptibility for infection, pain, herniation, and general morbidity. In addition, the single incision devices have limited degrees of freedom, with some of these degrees of freedom being non-intuitive to a human. These non-intuitive degrees of freedom require a user interface that allows a surgeon to make non-intuitive learned movements which are similar to multi-incision devices.

Furthermore, existing single incision devices are constrained in the number of surgical tools and instruments that are readily accessible to a surgeon during an operation. Some single-incision devices have attempted to alleviate this issue by allowing different tools and instruments to be switched out with one another. However, in order to switch between tools a surgeon must remove the entire device from the patient's body and then manually replace it, which has significant drawbacks. These drawbacks include increased patient susceptibility to infection, herniation, pain and general morbidity due to increase in the number of times the device is removed and reinserted. Furthermore, this exchange increases the time it takes to perform an operation and disrupts a surgeon's workflow.

Alternative single incision devices have attempted to eliminate the need to remove the entire device in order to switch between tools by having multifunctional tools. However, in this implementation a surgeon is limited to the functions that said multifunctional tool is capable of performing. Due to this limitation, a surgeon still needs to remove the device from the patient's body and attach a different tool and/or insert an entirely different device to perform a different function that the multifunctional tool is unable to perform.

In other single-incision devices, a surgeon interchanges tools while the device remains located within the patient's body. However, with these devices the surgeon must completely remove the entire end effector, which encompasses a tool and typically the driving mechanism of the tool. While the surgeon is removing and substituting end effectors, the entire apparatus is rendered incapacitated, interrupting the operation and disrupting the surgeon's work flow. Moreover, different end effectors can encompass different driving mechanisms which limits what tools can be attached to what manipulator and also what tools can be used at the same time, thus interrupting the operation and increasing operating time.

As with conventional minimally invasive operations as well as with existing robotic surgeries, a surgeon removes the instrument from the surgical site and then inserts a new instrument. While removing instruments and inserting new instruments is a viable option in conventional minimally invasive operations and existing robotic surgeries, it is unpractical and not an intuitive method for interchanging tools during virtual reality surgeries. In virtual reality surgeries, the surgeon has the perception of being condensed inside a patient's body at a surgical site. A small robot placed within the patient replicates the motion of the surgeon's arms and hands. In conjunction with three-dimensional visualization provided by virtual reality goggles, the surgeon views the operation and interacts with the robotic arms as if the robotic arms have taken the form of the surgeon's arms and hands. With this natural humanlike robot located within a patient it is not ideal for a surgeon to remove the robot to exchange between instruments. Removal and insertion of the robotic device would be cumbersome, and would require a surgeon to disconnect and remove his/herself from the natural and immersive virtual reality user interface. In order to allow a surgeon to remain immersed in the natural and immersive virtual reality user interface, a different technique of exchanging surgical instruments is necessary for virtual reality surgery.

With human-like robotics systems, having a successful system results from maintaining a natural and intuitive human-machine interface (HMI). As such, it is advantageous in a virtual reality surgery for a surgeon to be able to interact with the requisite tools while maintaining the functionality of a human-like robot.

BRIEF SUMMARY OF INVENTION

The system allows a surgeon to exchange between different surgical tools and apparatuses during a minimally invasive surgery procedure. In one embodiment the technology includes a system comprising a grasper comprising, a grasper housing having a distal end and a proximal end, the grasper housing defining a docking opening at the distal end, the docking opening having a shape, and a jaw at the distal end of the grasper housing, the jaw including a first jaw portion and a second jaw portion, the first and second jaw portions being movably opposed, at least one of the first and second jaw portions comprises at least one actuation mating surface, a tool comprising, a tool housing having a distal end and a proximal end and defining an inner surface, a docking assembly defined by the tool housing at the proximal end of the tool housing, the docking assembly comprising a first protrusion extending proximally from the proximal end of the tool housing and having a first protrusion shape complementary to the shape of the docking opening, and an operative assembly at the distal end of the tool housing, the operative assembly comprising, a fulcrum operably coupled to the tool housing, a first lever operably connected to the fulcrum, an instrument operably coupled to the first lever, and an actuator operably coupled to the tool housing and the first lever, and a robotic device operably coupled to the proximal end of the grasper and configured to actuate the first and second jaw portions of the grasper between a first jaw position and a second jaw position. In an implementation of the embodiment, the first protrusion of the docking assembly of the tool is configured to cooperate with the docking opening of the grasper housing to constrain the tool in all axes relative to the grasper. In an implementation of the embodiment, the first lever comprises a proximal end configured to ride along the at least one actuation mating surface of one of the first or second jaw portions of the grasper. In an implementation of the embodiment, the actuator is configured to apply a force upon the first lever to bias the first lever in a first direction.

In an implementation of the embodiment at least one of the first and second jaw portions of the grasper is configured to apply a force on the first lever to rotate the first lever about the fulcrum from a first lever position to a second lever position. In an aspect of an implementation the actuator is configured to retain an energy from the force applied by the at least one of the first and second jaw portions. In an aspect of an implementation, the actuator is configured to release the energy retained by said actuator as a force upon the at least one lever to rotate the at least one lever about the fulcrum from the second lever position to the first lever position.

In an implementation of the embodiment, the first jaw portion is fixed relative to the grasper housing and the second jaw portion is movable relative to the first jaw portion. In an implementation of the embodiment, the first and second jaw portions are independently movable.

In an implementation of the embodiment, the tool housing comprises a plurality of tool housing segments, with said segments defining a tool housing interior, and the plurality of tool housing segments are coupled by at least one support. In one aspect of an implementation comprising a plurality of tool housing segments, the actuator is operably coupled to the interior of one of the plurality of tool housing segments.

In an implementation of the embodiment, at least one of the first and second jaw portions define a channel having a channel shape and the docking assembly further comprises a second protrusion extending from the inner surface of the tool housing that has a second protrusion shape complementary to the channel shape. In an aspect of an implementation, the first protrusion of the docking assembly is configured to cooperate with the docking opening of the grasper housing and the second protrusion of the docking assembly is configured to cooperate with the channel of the at least one of the first and second jaw portions to constrain the tool in all axes relative to the grasper.

In an implementation of the embodiment, the first jaw portion comprises an electrically conductive contact portion at a distal end of the jaw portion, and an electrical conductor coupled to the conductive contact portion and the first jaw portion is electrically insulated. In an implementation of the embodiment, the first and second jaw portions are electrically conductive and the first jaw portion is coupled to a first electrical conduction and the second jaw portion is coupled to a second electrical conductor, and the embodiment further comprises a power supply coupled to the first and second electrical conductors for supplying electrical power to the first and second jaw portions, and the first and second jaw portions are electrically insulated.

In one implementation of the embodiment, the operative assembly of the tool further comprises a second lever operably coupled to the fulcrum, a second instrument operably coupled to the second lever, and the first and second levers each comprise a proximal end and the first and second jaw portions of the grasper each comprise at least one actuation mating surface. In an aspect of an implementation, the proximal end of the first lever is configured to ride along the at least one actuation mating surface of the first jaw portion and the proximal end of the second lever is configured to ride along the at least one actuation mating surface of the second jaw portion. In an aspect of an implementation, the first and second lever are configured to move independently of one another. In an aspect of an implementation, the operative assembly of the tool further comprises a second actuator operably coupled to the tool housing and the second lever.

In one implementation of the embodiment, the instrument of the operative assembly is one of surgical scissors, needle driver, forceps, grasper, retractor, surgical stapler, vessel sealer, surgical drill, cautery pen, cautery hook or caliper. In an implementation of the embodiment, the instrument comprises a first component and a second component, the first component operably coupled to the first lever and the second component operably coupled to a second lever.

In an implementation of the embodiment, the first jaw portion further comprises a force-open channel having a force-open channel shape and the first lever of the tool further comprises a proximal end comprising a projection having a projection shape complementary to the force-open channel. In an aspect of an implementation, when a tool couples to the grasper the projection of the first lever is configured to cooperate with the force-open channel of the first jaw portion of the grasper to allow the projection to pass through the force-open channel and maintain a clearance over the first jaw portion. In an aspect of an implementation, the first jaw portion of the grasper is configured to apply a force upon the projection of the first lever as the first jaw portion moves from the second jaw position to the first jaw position to rotate the first lever about the fulcrum from a second lever position to a first lever position.

In an implementation of the embodiment the first jaw portion of the grasper further comprises a first force-open channel having a first force-open channel shape and the first lever of the operative assembly further comprises a proximal end with a first projection having a first projection shape complementary to the first force-open channel of the first jaw portion and the second jaw portion of the grasper further comprises a second force-open channel having a second force-open channel shape and the operative assembly of the tool further comprises a second lever having a second instrument and a proximal end having a second projection having a second projection shape complementary to the second force-open channel of the second jaw portion.

In an implementation of the embodiment, the grasper housing further defines a plurality of docking openings with each of the plurality of docking openings having a shape and the docking assembly of the tool further comprises a plurality of first protrusions extending proximally form the proximal end of the tool housing and each of the first protrusions having a corresponding shape complementary to the shape of one of the plurality of docking openings, and the first protrusions of the docking assembly of the tool are configured to cooperate with the plurality of docking openings of the grasper housing to constrain the tool in all axes relative to the grasper.

In an implementation of the embodiment the first jaw portion defines a plurality of channels with each of the plurality of channels having a channel shape and the second jaw portion defines a plurality of channels with each of the plurality of channels having a channel shape, and the docking assembly further comprises a plurality of second protrusions extending form the inner surface of the tool housing, each of the plurality of second protrusions having a corresponding second protrusion shape complementary to the channel shape of the plurality of channels of the first jaw portions and the channel shape of the plurality of channels of the second jaw portion.

In an implementation of the embodiment, the first protrusion of the docking assembly of the tool comprises a first magnetic contact having a first magnetic contact shape and the docking opening of the grasper housing comprises a second magnetic contact having a second magnetic contact shape complementary to the first magnetic contact of the first protrusion, with the first magnetic contact of the first protrusion of the docking assembly of the tool configured to cooperate with second magnetic contact of the docking opening of the grasper to constrain the tool in all axes relative to the grasper.

In a second embodiment the technology includes a system comprising a grasper comprising, a grasper housing having a distal end and a proximal end, the grasper housing defining a docking opening at the distal end, the docking opening having a shape, and a jaw at the distal end of the grasper housing, the jaw including a first jaw portion and a second jaw portion, with at least one of the first and second jaw portions movably relative to the other, and a tool comprising a tool housing having a distal end and a proximal end and defining an inner surface, a docking assembly defined by the tool housing at the proximal end of the tool housing, the docking assembly comprising a first protrusion extending proximally from the proximal end of the tool housing and having a first protrusion shape complementary to the shape of the docking opening, and an operative assembly at the distal end of the tool housing, the operative assembly comprising an instrument operably connected to the tool housing, and a robotic device operably coupled to the proximal end of the grasper and configured to actuate the first and second jaw portions of the grasper between a first position and a second position. In the system, the first protrusion of the docking assembly of the tool is configured to cooperate with the docking opening of the grasper housing to constrain the tool in all axes relative to the grasper.

In an implementation of the second embodiment, the first jaw portion is fixed relative to the grasper housing and the second jaw portion is movable relative to the first jaw portion. In an implementation of the second embodiment, the first and second jaw portions of the grasper are independently movable. In an implementation of the second embodiment, the first and second jaw portions of the grasper are movably opposed.

In an implementation of the second embodiment, the instrument of the operative assembly is one of a cautery hook, scalpel, cautery pen, surgical probe, biopsy puncher, dissector, curette, gouge, knife, impactor, rasps, retractor, saw, separator, spatula, stripper, or surgical needle.

In an implementation of the second embodiment, the tool housing comprises a plurality of tool housing segments, the plurality of tool housing segments defines a tool housing interior and with the plurality of tool housing segments coupled by at least one support.

In an implementation of the second embodiment, at least one of the first and second jaw portions of the grasper defines a channel having a channel shape and the docking assembly of the tool further comprises a second protrusion extending form the inner surface of the tool housing that has a second protrusion shape complementary to the channel shape of the at least one of the first and second jaw portions of the grasper, and the first protrusion of the docking assembly of the tool is configured to cooperate with the docking opening of the grasper housing and the second protrusion of the docking assembly is configured to cooperate with the channel of the at least one of the first and second jaw portions of the grasper to constrain the tool in all axes relative to the grasper.

In an implementation of the second embodiment the first jaw portion comprises an electrically conductive contact portion at a distal end of the jaw portion, and an electrical conductor coupled to the conductive contact portion, and the first jaw portion is electrically insulated. In an aspect of an implementation, the tool housing of the tool comprises an electrically conductive contact disposed on the inner surface of the tool housing and the first jaw portion is configured to transmit electrical power to the electrical conductive contact of the tool housing. In an aspect of an implementation, the electrically conductive contact of the tool housing is operably coupled to the instrument of the operative assembly to transfer electrical power to said instrument.

In an implementation of the second embodiment, the first jaw portion is electrically conductive and is coupled to a first electrical conductor and the second jaw portion is electrically conductive and is coupled to a second electrical conductor. In an aspect of an implementation, the tool housing comprises a plurality of electrically conductive contacts operably coupled to the instrument of the operative assembly, and the first and second jaw portions are configured to transfer electrical power to the plurality of electrically conductive contacts for supplying electrically power to the instrument.

In an implementation of the second embodiment, the grasper housing further defines a plurality of docking openings, each of the plurality of docking openings having a shape, and the docking assembly of the tool further comprising a plurality of first protrusions extending proximally form the proximal end of the tool housing and each of the plurality of first protrusions having a corresponding first protrusion shape complementary to the shape of one of the plurality of docking openings, and wherein the plurality of first protrusions of the docking assembly of the tool are configured to cooperate with the plurality of docking openings of the grasper housing to constrain the tool in all axes relative to the grasper.

In an implementation of the second embodiment, the first jaw portion defines a plurality of channels, each of the plurality of channels having a channel shape and the second jaw portion defines a plurality of channels each of the plurality of channels having a channel shape and the docking assembly further comprising a plurality of second protrusions extending from the inner surface of the tool housing, each of the second protrusions having a corresponding second protrusion shape complementary to the channel shape of the plurality of channels of the first jaw portion and the channel shape of the plurality of channels of the second jaw portion.

In an implementation of the second embodiment, at least one of the first and second jaw portions is configured to be electrified and at least one of the first and second jaw portions is configured to supply electrical power to the instrument of operative assembly.

The technology includes an embodiment of a method comprising, providing a grasper comprising, a grasper housing having a distal end and a proximal end, the grasper housing defining a docking opening at the distal end, the docking opening having a shape, and a jaw at the distal end of the grasper housing, the jaw including a first jaw portion and a second jaw portion, the first and second jaw portions being movably opposed, providing a tool comprising, a tool housing having a distal end and a proximal end and defining an inner surface, a docking assembly defined by the tool housing at the proximal end of the tool housing, the docking assembly comprising a first protrusion extending proximally from the proximal end of the tool housing and having a first protrusion shape complementary to the shape of the docking opening, and an operative assembly at the distal end of the tool housing, adjusting the jaw of the grasper to a first jaw position, and disposing the first protrusion of the docking assembly into the docking opening of the grasper housing. In the method, the operative assembly of the tool further comprises an instrument operably coupled to the tool housing.

In an implementation of the method, at least one of the first and second jaw portions of the grasper defines a channel having a channel shape, and the docking assembly further comprises a second protrusion extending from the inner surface of the tool housing having a second protrusion shape complementary to the channel shape. In an implementation of the method, the disposing step further comprising the step of simultaneously aligning the second protrusion of the docking assembly with the channel of at least one of the first and second jaw portions of the jaw. In an aspect, the method further comprises the step of adjusting the jaw of the grasper to a second jaw position that is relatively more closed than the first jaw position to cause the second protrusion of the docking assembly to enter the channel of at least one of the first and second jaw portions of the grasper.

In one implementation of the method, the operative assembly of the tool further comprises, a fulcrum operably coupled to the tool housing, a lever operably coupled to the fulcrum, an instrument operably coupled to the lever, and an actuator operably coupled to the tool housing and the at least one lever. In one implementation of the method, the first jaw portion of the jaw of the grasper further comprises at least one actuation mating surface and the second jaw portion of the jaw of the grasper further comprises at least one actuation mating surface. In an aspect, the method further comprising the step of adjusting the jaw of the grasper to a second jaw position that is relatively more closed than the first jaw position to cause the lever of the operative assembly to mate with the actuation mating surface of one of the first or second jaw portions. In an aspect, the method further comprising the step of applying a force upon the lever of the tool using the jaw of the grasper, as the jaw of the grasper moves towards a closed jaw position to cause the lever to ride along the actuation mating surface of one of the first or second jaw portions while the lever rotates about the fulcrum from a first lever position to a second lever position. In an aspect, the method further comprising the step of administering a force upon the lever with the actuator to cause the lever to rotate around the fulcrum from the second lever position to the first lever position as the jaw of the grasper moves from the closed jaw position towards the first jaw position, while the lever rides along the actuation mating surface of one of the first or second jaw portions.

In an implementation of the method, the instrument comprises, a fulcrum operably coupled to the tool housing, a first and second lever operably coupled to the fulcrum, a first instrument component operably coupled to the first lever, a second instrument operably coupled to the second lever, a first actuator operably coupled to the tool housing and the first lever, and a second actuator operably coupled to the tool housing and the second lever. In an aspect of an implementation, the first jaw portion of grasper further comprises a first actuation mating surface and second actuation mating surface and the second jaw portion of the grasper further comprises a first actuation mating surface and second actuation mating surface. In an aspect, the method further comprises the step of adjusting the jaw of the grasper to a second jaw position that is relatively more closed than the first jaw position to cause the first lever of the instrument to mate with one of the first or second actuation mating surface of one of the first or second jaw portions and the second lever to mate with one of the first or second actuation mating surface of one of the first or second jaw portions. In an aspect, the method further comprises a step of applying a force upon the first and second levers of the instrument using the jaw of the grasper as said jaw moves from the second jaw position towards a third jaw position that is relatively more closed than the second jaw position to cause the first lever to rotate about the fulcrum from a first lever position to a second lever position while the first lever rides along one of the first or second actuation mating surface of one of the first or second jaw portions and the second lever rotates about the fulcrum from the first lever position to the second lever position while the second lever rides along one of the first or second actuation mating surface of one of the first or second jaw portions. In an aspect, the method further comprises the step of moving the jaw of the grasper from the third jaw position to the first jaw position thereby enabling the first actuator to apply a force upon the first lever and enabling the second actuator to apply a force upon the second lever, the force applied by the first actuator causes the first lever to rotate about the fulcrum from the second lever position to the first lever position while the first lever rides along one of the first or second actuation mating surface of one of the first or second jaw portions and the force applied by the second actuator causes the second lever to rotate about the fulcrum from the second lever position to the first lever position while the second lever rides along one of the first or second actuation mating surface of one of the first or second jaw portions.

In an implementation the method, the operative assembly further comprises an instrument operably connected to the tool housing and the tool housing further comprises a plurality of electrically conductive contacts that are operably connected to the instrument and at least one of the first and second jaw portions is electrically conductive and is coupled to a first electrical conductor coupled to a power supply and said method further comprises mating the at least one of the first or second jaw portions that is electrically conductive with the plurality of electrically conductive contacts of the tool housing to transfer electrical power from the at least one of the first or second jaw portions that is electrically conductive to the plurality of electrically conductive contacts to cause the instrument to become electrified.

In an implementation of the method, the operative assembly of the tool further comprises a fulcrum operably coupled to the tool housing, a lever comprising a proximal end comprising a proximal end comprising a projection and operably connected to the fulcrum, and instrument operably coupled to the lever, and an actuator operably coupled to the tool housing and the least one lever. In an aspect of an implementation, at least one of the first and second jaw portions of the grasper comprises a force-open channel having a force-open shape complementary to the projection of the lever, and at least one of the first and second jaw portions of the grasper comprises a top surface and at least one actuation mating surface configured to cooperate with the lever and said method further comprises the step of orientating the instrument to a closed instrument position. In an aspect, the method further comprises the step of adjusting the jaw of the grasper to a closed jaw position to cause the projection of the lever to pass through the force-open channel of one of the first or second jaw portions of the grasper, while simultaneously aligning and mating the lever with the actuation mating surface of one of the first or second jaw portions and while one of the first or second jaw portions of the grasper simultaneously applies a force upon the lever of the operative assembly. In an aspect, the method further comprises the step of adjusting the jaw of the grasper from the closed jaw position towards an open jaw position to allow the actuator of the operative assembly to simultaneously administer a force upon the lever to cause the projection of the lever to maintain a clearance above the top surface of one of the first or second jaw portions of the grasper, while simultaneously allowing the lever to ride along the actuation mating surface of one of the first or second jaw portions, while the lever rotates about the fulcrum to cause the instrument of the operative assembly to move towards a first instrument position. In an aspect, the method further comprises the step of contacting the projection of the lever with the top surface of one of the first or second jaw portions of the grasper, while the jaw of the grasper moves towards the open jaw position to cause one of the first or second jaw portions to apply a force upon the projection to cause the lever to rotate about the fulcrum, while the projection simultaneously rides along the top surface of one of the first or second jaw portions to cause the instrument of the operative assembly to reach the first instrument position. In an aspect, the method further comprises the step of applying a force upon the lever using the jaw of the grasper to cause the lever to rotate about the fulcrum, while the lever rides along the actuation mating surface of one of the first or second jaw portions to cause the instrument of the operative assembly to move to a second instrument position that is relatively more closed than the first instrument position, while the projection of the lever simultaneously rides above the top surface of one of the first or second jaw portions of the grasper.

In an embodiment, the technology includes a surgical apparatus comprising, a grasper comprising a grasper housing having a distal end and a proximal end, the grasper housing defining a docking opening at the distal end, the docking opening having a shape, and a jaw at the distal end of the grasper housing, the jaw including a first jaw portion and a second jaw portion, at least one of the first or second jaw portions is movable relative to the other, and wherein the first and second jaw each comprise at least one actuation mating surface, and a robotic device operably coupled to the proximal end of the grasper housing and configured to actuate the first and second jaw portions of the grasper between a first position and a second position. In an implementation of the surgical apparatus, the first and second jaw portions of the grasper are configured to engage and actuate a tool. In an implementation of the surgical apparatus, the shape of the docking opening of the grasper housing is configured to mate with a tool having a tool housing comprising a proximal end and a distal end and an inner surface, the tool housing defines a docking assembly at the proximal end of the tool housing, the docking assembly comprises a first protrusion extending proximally from the proximal end of the tool housing and having a shape complementary to the docking opening of the grasper, and the first protrusion is configured to cooperate with the docking opening to constrain the tool in all axes relative to the grasper.

In an implementation of the surgical apparatus, at least one of the first and second jaw portions define a channel having a channel shape and configured to cooperate with a tool having a tool housing comprising a proximal end and a distal end and an inner surface, the tool housing defines a docking assembly at the proximal end of the tool housing, the docking assembly comprises a first protrusion extending proximally from the proximal end of the tool housing and having a first protrusion shape complementary to the docking opening of the grasper, and the docking assembly of the tool further comprises a second protrusion extending from the inner surface of the tool housing and having a second protrusion shape complementary to the channel shape. In an aspect of an implementation, the docking opening of the grasper housing is configured to cooperate with the first protrusion of the docking assembly of the tool, and the channel of the at least one of the first and second jaw portions of the grasper is configured to cooperate with the second protrusion of the docking assembly of the tool to constrain the tool in all axes relative to the grasper.

In an implementation of the surgical apparatus, the first jaw portion is fixed relative to the grasper housing and the second jaw portions is movable relative to the first jaw portion. In implementation of the surgical apparatus, the first and second jaw portions are independently movable.

In an implementation of the surgical apparatus, the first jaw portion comprises, an electrically conductive contact portion at a distal end of the jaw portion, an electrical conductor coupled to the conductive contact portion, and a proximal end comprising an electrical insulator. In an aspect of an implementation, the electrically conductive contact and the electrical conductor of the first jaw portion are configured to transfer an electrical current to a tool to electrify said tool.

In an implementation of the surgical apparatus, the first jaw portion is electrically conductive and is coupled to a first electrical conductor and the second jaw portion is electrically conductive and is coupled to a second electrical conductor. In an aspect of an implementation, the grasper housing is configured as an electrical insulator.

In an aspect of an implementation, the first and second jaw portions of the grasper each comprises a proximal end, the proximal end of both the first and second jaw portions are electrically insulated. In an aspect of an implementation, the first and second jaw portions of the grasper are configured to transfer an electrical current to a tool to electrify said tool.

In an implementation of the surgical apparatus, at least one of the first and second jaw portions of the grasper comprises a force-open channel having a force-open channel shape complementary to a projection of a lever of a tool, and the at least one of the first and second jaw portions having the force-open channel further comprises a top surface. In an aspect of an implementation, the force-open channel is configured to allow the projection of the lever of the tool to pass through the channel to allow the projection to rest above the top surface of the at least one of the first and second jaw portions having the force-open channel and said top surface is configured to apply a force upon the projection of the lever of the tool to cause the tool to move to a first tool position.

BRIEF DESCRIPTION OF FIGURES

Note that numbered items remain consistent across all figures. Items numbered with the same number are either the same item, or identical copies of the item. Items numbered with different numbers are either parts of different design, or are occasionally identical parts serving different purposes.

FIG. 2A is a top profile view of the tool hull according to one embodiment.

FIG. 2B is a top exploded view of the tool hull according to one embodiment.

FIG. 2C is a rear profile view of the tool hull according to one embodiment.

FIG. 2D is a rear exploded view of the tool hull according to one embodiment.

FIG. 59B is a side profile view of a universal grasper with jaws having attachment channels, in a closed position according to one embodiment.

FIG. 60A is a side profile view of an embodiment of a universal grasper with attachment channels prior to mating with a tool with attachment appendages containing attachment pins, according to one embodiment.

FIG. 60B is a side profile view of an embodiment of a universal grasper with attachment channels illustrating initial mating with a tool with attachment appendages containing attachment pins, according to one embodiment.

FIG. 60C is a side profile view of an embodiment of a universal grasper with attachment channels after mating with a tool with attachment appendages containing attachment pins, according to one embodiment.

FIG. 61A is a side profile view of an embodiment of a universal grasper with attachment channels illustrating initial actuation of an embodiment of a tool with attachment appendages containing attachment pins, according to one embodiment.

FIG. 61B is a side profile view of an embodiment of a universal grasper with attachment channels illustrating actuation of an embodiment of a tool with attachment appendages containing attachment pins, according to one embodiment.

FIG. 61C is a side profile view of an embodiment of a universal grasper with attachment channels illustrating actuation of an embodiment of a tool with attachment appendages containing attachment pins, according to one embodiment.

DETAILED DESCRIPTION

Figure 1A:
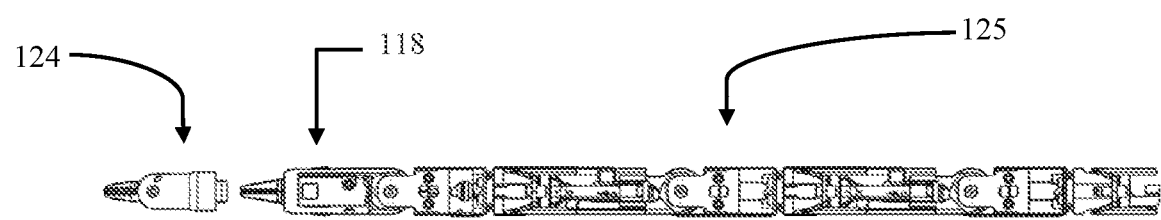
FIG. 1A is a left profile view of one embodiment of a robotic arm prior to coupling with a tool.

While the present system is designed for use by a surgeon within the abdominal cavity, many alternative uses of the device are possible. For example, a user might be a physician assistant, nurse, surgical aid, or any other surgical personnel. Additionally, the device could be disposed within any part of a patient's body, and future embodiments could be designed to be much smaller so as to allow for use within smaller areas of a patient's body. Both smaller and larger devices can be fabricated for use in areas such as the paranasal sinuses, colon, stomach, or any other areas within the human body including but not limited to, the abdomen, cranium and cervicis. Micro-fabrication using MEMS or other means could allow for a device to be positionable within immensely small areas such as human blood vessels.

In other embodiments, the device may be used for non-surgical or non-medical tasks such as micro-fabrication, assembly of parts, bomb defusing, industrial manufacturing, or any other task requiring the use of multiple tools and fine motor skills. Alternative embodiments of the device could be fabricated to be human-sized or even larger-than-life allowing humans to perform tasks, which they are too small, too weak, or otherwise unable. Obviously, in such embodiments, the user may not necessarily be a surgeon.

Overview

The surgical apparatus system disclosed herein has been designed to be incorporated and utilized with the Virtual Reality Surgical Device disclosed in International Patent Application No. PCT/US2015/02926 (published as International Patent Application No. WO2015171614A1), included in the attached appendix and incorporated by reference in its entirety herein. Notwithstanding the above sentence, in other embodiments the surgical apparatus system disclosed herein can be implemented and utilized by other existing robotic surgery systems and/or devices.

The purpose of the system is to allow a surgeon who is performing surgery utilizing the Virtual Reality Surgical Device to be able to interchange between different types of surgical tools and instruments without having to remove the robotic arm from the surgical site and manually switch and attach different surgical tools. The system allows a surgeon to select and use a desired tool using the robotic arm of the Virtual Reality Surgical Device, the same way a person would use his or her own hand to pick up an object in normal every day life, thus allowing a surgeon to remain completely immersed in virtual reality while utilizing the Virtual Reality Surgical Device.

The system disclosed provides numerous advantages for surgeons, as it allows a surgeon to interact with the in vivo robotic device as if the device were the surgeon's own arms and hands. This allows a surgeon to perform very difficult and delicate procedures in close quarters, while allowing a surgeon to maintain the natural motions to which he or she is accustomed when performing a procedure. With the system a surgeon is able to perform an operation in the manner and form in which he or she is accustomed, while being able to access areas of the body that would not otherwise be accessible using other robotic devices. Additionally, with the system a surgeon is able to switch between different tools and instruments at his or her own free will, without having to remove the entire surgical device to enact the exchange between tools and/or instruments. This allows a surgeon to perform numerous complex procedures without undue delay, thus decreasing the time it takes to perform a procedure and allowing a patient to commence their recovery sooner.

In addition, the system reduces the number of incisions necessary for an operation to be performed. A reduction in the number of incisions provides an immense benefit to a patient's health and recovery, as the risk of infection and size and number of surgical wounds are decreased. As the tools and instruments of the system can be introduced into a patient through the same incision as the robotic device and also remain in close proximity to a surgical site inside of the patient, a surgeon is able to interchange between different tools and instruments with ease without removal of the device. This helps to reduce the operation time, reduce the need to reposition the robotic device at the surgical site and also helps a surgeon concentrate on performing a surgery, thus improving his or her productivity.

The surgical apparatus system also allows the surgeon access to an extensive collection of surgical tools and instruments, while utilizing only one device, thus bestowing a surgeon with the ability to perform numerous procedures without having to purchase or utilize multiple robotic devices.

Unless otherwise stated, the term "distal" as used herein means relatively further from a reference point, while "proximal" means relatively closer to a reference point. In general, the reference point will be the operator of the object being described.

Figure 1B:
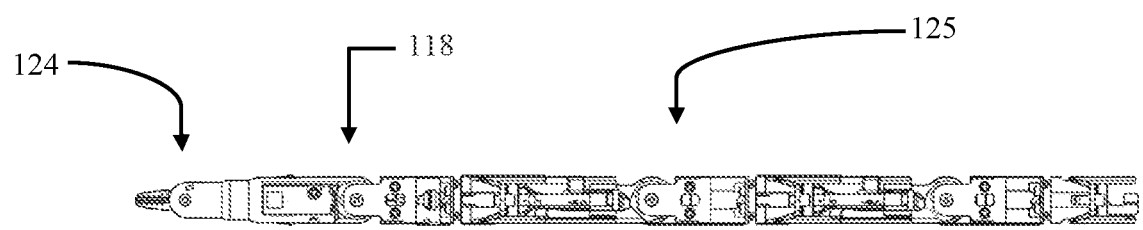
FIG. 1B is a left profile view of one embodiment of a robotic arm coupled with a tool.

FIG. 1A shows a side view of one embodiment of the system prior to attachment with a tool. FIG. 1B gives an illustration of one embodiment of the system after a tool has been attached. According to one embodiment the system consists of a tool 124 which is housed by a tool hull or housing 100, where the tool hull 100 interfaces with the universal grasper 118 of a robotic arm 125, thus allowing the operator to select and engage an array of tools by simply picking up the tool with said universal grasper 118.

FIG. 2A-2D show multiple views of one embodiment of the tool hull 100. The tool hull 100 is an essential part to the overall surgical apparatus system, as it performs crucial functions. The tool hull 100 functions as a housing for the tool and/or instrument. In addition, the tool hull 100 provides key mating and/or attachment functions. Moreover, the tool hull 100 provides constraint and stability to the overall system, by preventing parts of the system from moving and detaching from other components. In some embodiments, the tool hull 100 has a proximal end and distal end. In some embodiments, the proximal end of the tool hull 100 forms a docking assembly, with said assembly providing key mating and/or attachment features, such as a docking tab(s) or protrusion(s) 103 and a tool attachment pin(s) or protrusion(s) 102. In some embodiments, the distal end of a tool hull 100 forms an operative assembly which encompasses key tool and/or instrument features and elements, such as a fulcrum(s) 108, a tool actuation lever(s) 109, and/or an actuator 111.

In one embodiment, the tool hull 100 is fabricated out of two bodies or tool housing segments 107, a left and right body, which mate with one another forming an inner surface and a housing for a tool and/or instrument. As used herein, the terms "left" and "right" are arbitrary terms employed for convenience only. These terms are not intended to convey any preferred orientation, function, or structure, or to suggest any intrinsic difference or similarity between the bodies or tool housing segments of the tool hull, or any other components referred herein as "left" and "right" components. While certain differences may be noted below, these are provided only by way of exemplary embodiments and are not intended to limit the meaning of the terms "left" and "right" as described above. Similarly, terms such as "top" and "back" are provided for convenience only, and are not intended to convey any specific orientation, function, or structure unless explicitly noted to the contrary or otherwise clear from the context.

In one embodiment, the bodies or tool housing segments 107 of the tool hull or housing 100 are identical and symmetrically orientated relative to one another. In a different embodiment, the tool hull 100 consists of two bodies or tool housing segments, which may be asymmetric or different. In further embodiments, the tool hull 100 is fabricated as one solid body consisting of two sides. The tool hull 100 is constructed out of biocompatible materials including but not limited to metals, plastics, ceramics and/or other materials known to those in the art. In some embodiments, the tool hull 100 is constructed of biocompatible metals including but not limited to surgical stainless steel or titanium. In other embodiments, the tool hull 100 is constructed of biocompatible plastics including but not limited to polyvinylchloride (PVC), polyethersulfore (PES), polyetheretherketone (PEEK), polysulfone (PS) or other biocompatible plastics known by those in the field. Furthermore, other embodiments may be constructed of biocompatible ceramics such as aluminum oxide ($Al_2O_3$) and/or other biocompatible ceramics known by those in the field.

In one embodiment, the bodies or segments 107 of the tool hull 100 affix to each other by a top support bar 104 and a bottom support bar 105. In some embodiments, the top support bar 104 is affixed to the right body 107 of the tool hull 100 and the bottom support bar is affixed to the left body 107 of the tool hull 100 as illustrated in FIG. 2B. In other embodiments, the top support bar 104 is affixed to the left body 107 of the tool hull 100 and the bottom support bar is affixed to the right body 107 of the tool hull 100. In some embodiments, the top support bar 104 and bottom support bar 105 are located at the distal end of the bodies 107 of the tool hull. In other embodiments, the top support bar 104 and bottom support bar 105 are located at the proximal end of the bodies 107 of the tool hull 100. The top support bar 104 and bottom support bar 105 provide stability to the tool hull 100, by preventing deflection, torsion and flexure of the bodies 107 of the tool hull 100.

Figure 3A:
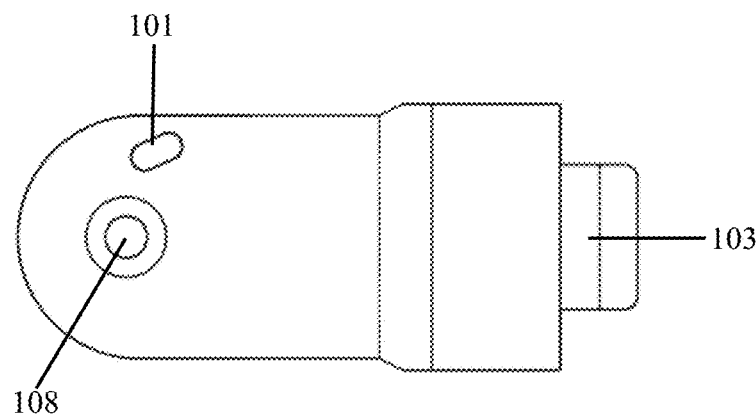
FIG. 3A is a left profile view of the tool hull according to one embodiment.
Figure 3B:
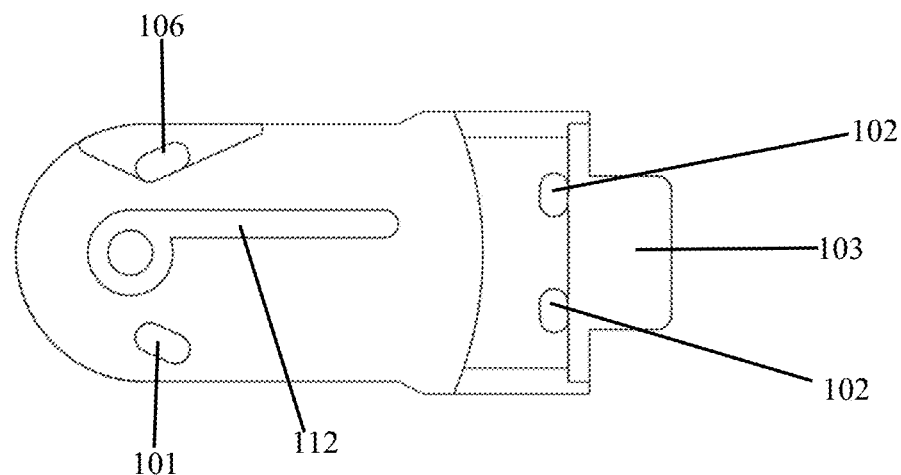
FIG. 3B is a cutaway view of the right side of a tool hull according to one embodiment.

In one embodiment, each support bar contains a pin 106 that fits into a corresponding pinhole 101 located on the opposite body of the tool hull 100 as depicted in the embodiments shown in FIG. 2B and FIG. 3B. In some embodiments press fits and snaps are used instead of pins. In other embodiments, the pinhole connection is substituted for a welded connection, magnetic connection, adhesive connection and/or any other method or combination of methods known in the art. The pinhole connection along with the support bars help to support and stabilize a tool when it is being utilized. In addition, the pinhole connection helps to prevent deflection, torsion and flexure of the bodies 107 of the tool hull 100. Alternatively, some embodiments of the tool hull 100 do not contain a top support bar 104 and/or a bottom support bar 105. In these embodiments, the tool hull 100 may be fabricated as one solid body, thus eliminating the concern of separation of the bodies or segments 107.

Figure 21A:
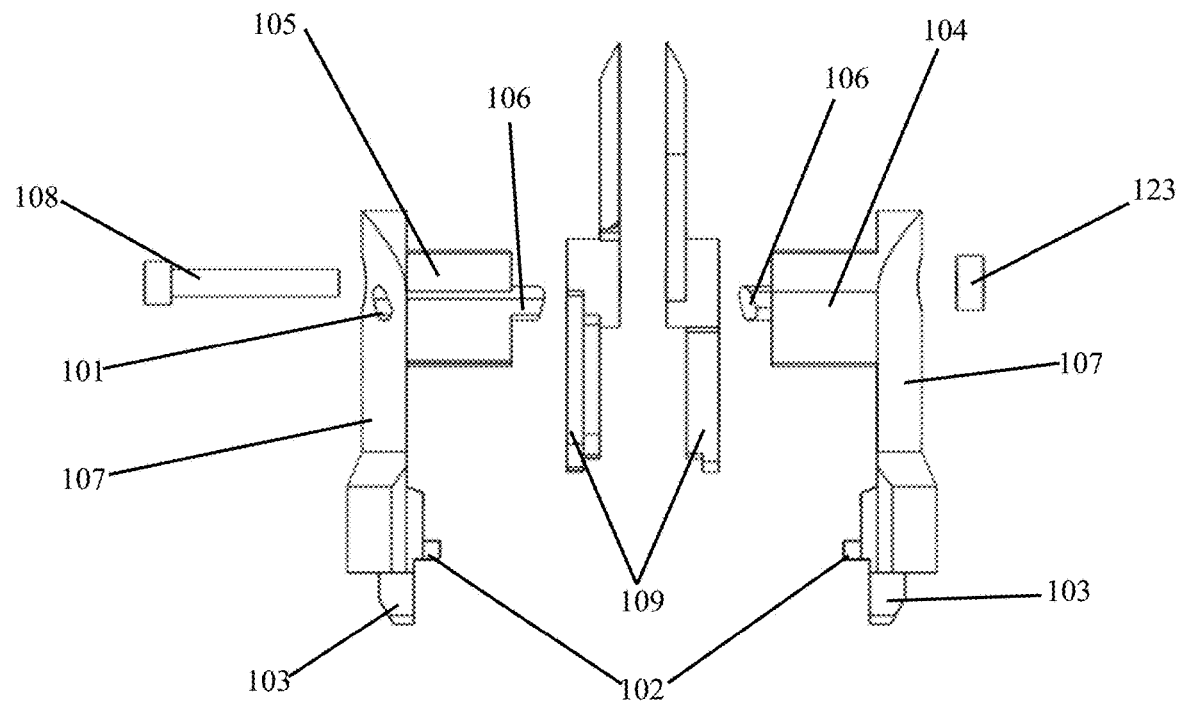
FIG. 21A is a top exploded view of a scissor tool according to one embodiment.
Figure 21B:
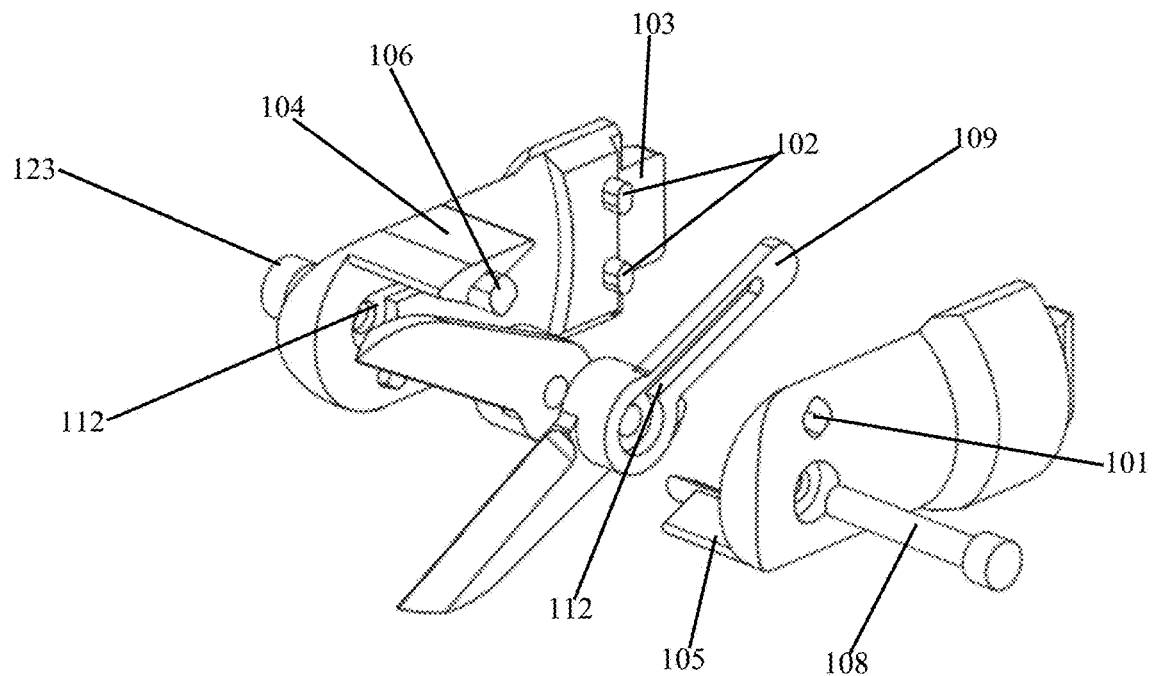
FIG. 21B is a diagonal exploded isometric view of a scissor tool according to one embodiment.

Additionally, in some embodiments the bodies or segments 107 of the tool hull 100 are also affixed to one another via a fulcrum 108 and nut 123 connection as illustrated in the embodiment shown in FIG. 21A. In one embodiment, the fulcrum 108 passes through an opening in the left body of a tool hull 100 through apertures 110 in the middle of tool actuation levers 109 and through an opening in the right body of a tool hull 100 where the fulcrum 108 connects to a nut 123. In other embodiments, the fulcrum 108 passes through the right body of a tool hull 100 then through the apertures 110 of tool actuation levers 109 and through the left body of a tool hull 100 where it is met by a nut 123. The fulcrum 108 can be connected and fastened in any method or combination of methods known in the art, including but not limited to, a tapped connection, a welded connection, an adhesive connection and/or riveting. The fulcrum 108 can take on a variety of configurations and shapes that allow the bodies 107 of a tool hull to be affixed to one another, as well as act as a pivoting point for tools containing tool actuation levers 109 as detailed below. In some embodiments, the fulcrum 108 is configured as a rod, while in other embodiments the fulcrum 108 is configured as a screw. In further embodiments, the fulcrum 108 is configured as a pin.

In addition to affixing the bodies of the tool hull 100, the fulcrum 108 also constrains the tool actuation levers 109 in place and prevents the tool hull 100 from experiencing any torsional movements or deflection, while a tool is being utilized. Furthermore, in some embodiments the fulcrum 108 serves as a pivoting point for tools and/or instruments containing a tool actuation lever or levers 109, such as scissors, needle driver or forceps. In some embodiments, the fulcrum 108 is fabricated out of any biocompatible metal that is capable of handling the stress and strain from the actuation of a tool. In other embodiments, the fulcrum 108 is fabricated out of biocompatible plastics capable of handling the stress and strain from the actuation of a tool. In alternative embodiments, the fulcrum 108 is constructed out of biocompatible ceramics such as aluminum oxide ($Al_2O_3$) and/or other biocompatible ceramics known by those in the field capable of handling the stress and strain from the actuation of a tool. In addition, in different embodiments the fulcrum 108 can be fabricated in any shape known in the art that is capable of serving as a pivoting point, while being able to handle the strain and stress forces generated by the actuation of a tool and/or instrument.

In other embodiments, the fulcrum 108 is not required. In these embodiments, the tool hull 100 may be fabricated as one solid body, thus relieving any concern of separation. Alternatively, in embodiments where the tool or instrument is a static tool and does not contain a tool actuation lever 109 such as a cautery hook or single blade tool, no fulcrum 108 may be found, as no pivot point is required to actuate and/or utilize the tool. Alternatively, in additional embodiments multiple fulcrums 108 are found, with each tool actuation lever 109 of a tool being operably coupled to a separate and distinct fulcrum 108. In these embodiments, an operator can pivot a tool actuation lever 109 about a fulcrum 108 to a specific orientation without having to pivot the other tool actuation lever 109 to the same orientation, thus providing a tool that has levers that can be actuated independently of the other.

Figure 3C:
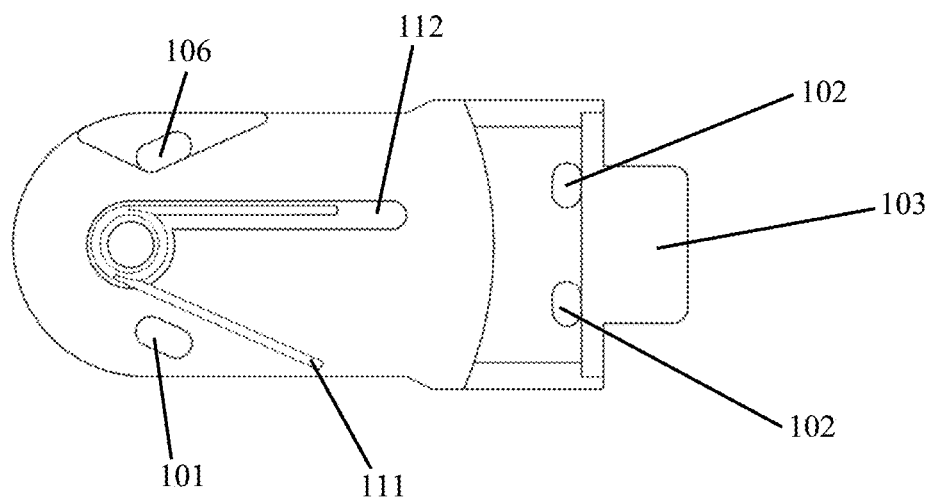
FIG. 3C is a cutaway view of the right side of a tool hull illustrating the actuator of the device according to one embodiment.
Figure 4A:
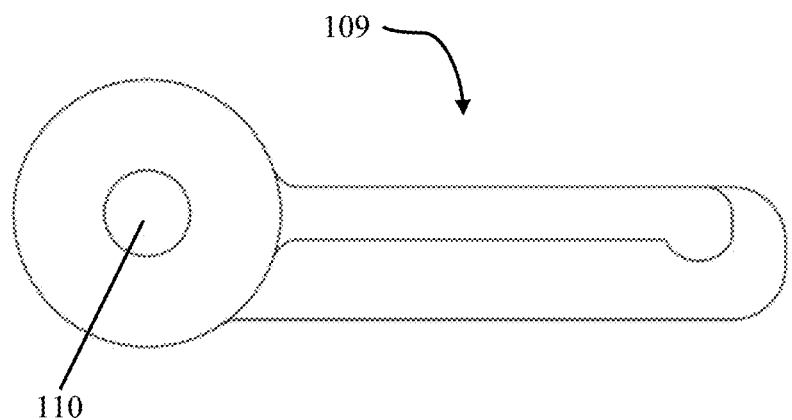
FIG. 4A is a left profile view of a right tool actuation lever according to one embodiment.
Figure 4B:
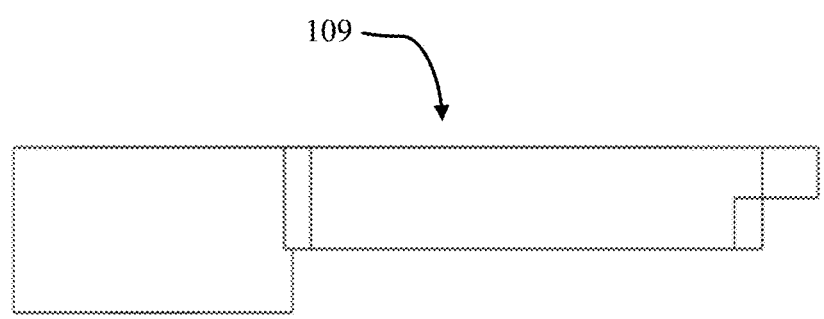
FIG. 4B is a top profile view of a right tool actuation lever according to one embodiment.
Figure 4C:
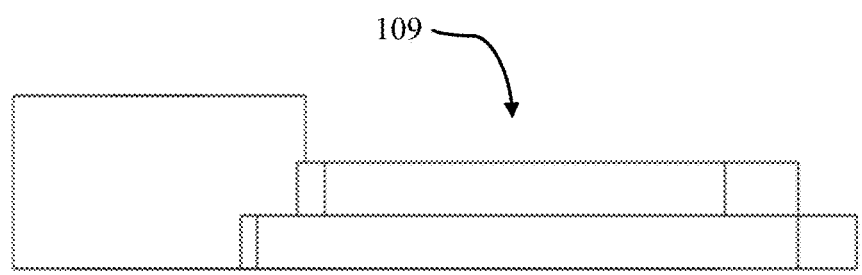
FIG. 4C is a top profile view of a left tool actuation lever according to one embodiment.
Figure 4D:
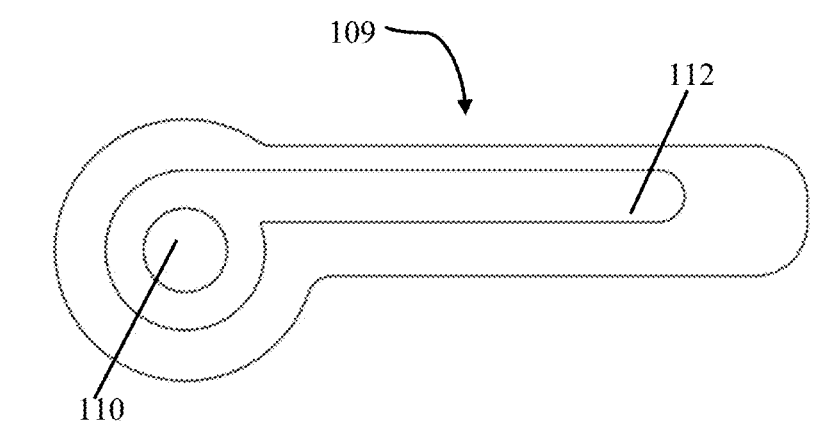
FIG. 4D is a left profile view of a left tool actuation lever according to one embodiment.

In addition, in some embodiments the device contains a plurality of actuation channels 112 as illustrated in the embodiments shown in FIG. 3B and FIG. 4D. Actuation channels 112 serve as a housing for the actuator 111 of the tool and/or instrument. FIG. 3C illustrates the location of the actuator 111 in one embodiment of the tool hull 100. The actuator 111 can be any mechanical actuation component or combination of components known in the art such as a torsion spring, a leaf spring, a cable or any other existing mechanical actuation component capable of actuating a tool and/or instrument. The actuator 111 allows the universal grasper jaws to interact with tool actuation levers 109, resulting in a tool being capable of moving between multiple positions, such as a first, second and/or third position, with said positions including but not limited to an open, partial open/closed position and/or closed position. The actuator 111 provides a force on a tool actuation lever 109 when a universal grasper jaw presses upon said lever, thus allowing the universal grasper jaw to maintain constant contact with the lever while the tool is being utilized. Additionally, the actuator is configured to retain an energy from the force applied by the jaw of a universal grasper when it presses on a lever, as well as configured to release the energy retained upon the lever during actuation of a tool. In one embodiment, the actuator 111 is held in the actuation channel 112 by way of the tool actuation lever 109. In this embodiment, the tool actuation lever 109 is positioned in such a way that there is minimal space between the tool actuation lever 109 and the actuator 111 thus retaining the actuator 111 in the actuation channel 112. In other embodiments, the actuator 111 is retained in the actuation channel 112 via an adhesive connection and/or a welded connection.

In some embodiments actuation channels 112 are located on both the inner portions of the left and right bodies 107 of a tool hull 100, as well as located on the tool actuation levers 109 as depicted in the embodiments shown in FIG. 3B and FIG. 4D. This embodiment is used for actuated tools and/or instruments containing two tool actuation levers 109 with one lever having a first instrument component affixed to the distal end of the lever and the other lever having a second instrument component affixed to the distal end of the lever. In these embodiments, the first instrument component and the second instrument component combine to form the tool, for example two blades for scissors or two needle driver jaws for a needle driver. Other examples of such tools and/or instruments may also include but are not limited to, scissors, needle grasper, forceps, graspers, retractors, surgical stapler and/or caliper. In this embodiment two actuators 111 are needed, one actuator 111 for the right tool actuation lever 109 and one for the left tool actuation lever 109. In this embodiment one end of an actuator 111 is contained in an actuation channel 112 of a tool actuation lever 109 and the other end of the actuator 111 is fed through the actuation channel 112 located on the body of the tool hull 100. As such, in this embodiment the actuator 111 that is contained in the actuation channel 112 of the left tool actuation lever 109 is fed into the actuation channel 112 located on the left body 107 of the tool hull 100. The same method is used for the actuator 111 contained in the actuation channel 112 of the right tool actuation lever 109.

In other embodiments, only one actuation channel 112 is situated on one of the bodies 107 of the tool hull 100 and only one actuation channel 112 is found in one tool actuation lever 109. In this embodiment, the tool or instrument may contain only one actuated lever, with a first instrument component affixed to the distal end of said actuated lever, and a second instrument component of the tool being rigidly fixed to the tool hull 100. An example of such a tool may include but is not limited to a surgical stapler or a vessel sealer. Furthermore, only one actuator 111 may be found in this embodiment, as only one component of the tool and/or instrument may be capable of moving. In other embodiments, one component of a tool may be moved by an actuator 111 and other moving component of the tool may be mechanically coupled to the first moving component such that only one tool actuation lever 109 is directly coupled to the actuator 111, thus allowing for multiple tool actuation levers 109 to be actuated by one actuator 111. The mechanical coupling may be accomplished via gears, links and/or any other methods known in the art.

Additionally, in alternative embodiments no actuation channels 112 and/or actuators 111 may be found. In some embodiments, the tool and/or instrument may not contain a tool actuation lever 109. In some embodiments, the tool may be rigidly affixed to the tool hull 100 and not capable of moving in any direction, such as a cautery hook or a scalpel.

FIG. 4A-FIG. 4D show multiple views of one embodiment of a tool actuation lever 109. In one embodiment, the left and right tool actuation levers 109 can be interchanged, as they are identical but oriented symmetrically. In other embodiments, the left and right tool actuation levers 109 are not identical, as the right and left tool actuation levers 109 may differ in length and/or width. The tool actuation lever 109 serves multiple purposes as it contains an actuation channel 112 which houses the actuator 111, is used to actuate a tool and/or instrument and acts as a support for a tool and/or instrument. In addition, affixed to the distal end of the tool actuation levers 109 are the components of a tool or instrument. In some embodiments, the first instrument or tool component of a tool is affixed to the right tool actuation lever 109 and the second instrument or tool component of a tool is affixed to the left tool actuation lever 109. In other embodiments, the tool actuation levers 109 are mirrored such that affixed to the right tool actuation lever 109 is the first instrument component of a tool and affixed to the left tool actuation lever 109 is the second instrument component of a tool.

In one embodiment, a tool contains two tool actuation levers 109. In this embodiment located at one end of the tool actuation levers 109 is an aperture 110 in which the fulcrum 108 passes through, as shown by the illustrative embodiment in FIG. 21A. As stated above, in this embodiment the fulcrum 108 acts as a pivot point for the tool and/or instrument, which allows the levers to pivot thus letting the tool and/or instrument to move between a first and second position.

Figure 5:
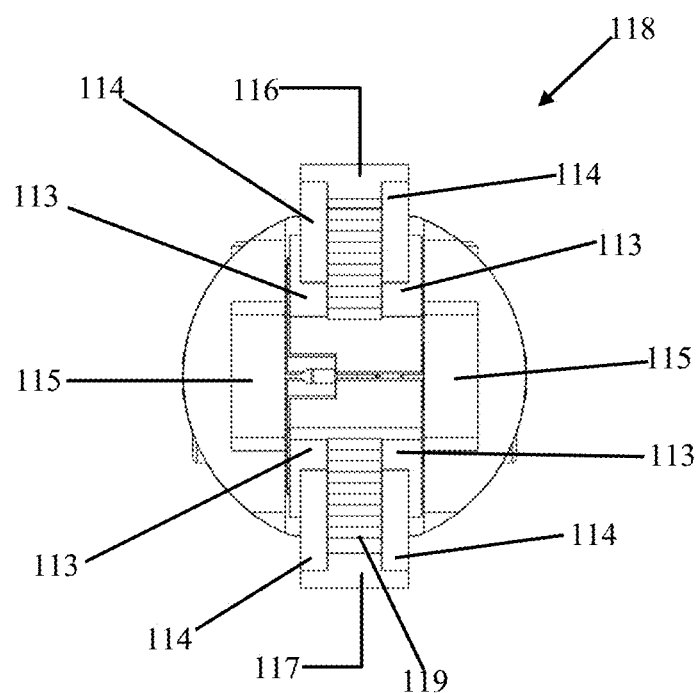
FIG. 5 is a front profile view of the universal grasper according to one embodiment.
Figure 6:
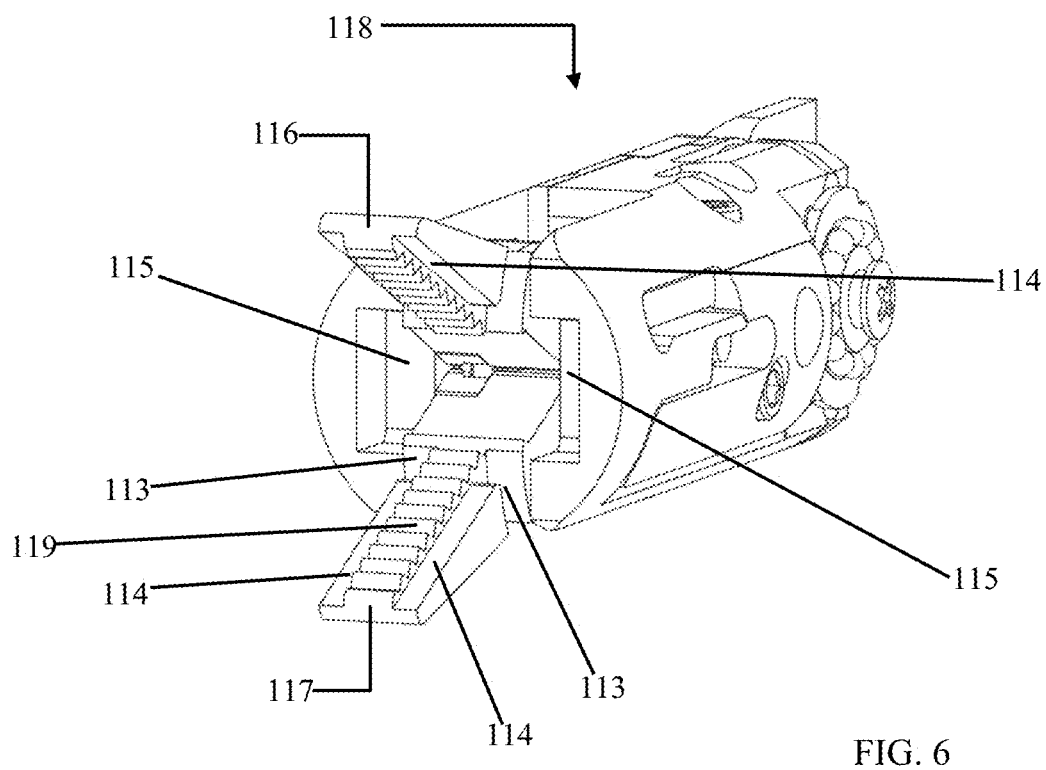
FIG. 6 is a diagonal isometric view of the universal grasper according to one embodiment.

In some embodiments, located on the proximal end of the right and left bodies 107 of the tool hull 100 are tool attachment pins or protrusions ("TAPs") 102 as depicted in the embodiments shown in FIG. 2A-2D. The TAPs 102, which are also referred to as second protrusions, interface with the jaws of the universal grasper 118 (FIG. 5 and FIG. 6). In some embodiments, this interface is effectuated via tool attachment pin channels 113 located at proximal end of the universal grasper jaws and prevents the tool hull from separating from the universal grasper 118 during actuation. FIG. 5 and FIG. 6 depict an illustrative embodiment of the universal grasper 118.

In one embodiment, each body 107 of the tool hull 100 contains two TAPs 102 with one TAP 102 located above the other. In this embodiment, both TAPs 102 are vertically aligned with each other. Additionally, in this embodiment the TAPs 102 are separated by a vertical distance, which is correlated to the vertical distance between the tool attachment pin channel 113 of the first grasper jaw 116 and the tool attachment pin channel 113 of the second grasper jaw 117 (FIG. 5 and FIG. 6) when the jaws are in a fully open state. The vertical distance between the TAPs 102 must be less than the vertical distance between the tool attachment pin channels 113 on the grasper jaws, so as to allow the TAPs 102 to enter and couple with the tool attachment pin channels 113. In other embodiments only one TAP 102 is located on each body 107 of the tool hull 100. In alternative embodiments, no TAPs 102 may be found. Thus, in some embodiments, anywhere from zero to four TAPs 102 may be found on the proximal end of a tool hull 100. Furthermore, in other embodiments more than four TAPs 102 are located on proximal end of a tool hull 100.

Figure 15A:
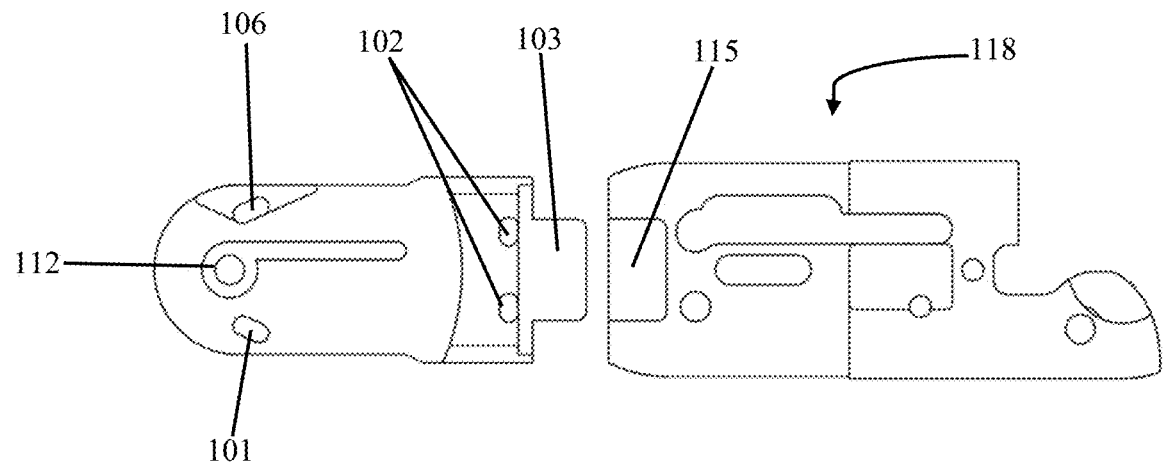
FIG. 15A is a cutaway view of the right side of a tool hull and the main body of a universal grasper prior to mating according to one embodiment.
Figure 15B:
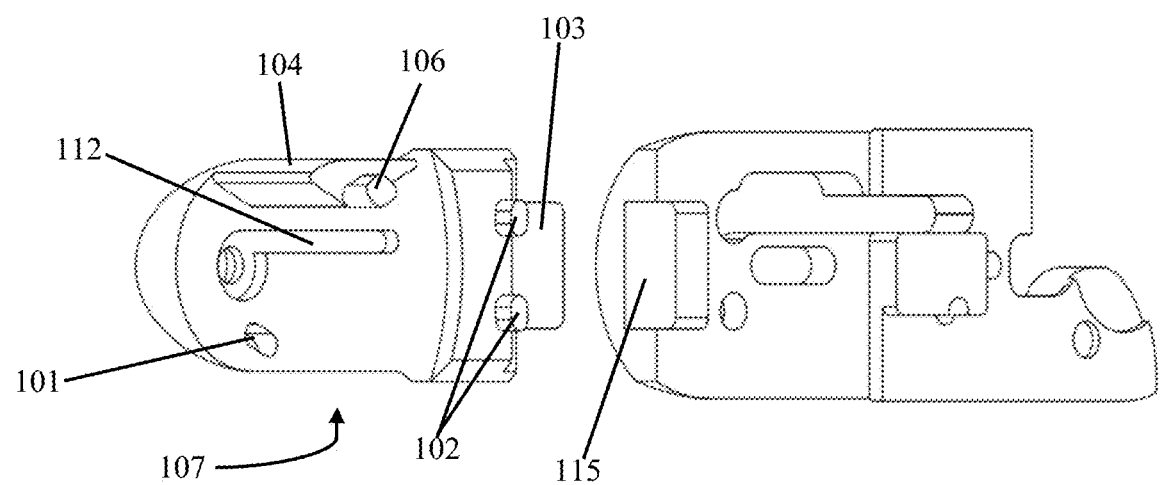
FIG. 15B is an isometric cutaway view of the right side of a tool hull and the main body of a universal grasper prior to mating according to one embodiment.
Figure 16A:
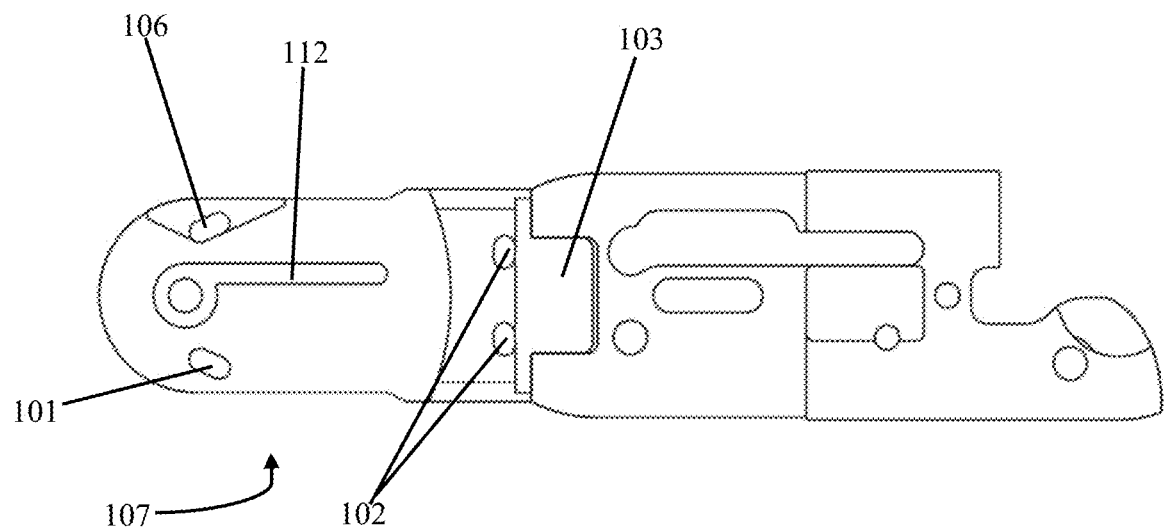
FIG. 16A is a cutaway view of the right side of a tool hull and the main body of a universal grasper when mated according to one embodiment.
Figure 16B:
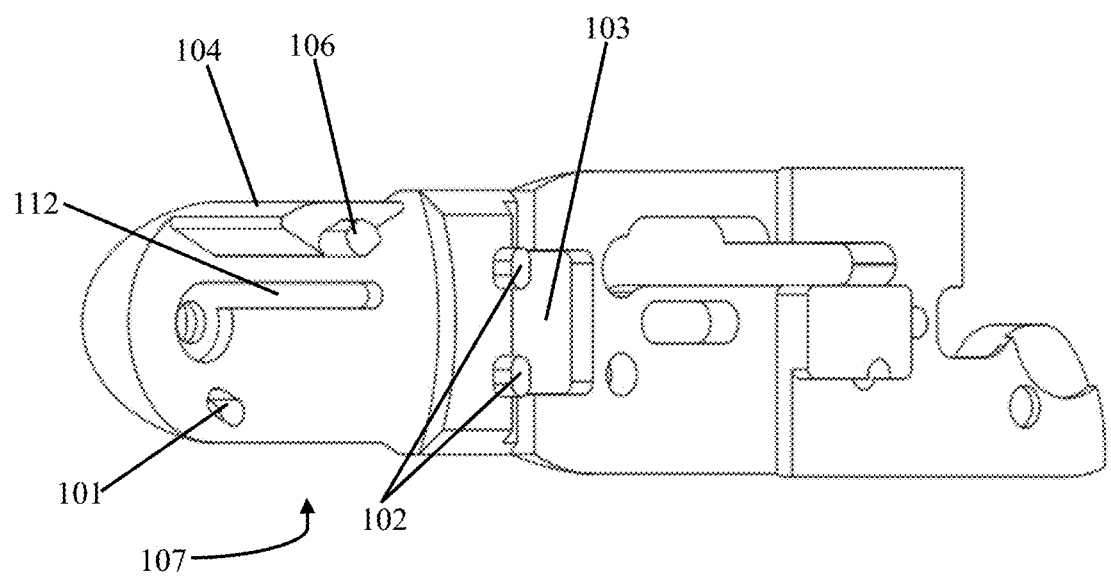
FIG. 16B is an isometric cutaway view of the right side of a tool hull and the main body of a universal grasper when mated according to one embodiment.

In addition, in some embodiments, located at the proximal end of each body 107 of the tool hull 100 is a docking tab or first protrusion 103. FIG. 2B and FIG. 3A-3C depict embodiments of tool hulls 100 containing docking tabs 103. In some embodiments, the docking tabs 103 are fed into the universal grasper 118 when the grasper jaws are in an open position and connect to their respective docking stations or openings 115 as depicted in the embodiments shown in FIG. 15B and FIG. 16A. The docking tabs or first protrusions 103 are used to connect the tool hull 100 to the universal grasper 118 so as to prevent the tool hull 100 from detaching from the universal grasper 118. In addition, the docking tabs 103 also prevent torsion and tilting and provide added stability to the tool hull 100 during actuation of a tool and/or instrument. The docking tabs 103 can take on a variety of shapes and configurations in different embodiments that allow them to connect and interface with the docking stations 115 of the universal grasper 118. The connection can be fashioned via any standard attachment method known to those in the field. In some embodiments, the docking tabs 103 may be replaced by a number of pins, which connect to a number of docking stations. In other embodiments, a hook and loop latch connection may be used.

In alternative embodiments, docking tabs or first protrusions 103 are eliminated and replaced by magnets, electromagnets, press fits and/or any other method or combination of methods known in the art. In one embodiment that utilizes a magnet or electromagnet in place of a docking tab 103 to connect to the universal grasper 118, the need for TAPs 102 is eliminated, as the force generated by the magnet or electromagnet connection is sufficient to mate the tool hull 100 with the universal grasper 118, and prevent the tool hull from separating from the universal grasper 118, as well as preventing the tool hull 100 from tilting, twisting or deflecting during actuation. In this embodiment, the docking stations 115 consists of a ferromagnetic material or other conductive material with a high permeability, such as iron, or nickel. In alternative embodiments, the docking tabs 103 may be fabricated out of ferromagnetic material and the electromagnet are located on the docking stations 115. In these embodiments, the ferromagnetic material and magnetic material have biocompatible coatings and/or platings, including but not limited to gold plating, rendering the material safe for insertion into a patient's body. However, in some embodiments the docking tabs or first protrusions 103 are not eliminated, but are outfitted with a magnetic contact and the docking stations or openings 115 are outfitted with a corresponding magnetic contact. In these embodiments, the magnetic contact located on the docking tabs 103 mates and contacts with the magnetic contact of the docking stations or opening 115 to constrain a tool hull to a universal grasper.

In an alternative embodiment, docking tabs or first protrusions 103 are capable of conducting an electrical current from the universal grasper 118. This embodiment allows a surgeon to utilize electrified tools such as a cautery tool. In addition, this embodiment also allows for electrical powered tools to be used. In one embodiment, docking tabs 103 are constructed of a biocompatible material capable of conducting and transferring an electrical current or power, such as surgical stainless steel. In this embodiment, the docking tabs 103 are appropriately insolated such that they do not electrically short. In other embodiments, the docking tabs 103 may contain an electrical conductive contact on the proximal end that is capable of conducting electricity from a universal grasper 118. These embodiments allow an electrical current or power to be transferred through the docking tabs 103 to a tool, thus allowing the tool to be electrified. In alternative embodiments, tools may be powered and actuated via the electrical current or power that is transferred through the docking tabs 103. The docking tabs 103 and the electrical conductive contacts on the docking tabs 103 in these embodiments are appropriately electrically isolated such that no electrical short is experienced. In these embodiments, the docking stations 115 detailed below, contain an electrical port which the electrical conductive contact on the docking tabs or first protrusions 103 mates with, allowing an electrical current or power to be transferred from the universal grasper 118 to the tool. In these embodiments, the walls of the docking stations 115 surrounding the electrical ports are fabricated out of electrical insulation materials having a high surface resistivity such as polyimide, PEEK, acrylonitrile butadiene styrene (ABS), rubber and/or any other material with a high surface resistivity known in the art, thus preventing an electrical short from occurring. In some embodiments, the electrical current or power is routed to an electrical port via an insulated wire or conductor, a flexible printed circuit board ("FPCB") and/or a printed circuit board ("PCB").

Additionally, in alternative embodiments, the electrical port also acts as a sensor notifying a surgeon and the robotic system when a tool is engaged and/or disengaged. In some embodiments, the surgeon is notified via a PCB and/or FPCB when an electrical contact on a docking tab 103 interfaces with an electrical port. In other embodiments, a sensor is contained on the proximal end of the docking tabs 103 which notifies a surgeon and the robotic system when the docking tabs 103 connect and/or disconnect from the docking station 115. In further embodiments, the docking stations 115 contain a sensor, which notifies a surgeon and the robotic system when a tool is engaged and/or disengaged. A variety of sensors could be used in different embodiments to detect engagement and disengagement of a tool and/or the docking tabs 103, such as encoders, potentiometers, and/or any other sensors known to those in the field.

In alternative embodiments, the electrical port is configured to transmit electrical communication from the robotic arm to the tool, and/or from the tool to the robotic arm. In some embodiments, the electrical communication is transmitted in analog format, while in other embodiments the electrical communication is transmitted in digital format. In other embodiments, electrical contacts located on the jaws of the grasper and electrical contacts on the lever(s) of a tool are used to transmit electrical communications from the robotic arm to a tool or from the tool to the robotic arm. Such electrical communication may contain a variety of information and data including but not limited to, the status of a tool, force sensing data, engagement and disengagement statuses, actuation commands, faults and/or position and orientation information of a tool and/or instrument.

Universal Grasper Design and Components

As mentioned above, the system allows a surgeon or operator to select and interface with and change between different tools and/or instruments. In order for a surgeon to switch between different tools and/or instruments, a surgeon uses the universal grasper 118 to mate and couple with a tool and/or instrument. The universal grasper 118 is located at the distal end of an embodiment of the robotic arm 125 (FIG. 1B) disclosed in International Patent Application No. PCT/US2015/029246 (published as International Patent Publication No. WO2015171614A1). An illustrative version of the robotic arm 125 utilized with the system is shown in FIG. 1B, and it should be appreciated that other robotic devices can be utilized with the system. FIG. 6 shows an isometric view of one embodiment of the universal grasper 118. The universal grasper 118 is constructed to take on a variety of tool configurations in different embodiments.

In one embodiment, the universal grasper 118 is configured as a cautery tool, allowing a surgeon to perform cautery functions, while also allowing the surgeon to interchange between different tools if he or she desires. In some embodiments where the universal grasper 118 is configured as a cautery tool, the universal grasper 118 uses the monopolar cauterization method, while in alternative embodiments the universal grasper 118 uses the bipolar cauterization method. In embodiments where the universal grasper 118 is configured as a cautery tool the surgeon can activate and deactivate the electrical current or power provided to the universal grasper jaw, thus allowing the grasper jaws to switch between an electrically charged state and an uncharged state.

Figure 38A:
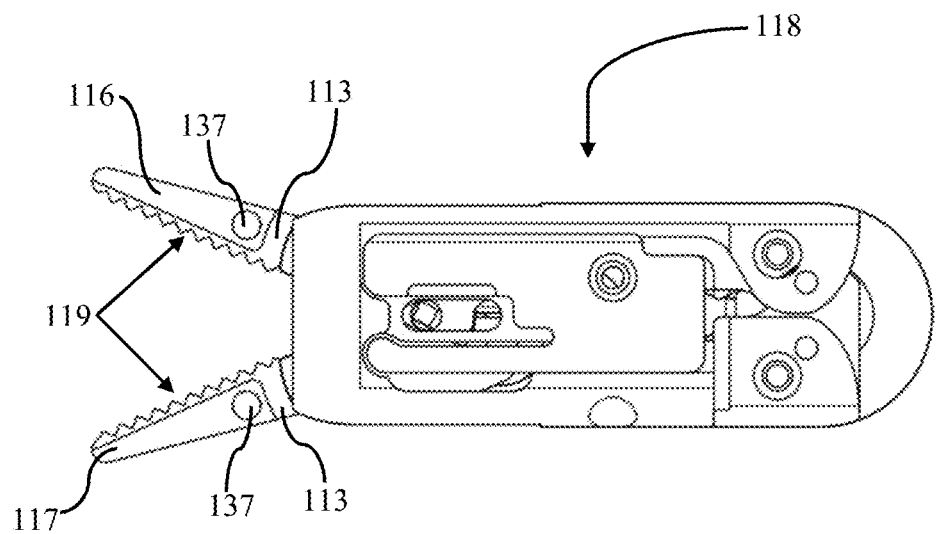
FIG. 38A is a side profile view of a universal grasper with an electrified jaw according to one embodiment.
Figure 38B:
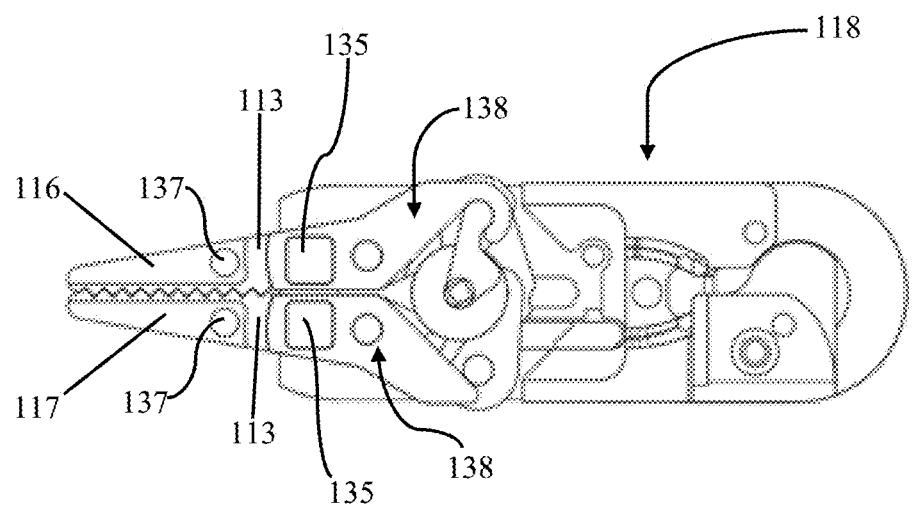
FIG. 38B is a cutaway side profile view of a universal grasper with an electrified jaw according to one embodiment.
Figure 39A:
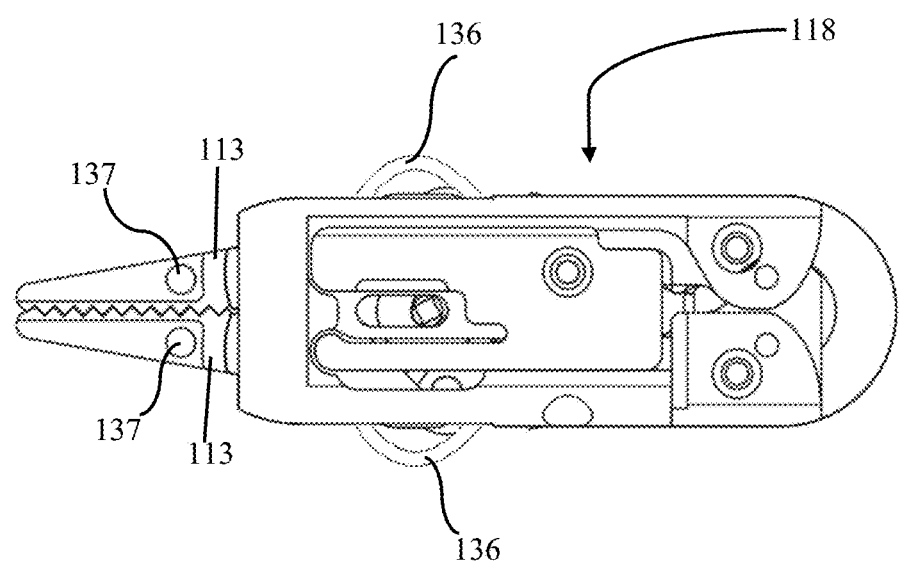
FIG. 39A is a side profile view of a universal grasper with electrical wires and an electrified jaw according to one embodiment.
Figure 39B:
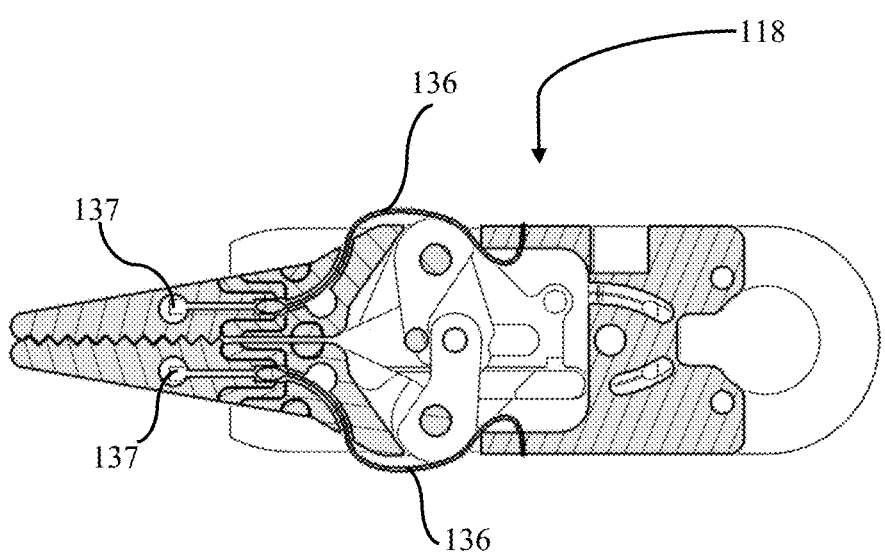
FIG. 39B is a cutaway side profile view of a universal grasper with electrical wires and an electrified jaw according to one embodiment.
Figure 40:
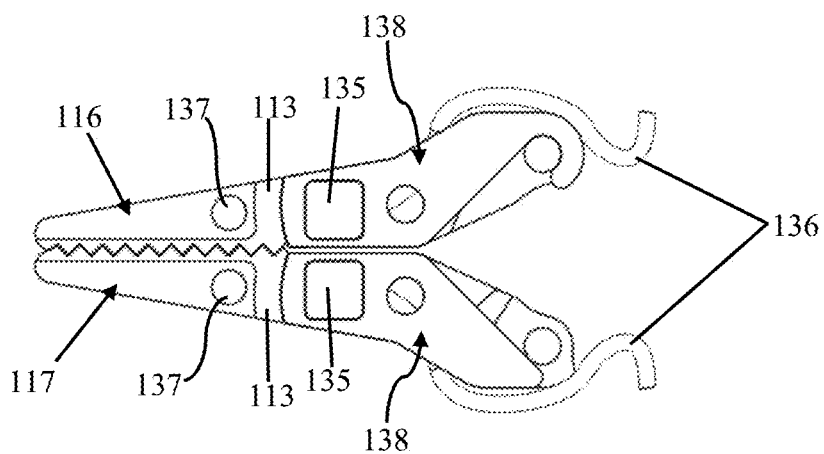
FIG. 40 is an enlarged side profile view of an electrified jaw according to one embodiment.
Figure 41:
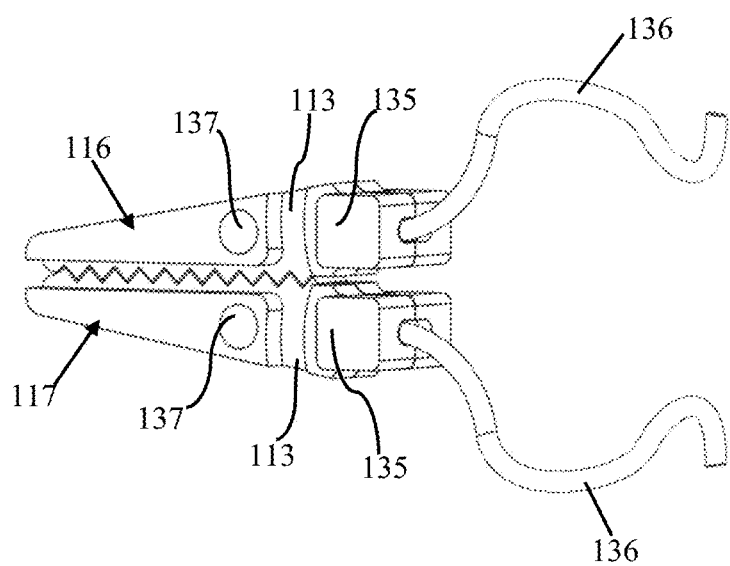
FIG. 41 is an enlarged rear diagonal isometric view of an electrified jaw according to one embodiment.
Figure 42:
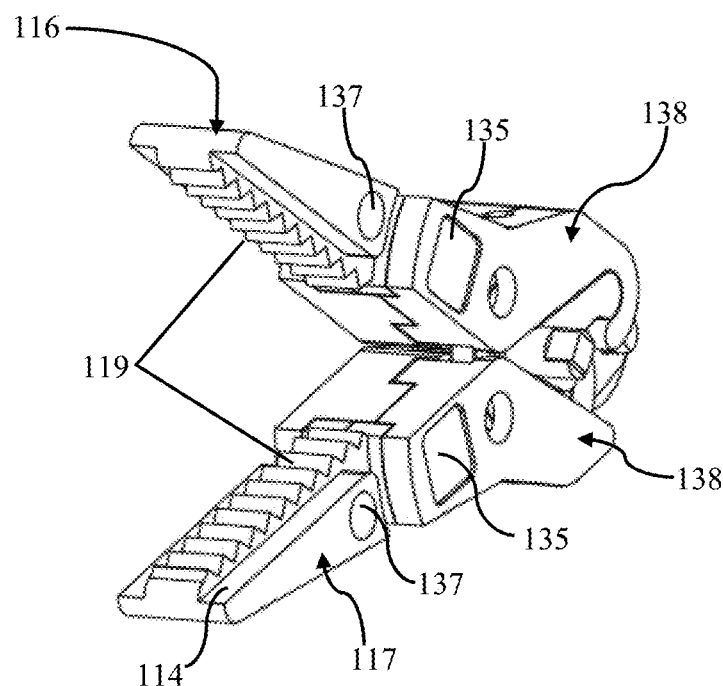
FIG. 42 is an enlarged front diagonal isometric view of an electrified jaw according to one embodiment.
Figure 43:
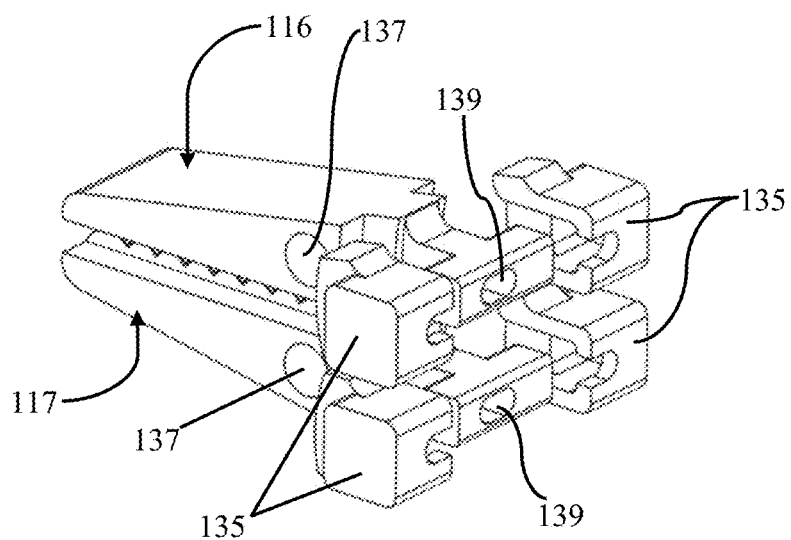
FIG. 43 is an enlarged exploded isometric view of an electrified jaw according to one embodiment.

In some embodiments, the jaw and/or jaw portions of the universal grasper are electrified to allow an electrical current or power to be transferred from the universal grasper to a tool and/or instrument. In some embodiments, the universal grasper 118 is outfitted with electrical wires or conductors that are embedded in the body of the universal grasper 118 as depicted in the illustrative embodiment shown in FIG. 38A and FIG. 38B. In other embodiments, the electrical wires or conductors 136 are routed along the body of the universal grasper 118 as depicted in the illustrative embodiment shown in FIG. 39A and FIG. 39B. The electrical wires 136 are routed from an electrical source, such as a generator and/or a power supply, through the robotic arm to the jaws of the universal grasper 118. In some embodiments two electrical wires or conductors will be found, with one electrical wire 136 going to the first grasper jaw or jaw portion 116 and one electrical wire 136 going to the second grasper jaw or jaw portion 117, as depicted by the illustrative embodiment shown in FIG. 40. In other embodiments one electrical wire 136 is found, with said electrical wire 136 being routed to either the first grasper jaw 116 or the second grasper jaw 117. Alternatively, in other embodiments more than two electrical wires or conductors 136 may be found. As the electrical wires 136 approach the jaws of the universal grasper 118, the wires are routed through wire routing ingresses 139 found on the proximal side of electrical insulators 135. FIG. 41 depicts an illustrative embodiment of the electrified jaws, highlighting the routing path of the electrical wires 136 through the wire routing ingresses 139, into the electrical insulators 135. The wire routing ingresses 139 guide the appropriate electrical wire 136 to either the first grasper jaw 116 or the second grasper jaw 117. FIG. 43 depicts an exploded isometric view of an illustrative embodiment of the electrified jaws, highlighting the location of the wire routing ingresses 139. Once the electrical wires 136 pass through their respective electrical insulator 135, and enter their respective jaw, the electrical wires 136 reach an electrical wire termination site 137 (FIG. 40 and FIG. 41). In some embodiments both the first grasper jaw 116 and the second grasper jaw 117 contain an electrical wire termination site 137, as depicted in the illustrative embodiment shown in FIG. 42. At the electrical wire termination sites 137 the electrical wires 136 terminate and the electrical current or electrical power carried by the electrical wires or conductor 136 is transferred to the electrically conductive contact of the jaws of the universal grasper 118. In these embodiments, the electrical wires or conductors 136 are coupled to the electrically conductive contact on the jaws of the universal grasper 118. In one embodiment, the electrical wire 136 terminates by means of clamping the electrical wire 136 between a rigid surface and a setscrew placed in a tapped hole at the electrical wire termination site 137. Alternatively, in other embodiments, the electrical wires 136 may terminate using any appropriate means known in the field such as a knot tied in the electrical wire 136, or by a crimp connection.

As stated above, the electrical wires 136 pass through electrical insulators 135 prior to reaching their respective termination site 137. The electrical insulators 135 insulate the electrical wires 136 preventing an electrical short from occurring and reaching another part of the universal grasper 118. In some embodiments, the electrical insulators 135 are constructed out of thermoplastic polymers such as ABS, PEEK, polyimide, polyethylene. In other embodiments, the electrical insulators 135 are constructed out of thermoplastic elastomers and/or thermoset plastics, including but not limited to Diallyl-phthalate (DAP), high-density polyethylene (HDPE), and/or an ultra-high-molecular-weight polyethylene (UHMWPE). In other embodiments, the electrical insulators 135 have a composite polymer coating making them biocompatible.

In some embodiments, the electrical insulators 135 are situated on top of one another, with the top insulator insulating the electrical wire 136 that is routed to the first grasper jaw 116 and the bottom insulator insulating the electrical wire 136 that is routed to the second grasper jaw 117 (FIG. 41). In this embodiment, as the first grasper jaw 116 and second grasper jaw 117 are actuated, each of the electrical insulators 135 move with its respective jaw, thus allowing the jaws to maintain their electrified state while staying insulated (FIG. 42).

Figure 44:
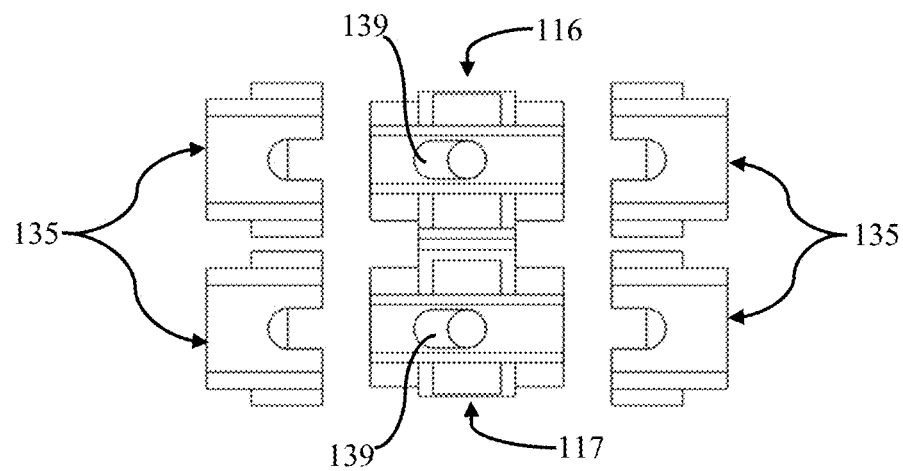
FIG. 44 is an enlarged rear exploded profile view of an electrical insulator of an electrified jaw according to one embodiment.

In some embodiments, each of the electrical insulators 135 are fabricated as two halves, with said halves surrounding the proximal end of the first grasper jaw 116 and the second grasper jaw 117, such that the jaws are insulated and secluded from the other components of the universal grasper, as depicted in the illustrative embodiment shown in FIG. 43. FIG. 44 shows an enlarged exploded view of an illustrative embodiment of the electrical insulators 135, displaying the location of the electrical insulators 135 in relation to the jaws of the universal grasper. In these embodiments, the two halves of the electrical insulators 135 are affixed to each other by a press-fit connection. In other embodiments, the halves are affixed to each other by a thermo-weld connection, adhesive connection and/or any other combination or method known in the field.

Figure 45:
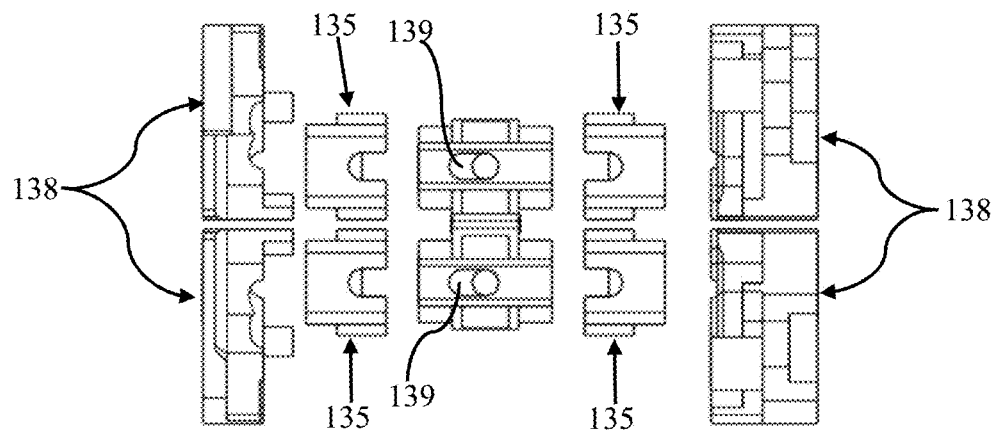
FIG. 45 is an enlarged rear exploded profile view of an electrical sheathing and electrical insulator of an electrified jaw according to one embodiment.

In some embodiments, the electrical insulators 135 are enclosed by an electrical insulator sheathing 138. FIG. 45 shows an enlarged exploded rear view of an illustrative embodiment of electrified jaws of the universal grasper, highlighting the locations of the electrical sheathings 138 in relation to the jaws of the universal grasper and the electrical insulators 135. The electrical insulator sheathing 138 comprises an aperture, with said aperture having a shape compatible to the shape of the electrical insulator 135, such that the sheathing 138 surrounds the insulator 135, as depicted by the illustrative embodiment shown in FIG. 46.

Figure 46:
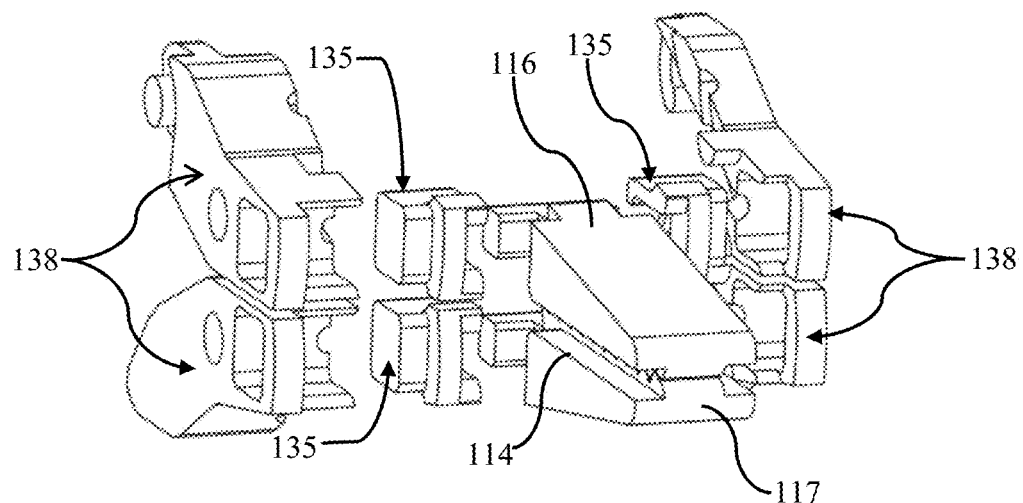
FIG. 46 is an enlarged front diagonal exploded isometric view of an electrified jaw according to one embodiment.

In some embodiments, the universal grasper 118 contains a top electrical insulator sheathing 138 and a bottom electrical sheathing 138 with both the bottom and top sheathing containing two halves, one half for both the left and right side of the universal grasper 118, with the corresponding sheathings 138 coupling to each other by a pin connection, as displayed in the illustrative embodiment shown in FIG. 46. Alternatively, in other embodiments the electrical insulator sheathings 138 are affixed to each other by any means known in the field, such as a welded connection, adhesive connection and/or a snap fit connection. In other embodiments, only one jaw of the universal grasper 118 is electrified, thus only one electrical insulator 135 is found and only one electrical insulator sheathing 138 is found. In some embodiments, the electrical insulator sheathing 138 is fabricated out of biocompatible electrically insulated material known in the art such as thermoplastic polymers such as ABS, PEEK, polyimide, and/or polyethylene. In other embodiments, the electrical insulator sheathing 138 is constructed out of thermoplastic elastomers and/or thermoset plastics, including but not limited to Diallyl-phthalate (DAP), high-density polyethylene (HDPE), and/or a ultra-high-molecular-weight polyethylene (UHMWPE). In other embodiments, the electrical insulator sheathing 138 is constructed out of non-insulated biocompatible materials known in the field, including but not limited to biocompatible metals such as surgical stainless steel, biocompatible ceramics such as aluminum oxide, and/or any other existing biocompatible materials.

In further embodiments, the body of the universal grasper is configured to act as an electrical insulator. In some of these embodiments the body of the universal grasper is constructed out of biocompatible electrically insulated materials known in the art such as thermoplastic polymers including but not limited to ABS, PEEK, polyimide, and/or polyethylene. In other embodiments, the body of the universal grasper is fabricated out of thermoplastic elastomers and/or thermoset plastics, including but not limited to Diallyl-phthalate (DAP), high-density polyethylene (HDPE), and/or an ultra-high-molecular-weight polyethylene (UHMWPE).

Figure 47A:
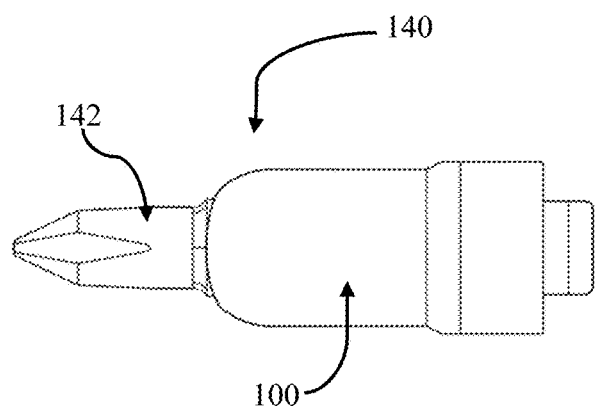
FIG. 47A is a profile view of an electrically actuated tool according to one embodiment.
Figure 47B:
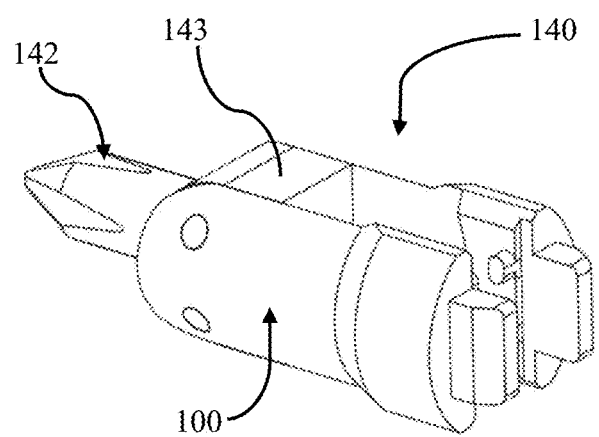
FIG. 47B is a diagonal isometric view of an electrically actuated tool according to one embodiment.
Figure 47C:
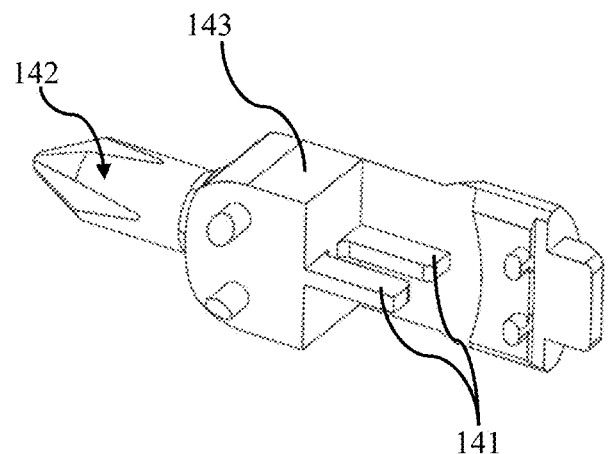
FIG. 47C is a cutaway isometric view of an electrically actuated tool according to one embodiment.
Figure 47D:
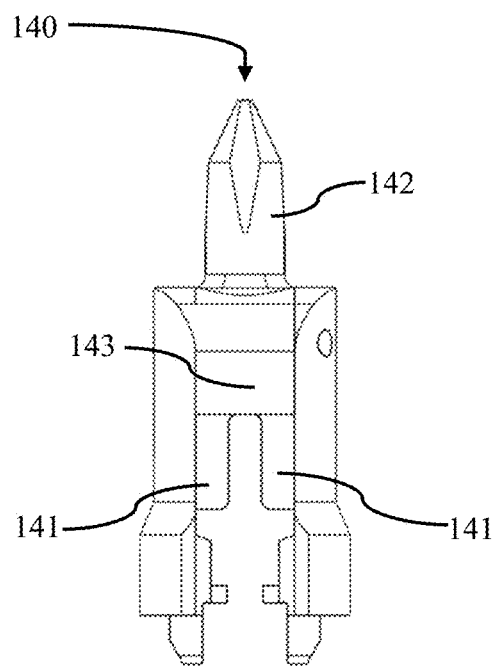
FIG. 47D is a top profile view of an electrically actuated tool according to one embodiment.
Figure 47E:
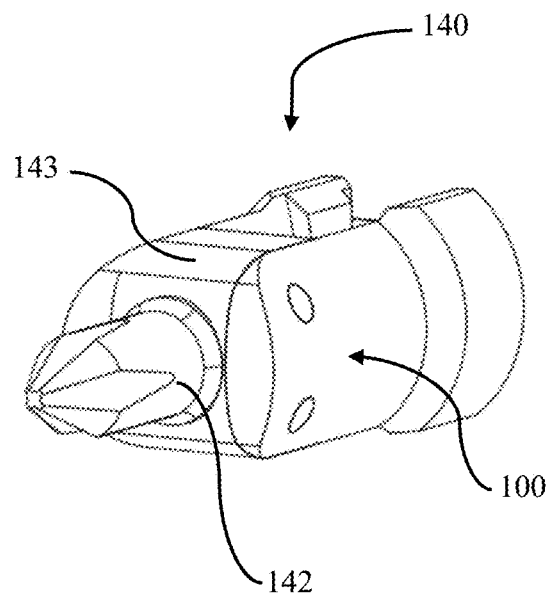
FIG. 47E is a diagonal isometric view of an electrically actuated tool according to one embodiment.
Figure 48A:
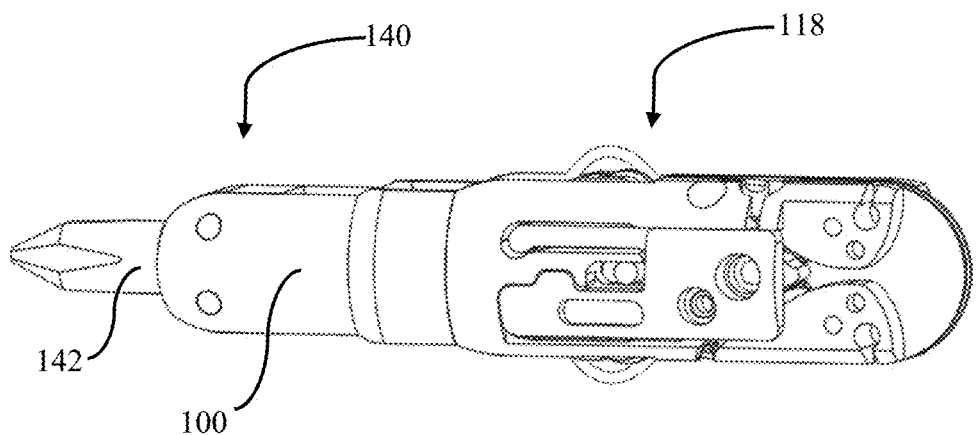
FIG. 48A is an isometric profile view of an illustrative embodiment of an electrically actuated tool when mated to a universal grasper according to one embodiment.
Figure 48B:
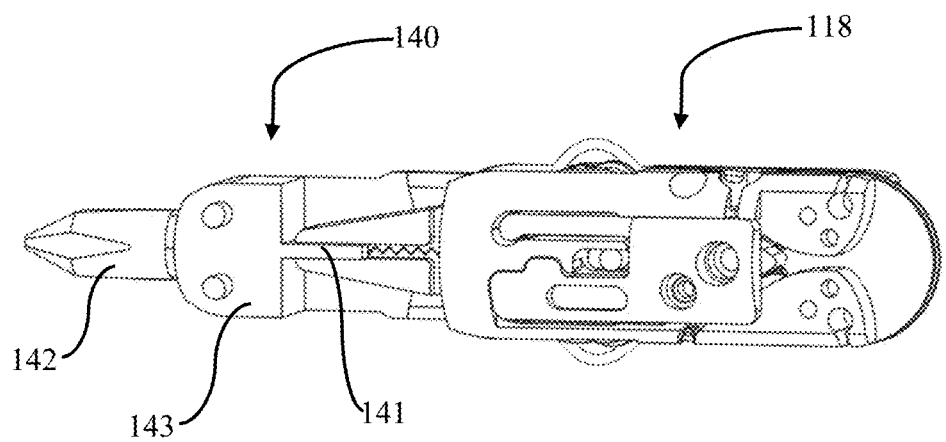
FIG. 48B is a cutaway isometric profile view of an illustrative embodiment of an electrically actuated tool when mated to a universal grasper according to one embodiment.
Figure 49A:
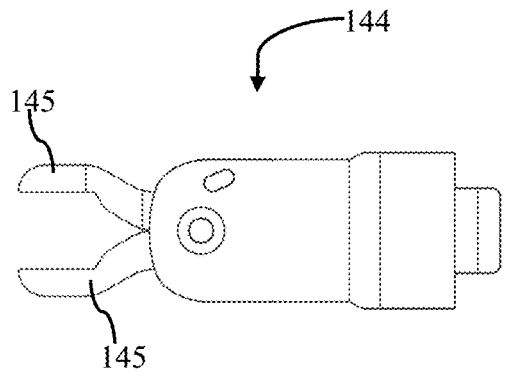
FIG. 49A is a profile view of a disengagement tool according to one embodiment.
Figure 49B:
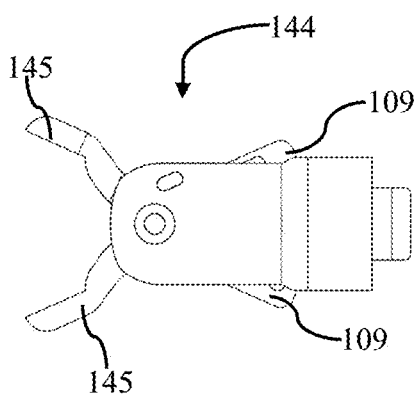
FIG. 49B is a profile view of a disengagement tool, with the clamping members in an open state according to one embodiment.
Figure 49C:
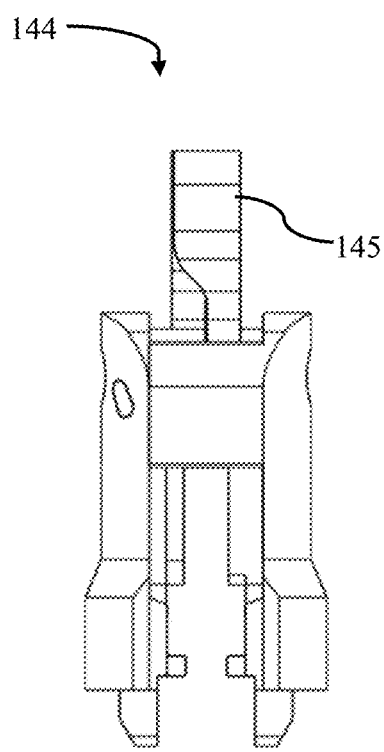
FIG. 49C is a top profile view of a disengagement tool according to one embodiment.
Figure 49D:
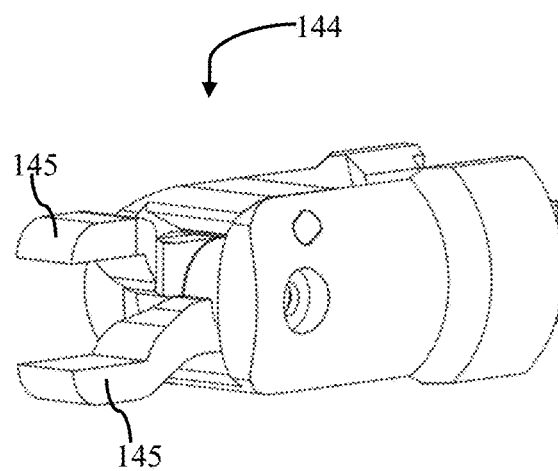
FIG. 49D is an isometric view of a disengagement tool according to one embodiment.

Additionally, in some embodiments where a universal grasper 118 is configured to have electrified jaws, such as where the universal grasper 118 is configured as a bipolar cautery tool, an electrically actuated tool can be coupled to the universal grasper 118. In these embodiments an electrical current or electrical power passes through the grasper jaws to the tool, allowing the tool to be actuated. FIG. 47A and FIG. 47B shows an illustrative embodiment of an electrically actuated drill 140. The electrically actuated tools are insulated from main body of the universal grasper to prevent any other part of a robotic arm from receiving any electrical charge. In some embodiments, the tool hull of the electrically actuated tool has electrical contacts 141, as depicted in the illustrative embodiment shown in FIG. 47C. In these embodiments, the electrical current or electrical power is transferred from the universal grasper jaw to electrical contacts 141 on the tool hull 100. In this embodiment, the jaws of the universal grasper 118 are outfitted with an electrically conductive contact portion at the distal end of the jaw portions, the electrically conductive contacts are coupled to an electrical conductor or electrical wire so that an electrical current is transferred from a power supply to said conductive contacts on the jaw portions. When the universal grasper jaws contacts with the electrical contact on the tool hull 100 the electrical current from the universal grasper jaws is transferred to the electrical contact located on the tool hull 100, as depicted in the illustrative embodiment shown in FIG. 48A and FIG. 48B. In some embodiments, the electrical current is directly routed to the electrically actuated tool via an insulated wire that is imbedded in the tool hull 100. In other embodiments, the imbedded insulated wire (not shown) runs from the electrical contact on the tool hull 100 to an electrical actuator housing 143 which stores the electrical actuator (not shown) of the tool, as depicted in the illustrative embodiment shown in FIG. 47D and FIG. 47E. The electrically actuated tools may contain a variety of electrical actuators, including but not limited to servomotors, linear motors, motors and gear trains and/or any other method or combination of methods known in the field. In other embodiments, the insulated wire is not imbedded in the tool hull 100 but instead routed along the body of the tool hull 100. The electrical current transferred from the jaw of the universal grasper provides power to actuate the instrument of the tool such as drill bit 142, as shown in the illustrative embodiment depicted in FIG. 47A-47E. The instrument of the electrically actuated tools can take on a variety of configurations, including but not limited to micro-saws, bone mills, reaming instruments, and/or other surgical power tools and/or instruments known in the field. In other embodiments, the tool actuation levers 109 of the tool contain electrical contacts that interface with the universal grasper to electrify the instrument of the tool, while allowing the jaw of the universal grasper to actuate the tool.

In further embodiments, where the tool is a static tool, and does not contain an electrical actuator, such as a cautery hook, an electrical wire is routed from the electrical contact directly to instrument of the tool itself, thereby allowing the instrument of the tool to be electrified. In these embodiments, the electrical wire is insulated to prevent an electrical short from occurring. In other embodiments, the electrical wire is removed, as the housing of the tool is constructed of electrical insulation materials having a high surface resistivity, such as polyimide, PEEK, ABS, rubber or any other materials having a high surface resistivity that are known in the art, thus preventing an electrical short from occurring. In these embodiments, the electrified jaws of the universal grasper contact the electrical contact of the tool directly, thereby allowing an electrical current to be transferred to the instrument of the tool directly, without the need for the electrical wire to transfer the electrical current to the instrument. In these embodiments, the instruments are constructed out of electrically conductive materials that are biocompatible, such as surgical steel, aluminum and/or any other biocompatible electrically conductive materials known in the art.

In some embodiments, the universal grasper 118 consists of a first grasper jaw or jaw portion 116 and a second grasper jaw or jaw portion 117. In one embodiment the first grasper jaw 116 and the second grasper jaw 117 move in concert with each other, which in turn causes the tool actuation levers 109 of a tool to move in unison. In an alternative embodiment, the first grasper jaw 116 and the second grasper jaw 117 are capable of moving independently of each other, thus allowing a tool with two tool actuation levers 109 to have independently moving tool actuation levers 109. This embodiment allows a surgeon to more precisely control the actuation of a tool, and provides the surgeon with an added degree of freedom.

In addition, in some embodiments, the jaw of the grasper 118 contains position sensors. In these embodiments, the position sensors are used to accurately measure the position and orientation of the jaws of the grasper. In some embodiments, the first grasper jaw 116 and the second grasper jaw 117 both contain position sensors, which allows the user to know the location of each jaw or jaw portion. In other embodiments, one of either the first grasper jaw 116 and the second grasper jaw 117 contains a position sensor. Additionally, in alternative embodiments, a position sensor is located on the body of the grasper 118. A variety of position sensors may be used in different embodiments, including but not limited to, hall-effect sensors, optical encoders, resistive position sensors, and/or any other standard means of measuring position or combination thereof. In addition, in some embodiments, the jaw or jaw portions of the grasper contain force sensors, as disclosed in International Patent Application No. PCT/US2015/029246. The force sensors detect the force being applied to the levers of a tool by the jaw or jaw portions of the grasper. In some of these embodiments, strain gauges are strategically placed on the grasper housing, while in other embodiments strain gauges are located on the jaw of the grasper. In further embodiments, force sensors may be placed on the lever of a tool. Standard technique may be used to acquire information and calculate the strain and grasper forces.

In some embodiments first grasper jaw or jaw portion 116 and the second grasper jaw or jaw portion 117 each contain engaging surfaces 119, which can take on an abundance of configurations. In one embodiment, the engaging surface 119 is comprised of rigid teeth (FIG. 6) which are located in the center of the engaging surface 119 and transverse from the top to bottom of the jaw. In other embodiments, the engaging surface 119 may be comprised of a textured surface or a smooth surface. In further embodiments, the first grasper jaw 116 and the second grasper jaw contain engaging surfaces 119 that have different configurations. The engaging surfaces 119 located on the universal grasper jaws allow a surgeon to grasp and manipulate tissues during an operation when a tool is not attached.

Figure 12A:
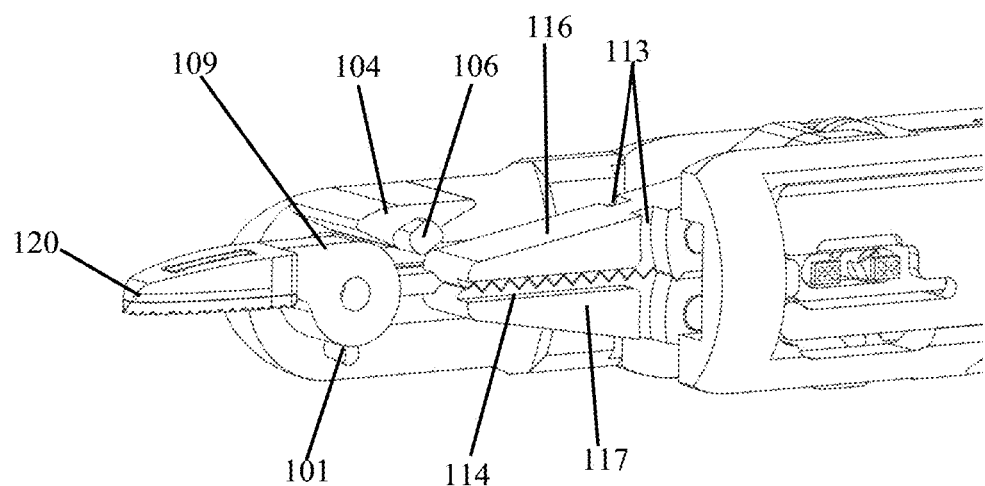
FIG. 12A is a cutaway side isometric view of a tool hull and tool actuation lever when attached to a universal grasper with the grasper jaws in a closed position according to one embodiment.
Figure 12B:
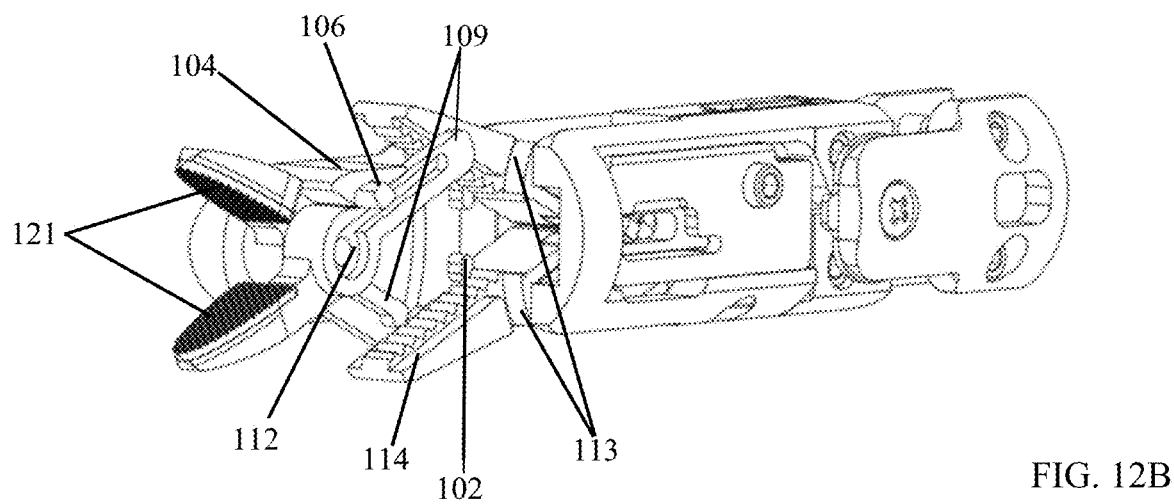
FIG. 12B is a cutaway isometric view of a tool hull and tool actuation levers when attached to a universal grasper with the grasper jaws in an open position according to one embodiment.
Figure 12C:
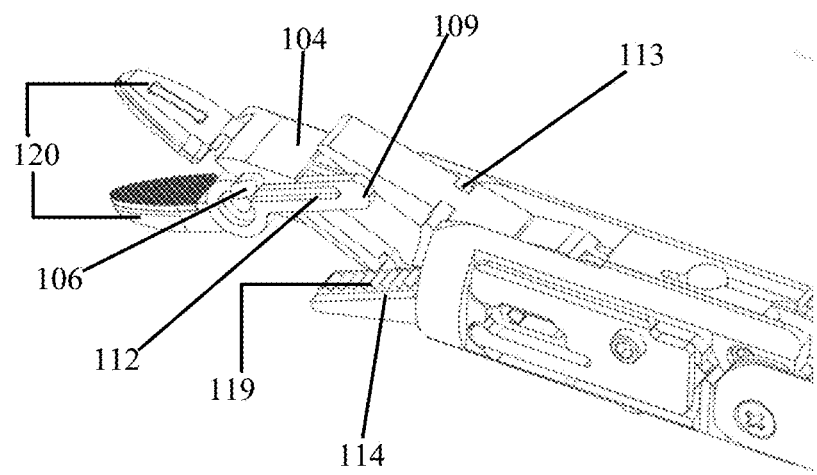
FIG. 12C is a cutaway isometric view of a tool hull and tool actuation levers when attached to a universal grasper with the grasper jaws in an open position according to one embodiment.
Figure 14A:
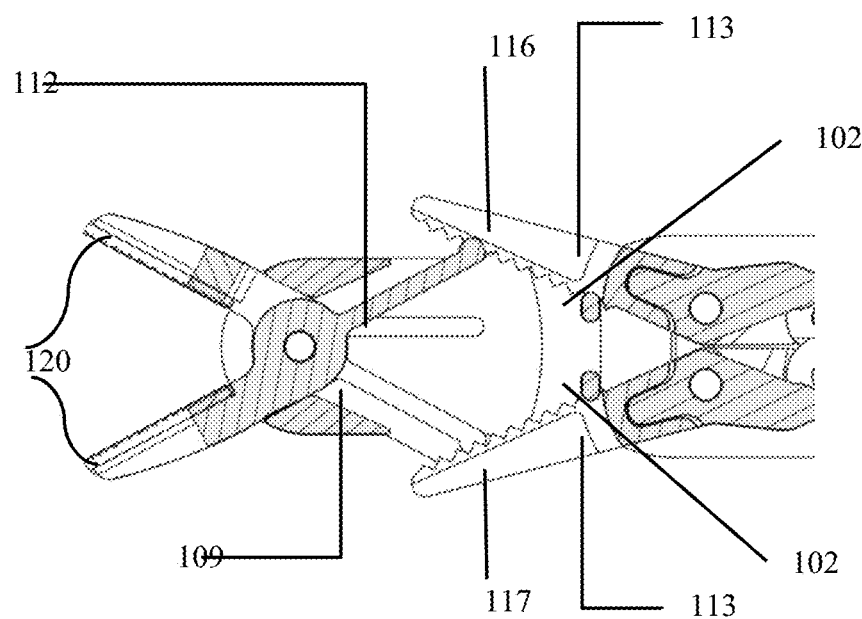
FIG. 14A is a cutaway view of a tool and a universal grasper illustrating the position of tool actuation levers when the universal grasper jaws are in an open position according to one embodiment.
Figure 14B:
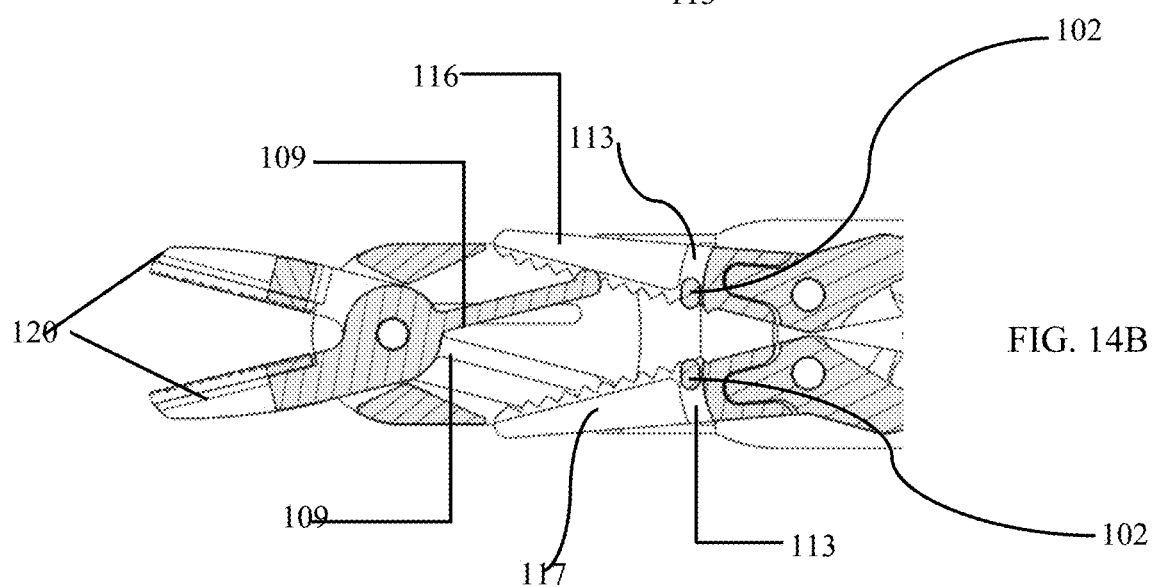
FIG. 14B is a cutaway view of a tool and a universal grasper illustrating the position of tool actuation levers when the universal grasper jaws are in a partial closed position according to one embodiment.
Figure 14C:
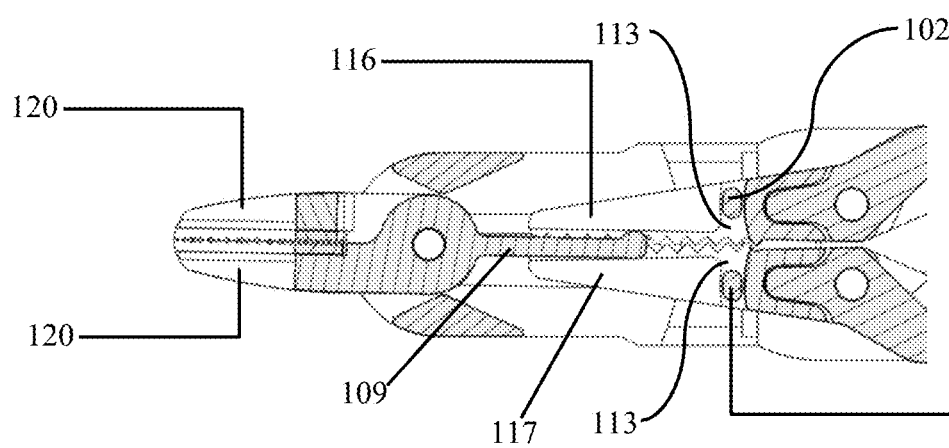
FIG. 14C is a cutaway view of a tool and a universal grasper illustrating the position of tool actuation levers when the universal grasper jaws are in a closed position according to one embodiment.

Notwithstanding the configuration of the engaging surface 119 of the universal grasper 118, in some embodiments located on both sides of engaging surface 119 of the jaws are actuation mating surfaces 114 (FIG. 6) which run from the proximal end of the jaws to the distal end of the jaws. In some embodiments, the actuation mating surfaces 114 are fabricated to be free from perceptible projections, lumps, or indentations, thus allowing the tool actuation levers to move along the surface. The actuation mating surfaces 114 serve a vital function during mating with the tool hull 100 as the tool actuation levers 109 slide along the actuation mating surfaces 114 as illustrated in FIG. 12B and FIG. 12C. In addition, the tool actuation levers 109 sit upon and slide along the actuation mating surfaces 114 when the tool is being actuated as shown in the sequential images of FIG. 14A, FIG. 14B and FIG. 14C.

Figure 11:
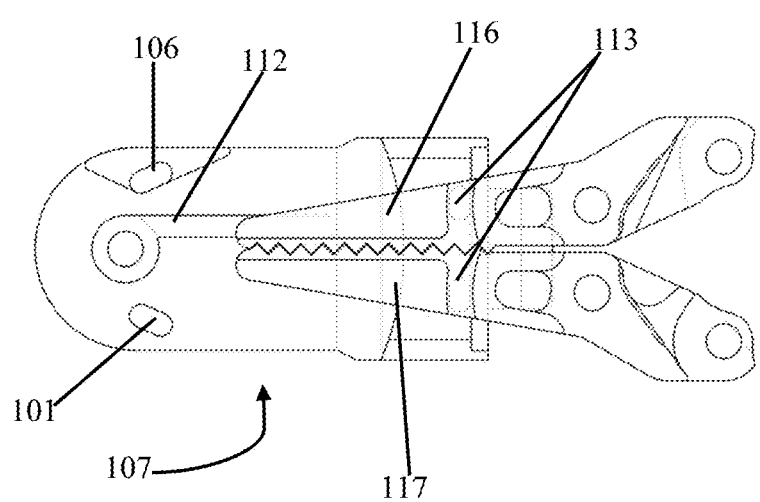
FIG. 11 is an enlarged cutaway view of the right side of a tool hull with a cutaway view of the left side of universal grasper jaws attached to the right side of the tool hull according to one embodiment.

In some embodiments located at the proximal end of the first grasper jaw 116 and the second grasper jaw 117 directly behind the actuation mating surfaces 114 on both the right and left side of the engaging surfaces 119 of the jaws are tool attachment pin channels 113 (FIG. 5 and FIG. 6). During mating between the tool hull 100 and the universal grasper 118, TAP(s) 102 of the tool hull 100 are captured and retained in the tool attachment pin channels 113 (FIG. 11). The tool attachment pin channels 113 are constructed to be wide enough to allow a TAP 102 to move up and down within the channel during the actuation of a tool. The length of the tool attachment pin channels is designed to be proportional to the size of the universal grasper jaws such that the TAPs 102 are located outside of the tool attachment pin channels 113 when the universal grasper jaws are in a fully open position. The vertical distance between the tool attachment pin channels 113 is correlated to the vertical distance between the TAPs 102 with the vertical distance between the tool attachment pin channels 113 being greater than the vertical distance between the TAPs 102 when the universal grasper jaws are in a fully open state, thus allowing the TAPs 102 to enter and mate with the channels.

Figure 13A:
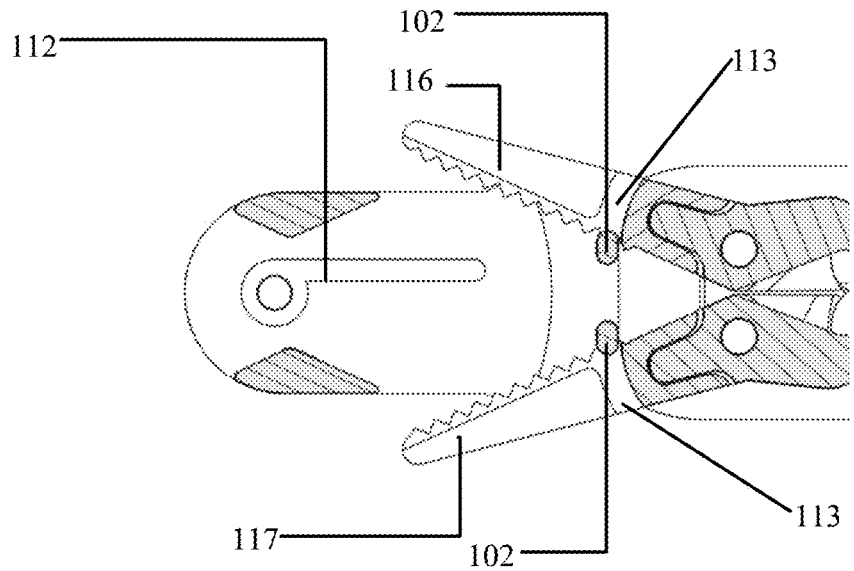
FIG. 13A is a cut away view of the left side of a universal grasper jaws in an open position with a cutaway view of the right side of a tool hull attached to a universal grasper according to one embodiment.
Figure 13B:
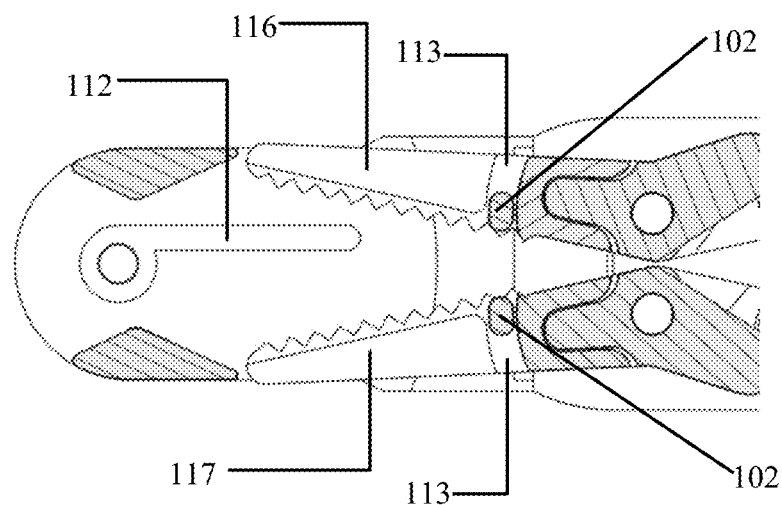
FIG. 13B is a cutaway view of the left side of universal grasper jaws in a partially closed position with a cutaway view of the right side of a tool hull attached to a universal grasper according to one embodiment.
Figure 13C:
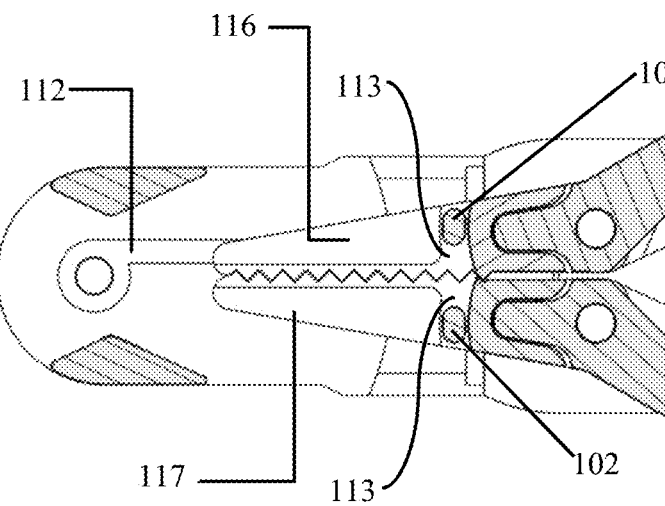
FIG. 13C is a cutaway view of the left side of a universal grasper jaws in a closed position with a cutaway view of the right side of a tool hull attached to a universal grasper according to one embodiment.

As the universal grasper jaws or jaw portions move from an open position to a closed position, the TAPs 102 are forced into the tool attachment pin channel 113 and ride along the distal portion of the channels until the TAPs reach the end of the tool attachment pin channel 113 at which point the universal grasper jaws are in a fully closed position (FIG. 13C). Thus, as the universal grasper jaws move from an open state to a closed state, the universal grasper jaws capture and retain the tool via the TAPs 102 as they are forced further into the tool attachment pin channels 113. This movement sequence is shown in FIG. 13A, FIG. 13B and FIG. 13C. FIG. 13A depicts the location of the TAPs 102 prior to engagement with the tool attachment pin channels 113 according to one embodiment. As illustrated in the embodiment shown in FIG. 13A, the TAPs 102 are situated inside the opening of the universal grasper jaws however are not encompassed in the tool attachment pin channels 113. FIG. 13B depicts the point of engagement where the TAPs 102 enter the tool attachment pin channels 113 according to one embodiment. In addition, FIG. 13B also illustrates the start of the available range of motion the universal grasper jaws are afforded in one embodiment. FIG. 13C depicts the location of the TAPs 102 in the tool attachment pin channels 113 in one embodiment when the universal grasper 118 is in a closed state, which is the extent of its range of motion.

As the grasper jaws move from a fully closed position to a fully open position, the TAPs 102 move from the end of the tool attachment pin channel 113 riding along the distal portion of the channel until the TAPs 102 are disengaged from the tool attachment pin channels 113 at which point the universal grasper jaws have reached a fully open position (FIG. 13A).

The TAP connection prevents separation between the tool hull 100 and the universal grasper 118, as well as provides a retaining force to the docking tabs 103, which constrains the docking tabs 103 in docking station 115. Additionally, this connection provides a surface for the grasper jaws to ride on during actuation, helping to prevent any torsion, or deflection to occur during use.

As mentioned above, in some embodiments located at the distal end of the main body of the universal grasper 118 on both the left and right side of the universal grasper jaws are docking stations 115 (FIG. 6). The docking stations 115 are pockets, which in one embodiment are located on the inside of the main grasper body of the universal grasper 118. In other embodiments, the docking stations 115 may be located on the outside of the main grasper body of the universal grasper 118.

During mating between the tool hull 100 and the universal grasper 118, the docking tabs 103 of the tool hull 100 are inserted into their respective docking stations 115. This connection prevents any separation between the tool hull 100 and the universal grasper 118. In addition, this connection helps to prevent the tool hull 100 and tool from experiencing tilting, torsion or deflection as well as adds stability to the overall device and system. Moreover, this attachment constrains the tool hull 100 in five degrees of freedom, two translation axes-heave (up/down) and sway (left/right)—and three orientation axes, pitch, roll and yaw. The last and sixth degree of freedom, surge (forward/backward), is constrained by the TAPs. FIG. 15A, FIG. 15B, FIG. 16A and FIG. 16B show the coupling sequence of the docking tabs 103 with their respective docking stations 115.

In other embodiments, a magnetic connection is used to retain the docking tabs 102 in their respective docking stations 115. The magnetic connection in these embodiments constrains the tool hull 100 in all six degrees of freedom. As stated above, in these embodiments the docking tabs 102 are constructed with magnetic or electromagnetic material, and the docking stations 115 are constructed of a conductive material with a high permeability. In alternative embodiments, the docking tabs 103 are retained in the docking stations 115 with the connection fashioned via any standard mechanical attachment method known to those in the field such as a spline, press-fit, snap fit and/or any other existing attachment means that allows for attachment and detachment.

Actuation and Attachment

In some embodiments, to attach a tool to the universal grasper 118 a surgeon maneuvers the robotic arm in position behind the proximal end of the tool. The universal grasper 118 must have the same orientation as the tool hull 100 of the tool for which the surgeon is to connect with. The universal grasper 118 must be aligned with the tool hull 100 in such a way to ensure that all mating components of the tool hull 100 are parallel to their respective docking components on the universal grasper 118. Thus, a tool is capable of mating with a universal grasper 118 in any orientation as long as the universal grasper 118 is located behind the proximal end of the tool hull 100 and its mating components are aligned with their respective docking components of the universal grasper 118. The universal grasper 118 on the robotic arm disclosed in International Patent Application No. PCT/US2015/029246, is capable of moving in six degrees of freedom, which allows a surgeon to maneuver a universal grasper 118 into a position and orientation that is harmonious with the position and orientation of the tool hull 100.

Figure 7A:
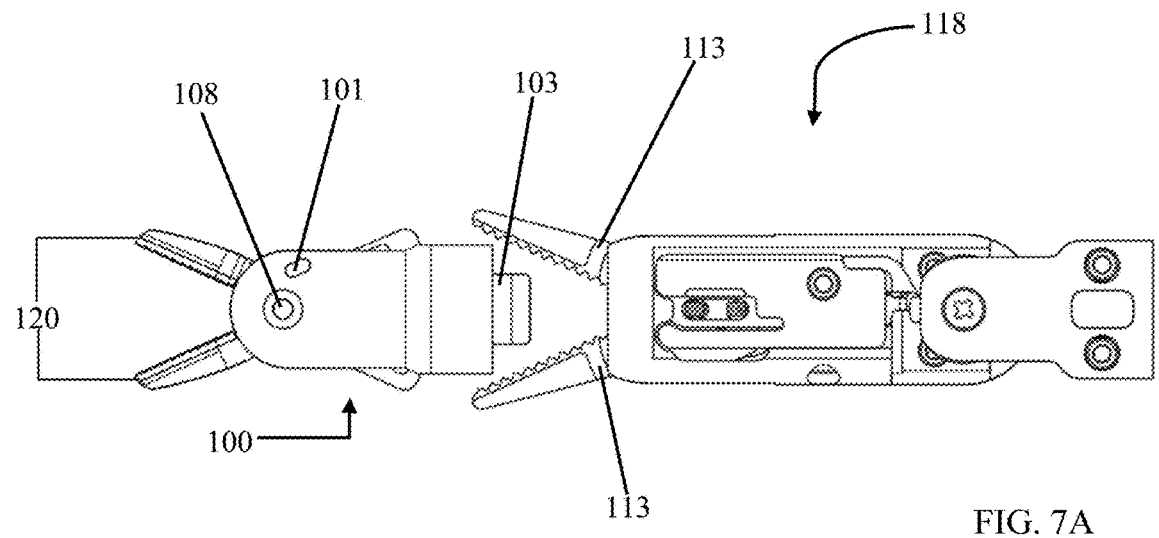
FIG. 7A is a left profile view of the tool hull and universal grasper illustrating their respective states prior to attachment according to one embodiment.
Figure 7B:
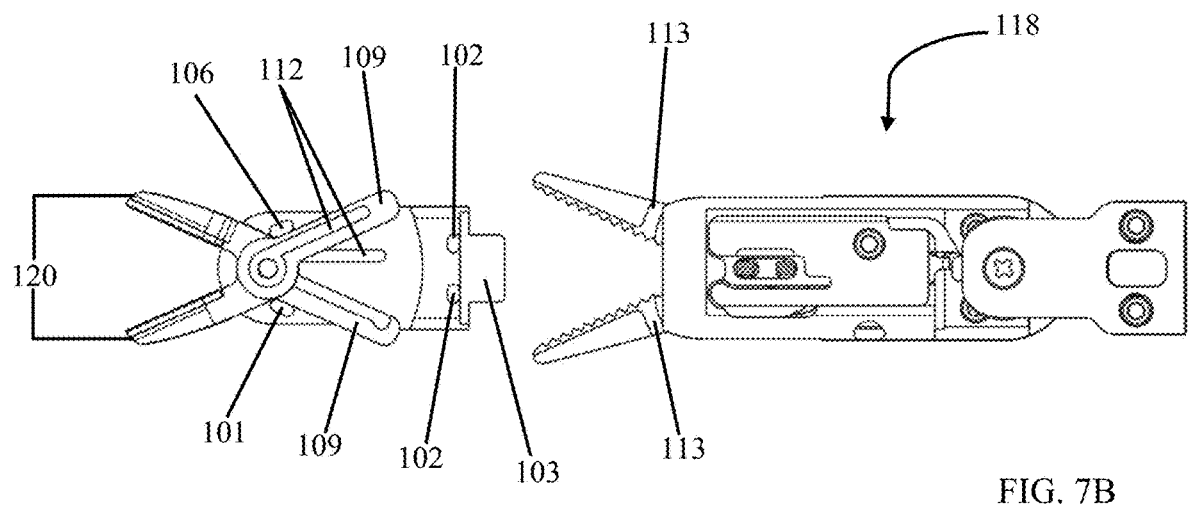
FIG. 7B is a cutaway view of the right side of a tool hull illustrating its state prior to attachment to the universal grasper according to one embodiment.
Figure 8A:
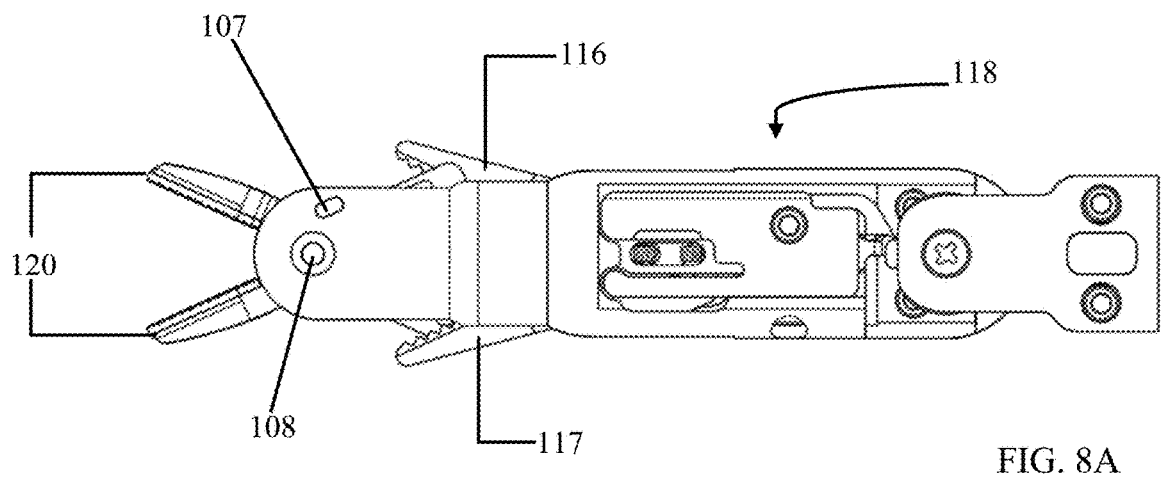
FIG. 8A is a left profile view of a tool hull and a universal grasper illustrating their respective states at the point of initial attachment according to one embodiment.
Figure 8B:
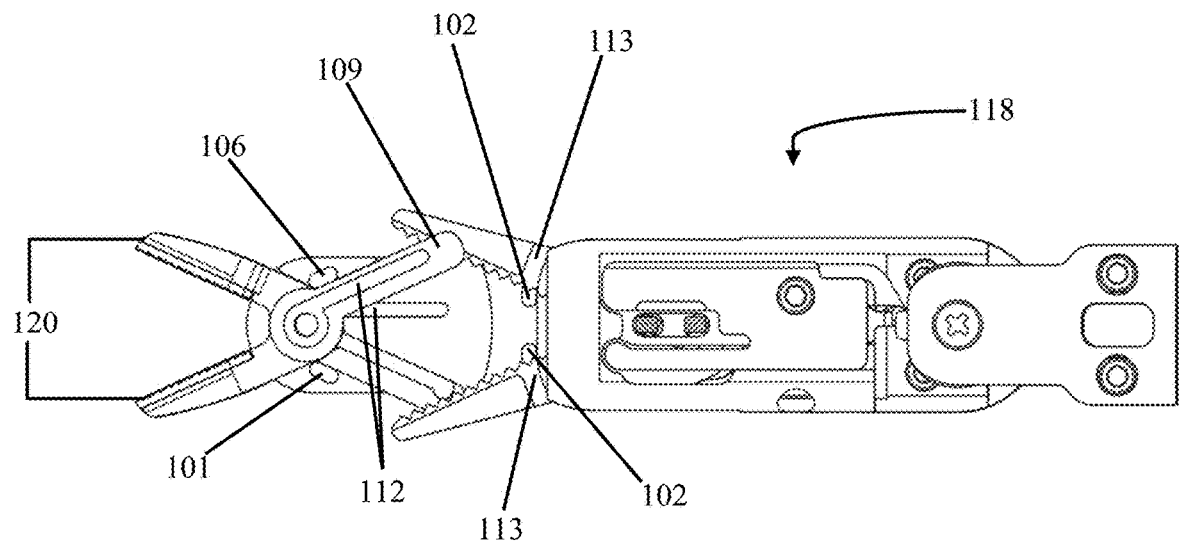
FIG. 8B is a cutaway view of the right side of a tool hull illustrating its state at the point of initial attachment to a universal grasper according to one embodiment.

Prior to attachment the universal grasper jaws are in an open state. The opening of the universal grasper jaws is wide enough to allow the TAPs 102 of a tool hull 100 to move through the opening of the universal grasper jaws and mate with the tool attachment pin channels 113. FIG. 7A and FIG. 7B depict the position of the jaws of a universal grasper 118 prior to mating with a tool according to one embodiment. As a surgeon moves the universal grasper 118 towards the tool hull 100 of a tool, the docking tabs 103 begin to enter their corresponding docking stations 115. FIG. 8A and FIG. 8B depict the position of the jaws of a universal grasper 118 once docking tabs 103 have entered their docking stations 115 according to one embodiment. The docking tabs 103 mate such that the tool is constrained to move only in the direction in which they mated with the universal grasper 118. This mating sequence is shown in FIG. 15A, FIG. 15B, FIG. 16A, and FIG. 16B.

Figure 9:
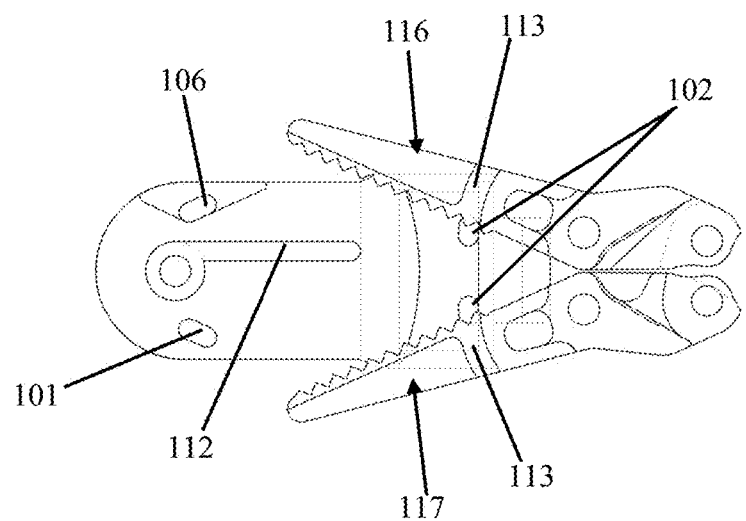
FIG. 9 is an enlarged cutaway view of the left side of universal grasper jaws and a cutaway view of the right side of a tool hull in their respective states at the point of initial attachment according to one embodiment.
Figure 10A:
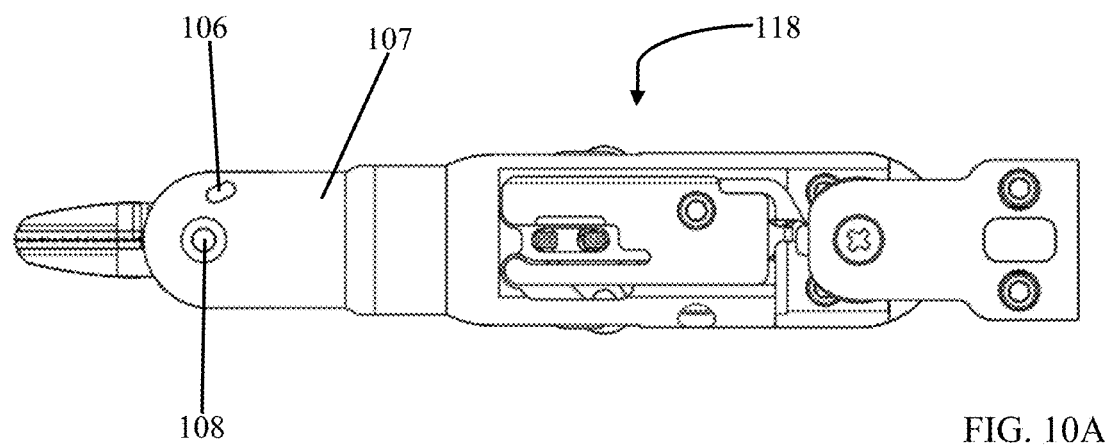
FIG. 10A is a left profile view of a tool hull attached to a universal grasper according to one embodiment.
Figure 10B:
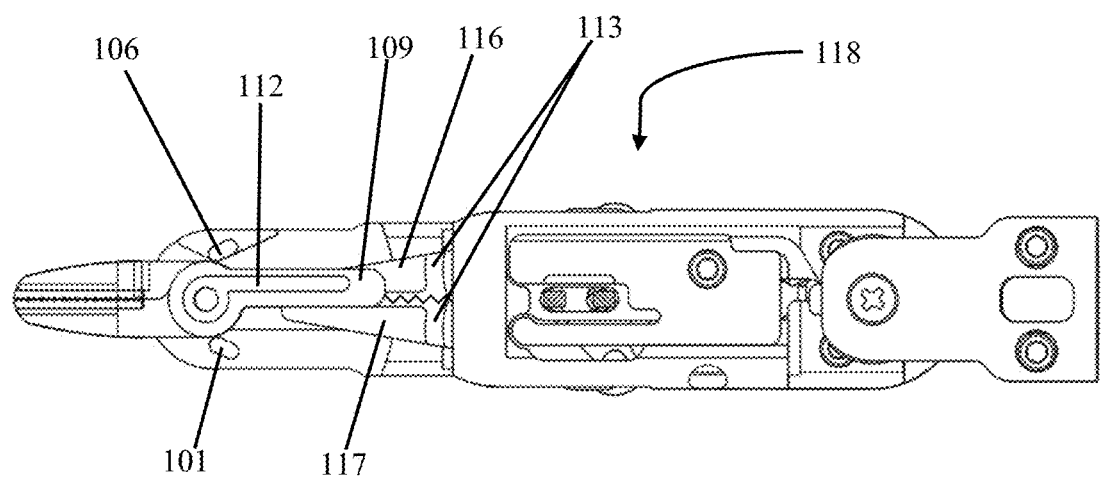
FIG. 10B is a cutaway view of the right side of a tool hull attached to a universal grasper according to one embodiment.

Once the tool hull 100 is seated against the universal grasper 118 with the docking tabs 103 situated in the docking stations 115, the TAPs 102 of the tool hull 100 will be situated within the opening of the grasper jaws outside of the tool attachment pin channels 113 as depicted in the embodiments shown in FIG. 13A and FIG. 9. The surgeon then closes the universal grasper jaws slightly causing the universal grasper jaws to make contact with the TAPs 102. The force from the universal grasper jaws acting on the TAPs 102 causes the TAPs 102 to engage with the tool attachment pin channels 113 as seen in the embodiments illustrated in FIG. 13A and FIG. 13B. Only a small motion is required to engage the TAPs 102, thus allowing the surgeon to retain almost full motion of the universal grasper jaws without disengaging the TAPs 102. With the TAPs 102 engaged, the universal grasper 118 and the tool hull 100 are mated and constrained in all degrees of freedom. FIG. 10A and FIG. 10B show the orientation and position of a tool and a universal grasper 118 once completed mated according to one embodiment.

Once a tool has mated with a universal grasper 118, the surgeon is ready to utilize said tool. In some embodiments, a tool contains two tool actuation levers 109. During actuation, the tool actuation levers 109 slide along actuation mating surfaces 114. In this embodiment, as the universal grasper jaws move towards a closed position, the jaws make contact with the tool actuation levers 109. A force is exerted upon the tool actuation levers 109 when the universal grasper jaws make contact with the levers. The force applied by the universal grasper jaws cause a motion resulting in the tool actuation levers 109 sliding upon the actuation mating surfaces 114. In addition, the force exerted by the universal grasper jaws upon the tool actuation levers 109 causes the levers to pivot about an axis. As the tool actuation levers 109 pivot they slide upon the actuation mating surfaces 114 causing the tool to move between a first and second position, such as an open and closed position. FIG. 12A depicts the position of the tool actuation levers when a tool is attached to a universal grasper 118 and the universal grasper jaws are in a closed stated. The force applied by the universal grasper jaws is captured and retained by the actuator 111 contained in the actuation channels 112. As the surgeon moves the universal grasper jaws from a closed state towards an open state, the force retained by the actuator 111 is transferred back upon the tool actuation levers 109 causing the levers to slide upon the actuation mating surface 114 resulting in the tool returning to its first position. This actuation motion is shown in sequence in FIG. 14A, FIG. 14B and FIG. 14C.

In one embodiment, a tool is actively actuated when the tool is moving towards a first position, such as a closed position, and passively actuated when moving towards a second position via an actuator 111, such as an open position. In alternative embodiments tools are passively actuated towards a first position and actively actuated towards a second position. Furthermore, in some embodiments a tool contains only one tool actuation lever 109. In such embodiments, the tool can be actuated in the same manner as a tool containing two tool actuation levers 109.

Figure 32:
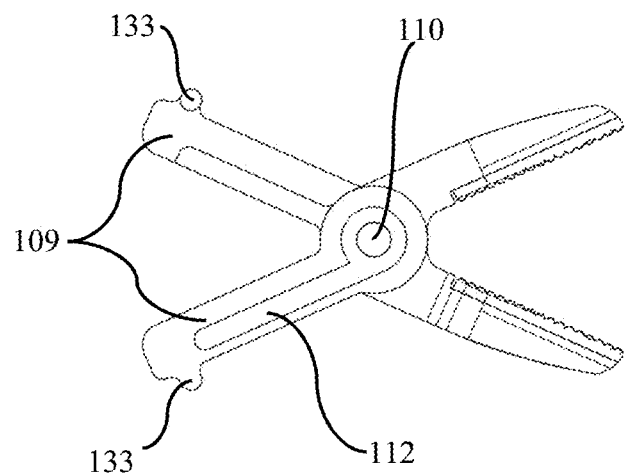
FIG. 32 is a right profile view of exemplary tool actuation levers containing actuation lever nubs according to one embodiment.
Figure 33:
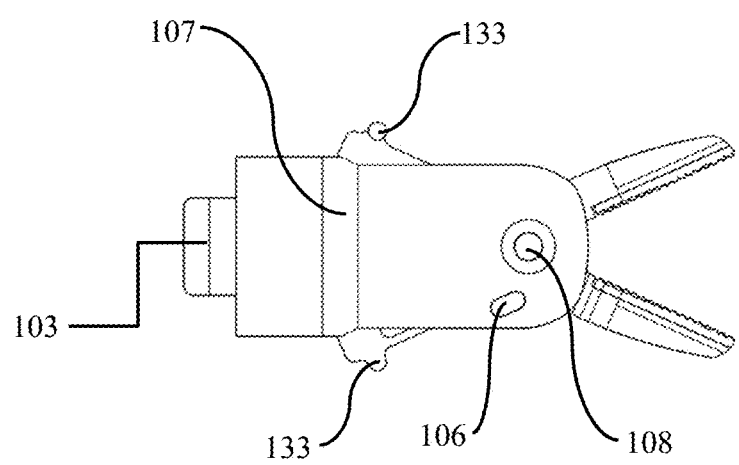
FIG. 33 is a right profile view of an exemplary tool containing actuation lever nubs according to one embodiment.

Additionally, in other embodiments tools can be actively actuated towards a first and second position. In one embodiment, both the left and right tool actuation levers 109 are outfitted with an actuation lever nub or projection 133, which is located on the proximal end of the tool actuation levers 109. FIG. 32 shows an illustrative embodiment of tool actuation levers 109 with actuation lever nubs or projections 133. In one embodiment, the actuation lever nubs 133 are fabricated as part of the tool actuation lever 109 so as to be one solid part. In other embodiments, the actuation lever nubs 133 are affixed to the tool actuation levers 109. This connection is fashioned via any standard attachment means known to those in the field such as a press-fit, glue, weld, and/or any other existing techniques. FIG. 33 illustrates an exemplary embodiment of a tool with actuation lever nubs 133. The actuation lever nubs or projections 133 are constructed out of biocompatible materials known to those in the field, including but not limited to biocompatible metals such as surgical stainless steel, biocompatible plastics such as PEEK, biocompatible ceramics such as aluminum oxide, and/or any other existing biocompatible materials. In addition, in alternative embodiments the actuation lever nubs 133 can take on any configuration and shape capable of handling the force applied to it via the universal grasper jaws, while still allowing the actuation lever nubs 133 to move along the top surface of said universal grasper jaws.

Figure 34A:
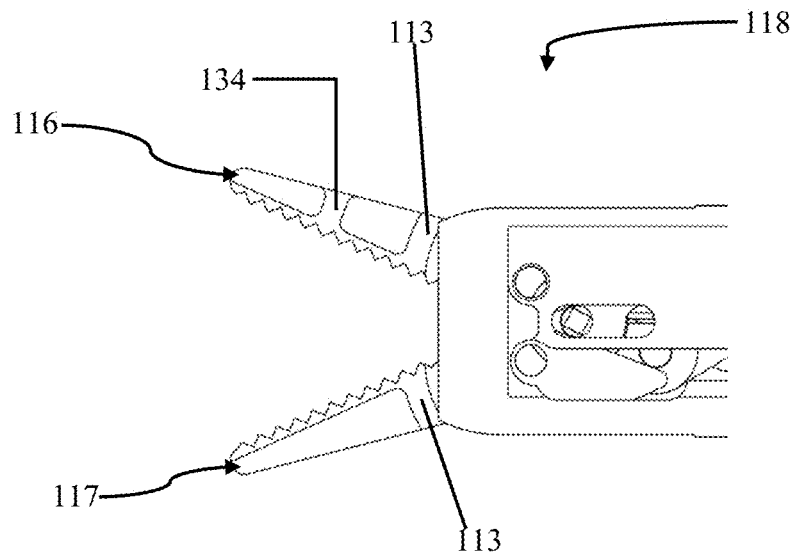
FIG. 34A is a left profile view of a universal grasper containing actuation lever nub channels according to one embodiment.
Figure 34B:
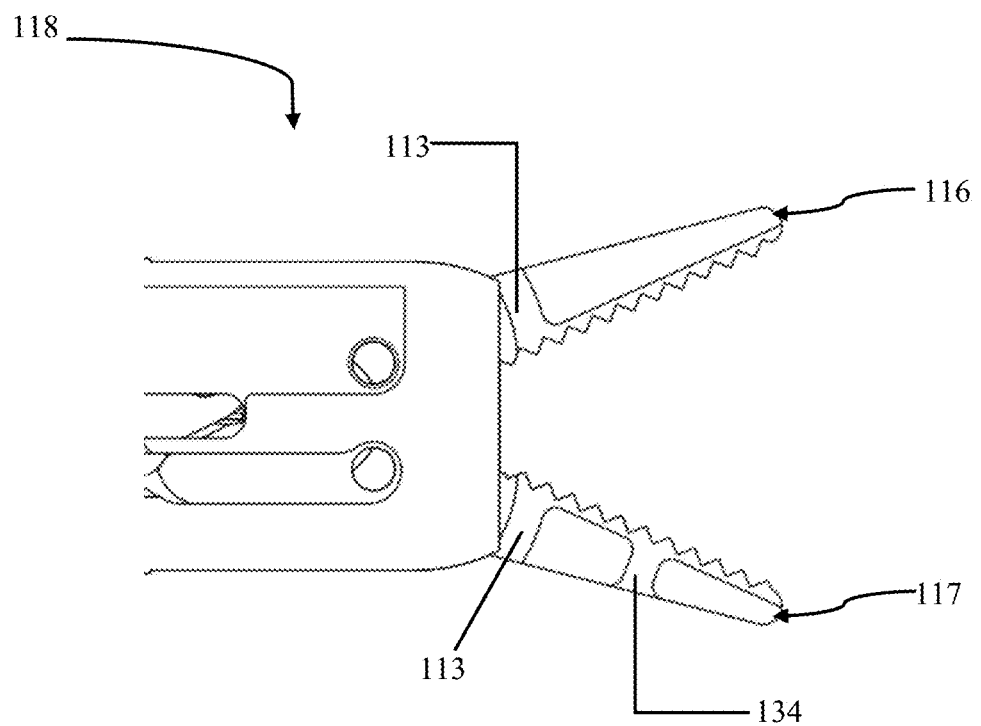
FIG. 34B is a right profile view of a universal grasper containing actuation lever nub channels according to one embodiment.

In one embodiment, the first grasper jaw 116 and the second grasper jaw 117 of the universal grasper 118 contain actuation lever nub channels or force-open channels 134. FIG. 34A shows a left profile view of an illustrative embodiment of the universal grasper 118 depicting the location of the actuation lever nub channel 134 on the first grasper jaw 116 in said embodiment. FIG. 34B shows a right profile view of an illustrative embodiment of the universal grasper 118 depicting the location of the actuation lever nub channel or force-open channel 134 on the second grasper jaw 117 in said embodiment. As depicted in the illustrative embodiment shown in FIG. 34A and FIG. 34B, the actuation lever nub channels 134 are located distal to the tool actuation pin channels 113.

In some embodiments, an actuation lever nub channel 134 is located on the left side of the first grasper jaw 116 and an actuation lever nub channel 134 is located on the right side of the second grasper jaw 117. In this embodiment, an actuation lever nub 133 is located on left tool actuation lever 109 with the actuation lever nub 133 protruding to the right, with a first instrument component affixed to said tool actuation lever 109. In addition, in this embodiment an actuation lever nub 133 is located on the right tool actuation lever 109 with the actuation lever nub 133 protruding to the left, with a second instrument component affixed to said tool actuation lever 109.

In other embodiments, the orientation of the actuation lever nub channels or force-open channels 134 and the orientation of the actuation lever nubs or projections 133 are mirrored. In one embodiment, an actuation lever nub channel 134 is located on the right side of the first grasper jaw 116 and an actuation lever nub channel 134 is located on the left side of the second grasper jaw 117. In this embodiment, an actuation lever nub 133 is located on right tool actuation lever 109 with the actuation lever nub 133 protruding to the left, with a first instrument component affixed to said tool actuation lever 109. Additionally, in this embodiment an actuation lever nub 133 is located on the left tool actuation lever 109 with the actuation lever nub 133 protruding to the right with a second instrument component affixed to said tool actuation lever 109.

In further embodiments only one actuation lever nub channel or force-open channel 134 is found on a universal grasper 118. In one embodiment, an actuation lever nub channel 134 is located on the left side of the first grasper jaw 116 and mates with an actuation lever nub 133 located on the left tool actuation lever 109 of a tool, with a bottom or first instrument component affixed to said lever. In another embodiment, an actuation lever nub channel 134 is located on the left side of the first grasper jaw 116 and mates with an actuation lever nub 133 located on the right tool actuation lever 109 of a tool, with a bottom or first instrument component affixed to said lever. In these embodiments, the top or second instrument component of the tool is static, with the bottom or first instrument component of the tool being affixed to a lever that is actuated.

In additional embodiments only one actuation lever nub channel or force-open channel 134 is found on the second grasper jaw 117 of a universal grasper 118. In one embodiment, an actuation lever nub channel 134 is located on the left side of the second grasper jaw 118 and mates with an actuation lever nub 133 located on the right tool actuation lever 109 of a tool, with a tope or second instrument component affixed to said lever. In another embodiment, an actuation lever nub channel 134 is located on the right side of the second grasper jaw 118 and mates with an actuation lever nub 133 located on the left tool actuation lever 109 of a tool, with a top or second instrument component affixed to said lever. In these embodiments, the bottom or first instrument component of the tool is static, with the top or second instrument component of the tool being affixed to a lever that is actuated.

Figure 35A:
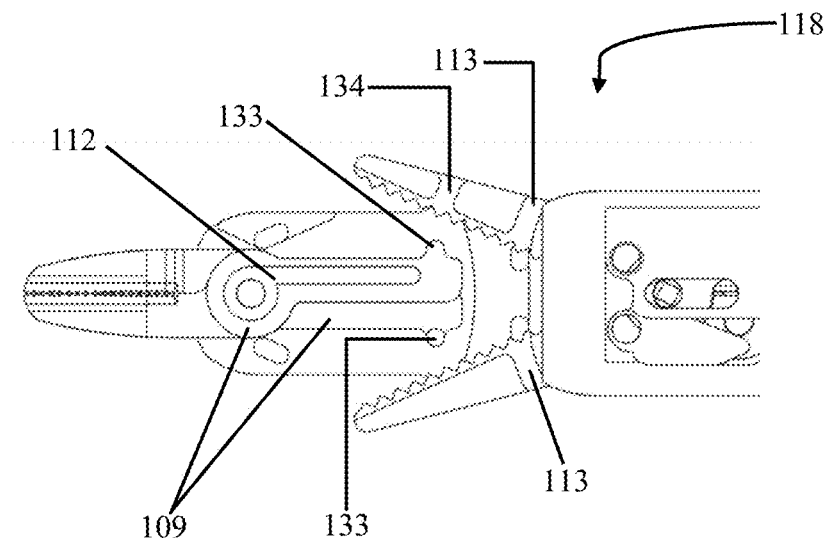
FIG. 35A is a cut away view of an exemplary tool with actuation lever nubs orientated in a mating state with a universal grasper according to one embodiment.
Figure 35B:
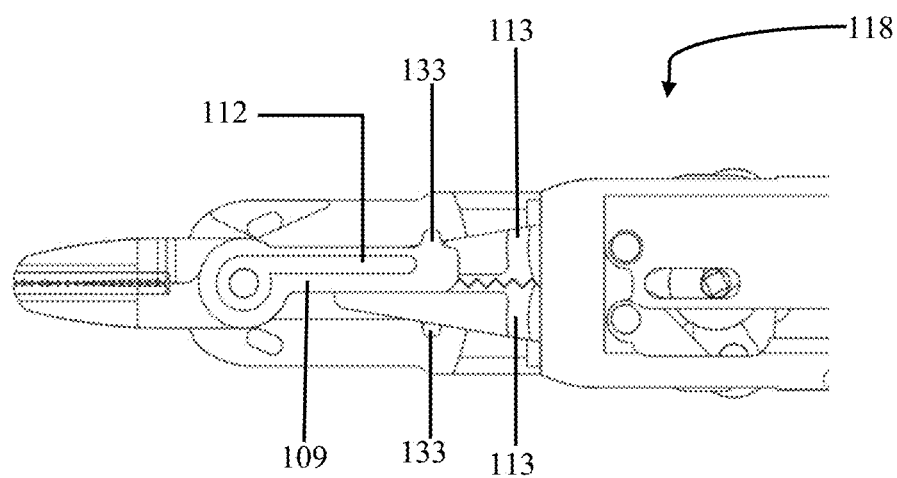
FIG. 35B is a cut away view of an exemplary tool with actuation lever nubs after mating with a universal grasper according to one embodiment.
Figure 36A:
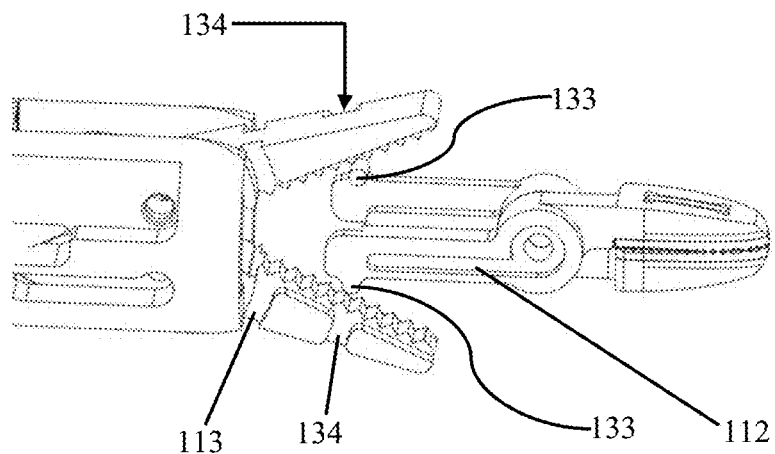
FIG. 36A is an isometric profile view of an embodiment of a universal grasper prior to mating with tool actuation levers containing actuation lever nubs according to one embodiment.
Figure 36B:
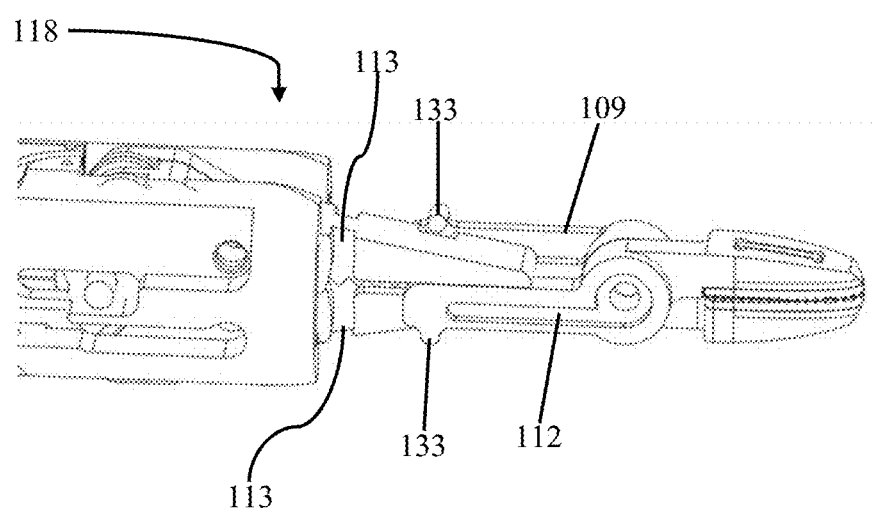
FIG. 36B is an isometric profile view of an embodiment of a universal grasper after mating with tool actuation levers containing actuation lever nubs according to one embodiment.

FIG. 35A shows a cut away view of an illustrative embodiment of a tool orientated in a mating state. As shown in FIG. 35A, the tool is in a closed state, resulting in the left and right tool actuation levers 109 being parallel to one and other. In addition, as illustrated in FIG. 35A, during mating the jaws of the universal grasper 118 are in an open state. With the tool hull mated with the universal grasper 118 as detailed above, the actuation lever nubs 133 are aligned with their respective actuation lever nub channels 134, as depicted in the exemplary embodiment in FIG. 36A. With the actuation lever nubs or projections 133 aligned with the actuation lever nub channels or force-open channels 134 the jaws of the universal grasper move to a closed state. As the jaws of the universal grasper 118 move towards a closed state, the actuation lever nubs 133 enter their respective actuation lever nub channels 134. The actuation lever nub channels or force-open channels 134 are curved to provide the actuation lever nubs or projections 133 with clearance to pass through the channel during mating. FIG. 35B shows a cut away view of an illustrative tool in one embodiment, once a universal grasper has reached a closed state during mating. As depicted in FIG. 35B when the universal grasper 118 has reached a closed state, the actuation lever nubs 133 have passed through their respective actuation lever nub channels 134 and are situated outside of said channels. This mating sequence is depicted in FIG. 36A and FIG. 36B. In addition, as the universal grasper 118 reaches a closed state, the jaws make contact with the tool actuation levers 109, with said levers resting on the actuation mating surfaces 114 of the universal grasper jaws. When the jaws make contact with the tool actuation levers 109, a force is applied on the tool actuation levers 109 by the jaws. The force applied by the jaws is retained by an actuator 111, as detailed above.

Figure 37A:
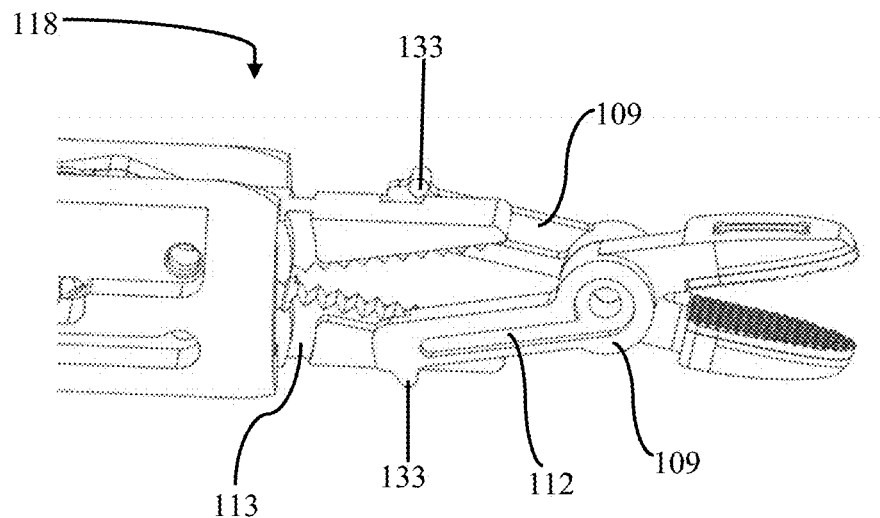
FIG. 37A is an isometric profile view of an embodiment of a universal grasper illustrating initial actuation of an embodiment of tool actuation levers containing actuation lever nubs according to one embodiment.
Figure 37B:
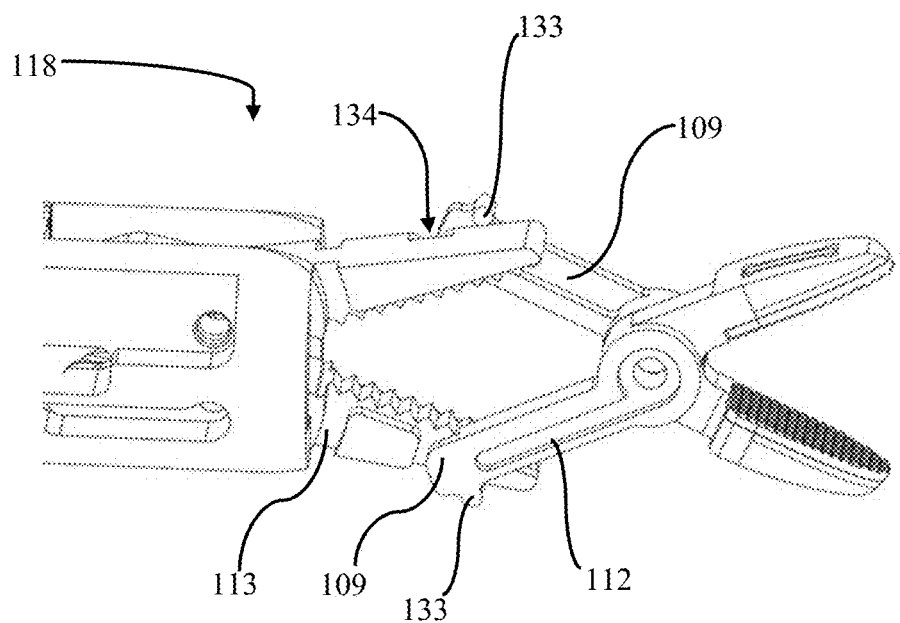
FIG. 37B is an isometric profile view of an embodiment of a universal grasper illustrating actuation of an embodiment of tool actuation levers containing actuation lever nubs according to one embodiment.

With the actuation lever nubs 134 located outside of their respective actuation lever nub channels 134, and the tool actuation levers resting on the actuation mating surfaces 114, the tool has been fully mated with the universal grasper 118 and now is ready to be utilized. As the jaws of the universal grasper 118 move from a closed state to an open state, the force retained by the actuator 111 is transferred back upon the tool actuation levers 109 causing the levers to slide upon the actuation mating surfaces 114. As the tool actuation levers 109 slide upon the actuation mating surfaces 114 the force provided by the actuator 111 causes the tool actuation levers 109 to maintain contact with the actuation mating surfaces 114 of the universal grasper 118. As the tool actuation levers 109 slide upon the actuation mating surfaces 114, the actuation lever nubs 133 pass over the top surface of the jaws of the universal grasper 118. The force transferred back upon the tool actuation levers 109 by the actuator 111 allows the actuation lever nubs 133 to maintain a clearance above the actuation lever nub channels 134 so that as the jaws of the universal grasper 118 move from a closed state to an open state the actuation lever nubs 133 pass over the top surface of the jaws of the universal grasper 118 and do not re-enter the actuation lever nub channels 134 while the tool is being actuated. If a resistance force is exerted upon the tool as it is returning to a first position, the top surface of the jaws of the universal grasper 118 will contact the actuation lever nubs or projections 133, and exert a force upon said nubs, causing the nubs to slide upon the top surface of the jaws of the universal grasper 118. Thus, as the universal grasper 118 move towards an open state the force applied on the actuation lever nubs 133 cause said nubs to stay in contact with the universal grasper 118 resulting in the tool being actively actuated to a first position. This actuation motion is shown in sequence in FIG. 37A and FIG. 37B.

In order to detach a tool containing tool actuation levers 109 with actuation lever nubs 133, the tool must be orientated in a closed state, thus allowing the actuation lever nubs 133 to be located outside of the actuation lever nub channels 134. In one embodiment, this is accomplished by having the tool engagement mechanism 129 of an introducer 126 clamp on the components of the tool, thus constraining the tool from moving. In an alternative embodiment, the tool is inserted into a storage slot of a tool rack, which constrains the tool from moving. With the tool constrained in a closed position, and the actuation lever nubs 133 located outside of the actuation lever nub channels 134, the jaws of the universal grasper 118 are moved to an open position. As the jaws of the universal grasper 118 move towards an open position the actuation lever nubs 133 pass through and exit the actuation lever nub channels 134. With the jaws of the universal grasper 118 in a fully open state the actuation lever nubs or projections 133 have passed through and exited the actuation lever nub channels or force-open channels 134, the surgeon then either pulls the introducer away from the tool hull or tool housing 100, separating the docking tabs or first protrusions 103 from the docking stations or openings 115 of the universal grasper 118, or pulls the universal grasper 118 away from the tool hull 100, releasing the docking tabs 103 from the docking stations 115.

Figure 52A:
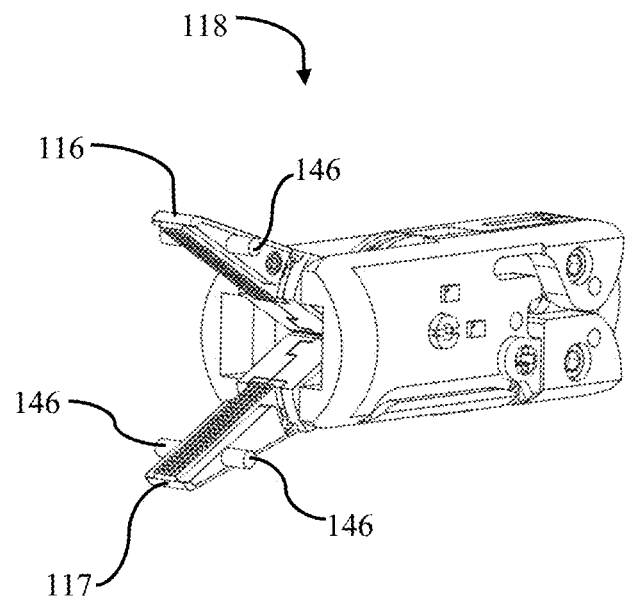
FIG. 52A is an isometric view of a universal grasper with jaws having attachment pins according to one embodiment.
Figure 52B:
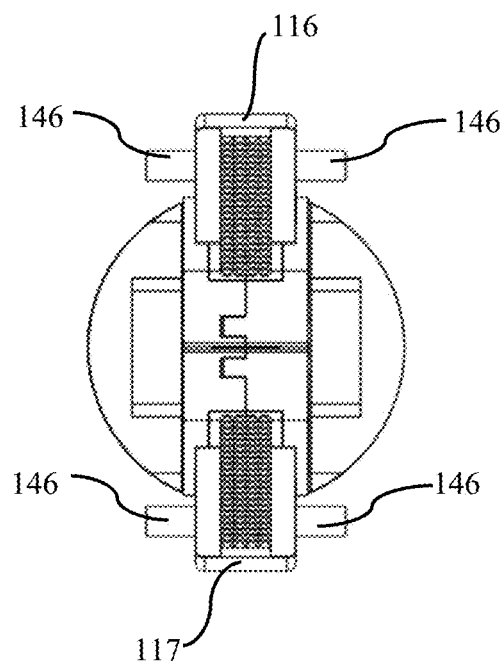
FIG. 52B is an enlarged front profile view of jaws of a universal grasper with attachment pins according to one embodiment.

In alternative embodiments, the coupling between the tool hull 100 and the universal grasper 118 detailed above is inverted. As seen in FIGS. 52A-52B, in some embodiments, the jaws of the universal grasper 118 are fabricated with attachment pins 146 located on the proximal end of the jaws, with said attachment pins 146 protruding from the sides of the first grasper jaw or jaw portion 116 and from the sides of second grasper jaw or jaw portion 117. In other embodiments, the attachment pins 146 are located on the distal end of the jaws of the universal grasper 118. In these embodiments, on the inner surface of the tool hull 100 are channels which are configured to allow the attachment pins 146 from the first grasper jaw 116 and the second grasper jaw 117 to enter and mate with. In addition, in some of these embodiments, the body of the universal grasper 118 is outfitted with docking tabs (not shown) which protrude from both sides of the body of the universal grasper 118. In these embodiments, the tool hull 100 contains ports which are configured to allow the docking tabs of the universal grasper 118 to enter and mate, thus coupling the tool hull 100 and universal grasper 118. The aforementioned docking connection and attachment pin connection work in conjunction, so that the tool hull 100 is constrained in all axes relative to the universal grasper 118.

In further embodiments, only the docking connection is inverted. In these embodiments, the body of the universal grasper 118 is fabricated to contain docking tabs (not shown) which protrude from both sides of said body, and the tool hull 100 is fabricated to contain ports which are configured to allow the docking tabs from the universal grasper 118 to enter and mate with. In these embodiments, the jaws of the universal grasper 118 contain tool attachment pin channels 113 which are configured to mate with TAPs or second protrusions 102 located on the inner surface of the tool hull 100 as detailed above. In other embodiments, only the pin connection is inverted. In these embodiments, the jaws of the universal grasper 118 are fabricated to contain attachment pins 146 (FIG. 52A) that protrude from the sides of the first grasper jaw 116 and the second grasper jaw 117. In these embodiments, the tool hull 100 is fabricated to contain channels on the inner surface of said hull, with said channels configured to allow the attachment pins 146 of the jaws of the universal grasper 118 to enter and mate with.

Figure 53A:
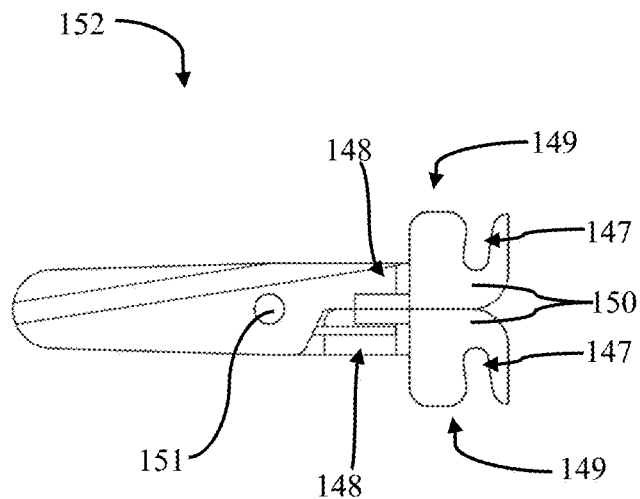
FIG. 53A is a side profile of a tool with attachment appendages containing attachment channels in a closed position according to one embodiment.

In alternative embodiments, the attachment pins 146 of the jaws of the universal grasper 118 are configured to mate with attachment pin channels 147 located on the levers 148 of a tool 152. FIG. 53A, shows an exemplary embodiment of a tool 152 containing attachment pin channels 147. In some embodiments, tool 152 is configured as scissors, while in other embodiments the tool 152 can take on a variety of configurations, including but not limited to needle drivers, forceps, grasper, retractor, surgical stapler, vessel sealer, cautery pin, or caliper.

In some embodiments, the attachment pins 146 are located on the distal end of the jaws, while in other embodiments the attachment pins 146 are located on the proximal end of the jaws of the universal grasper 118 (FIG. 52A). In these embodiments, the levers 148 of the tool 152 are fabricated to contain attachment appendages 149 (FIGS. 53A-53B), which are utilized to mate and couple the universal grasper 118 and the tool 152. The attachment appendages 149 are configured to contain side walls 150 that define attachment pin channels 147. In these embodiments, the attachment pin channels 147 are configured to allow the attachment pins 146 from the jaws of the universal grasper 118 to enter and mate with. In addition, in these embodiments, the attachment pin channels 147 are configured to have rounded edges and/or chamfered edges at the opening, such that the attachment pins 146 can slide into said channels with ease, as well as allowing said pins to enter said channels when the attachment pins 146 are not completely aligned with the attachment pin channels 147.

Figure 53B:
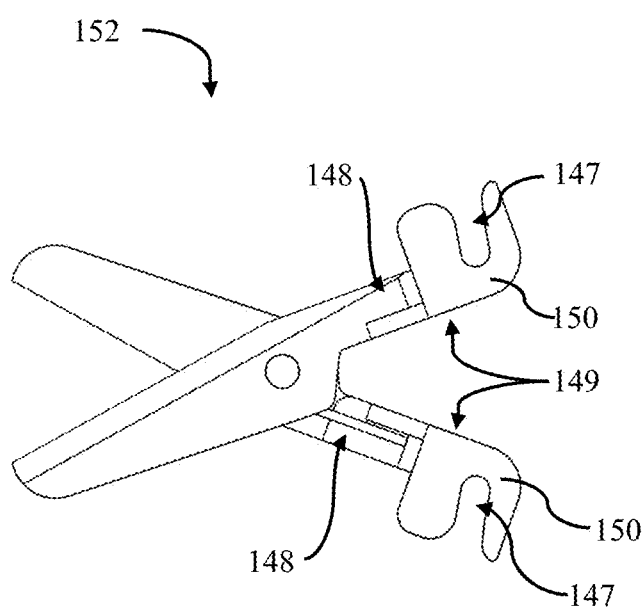
FIG. 53B is a side profile of a tool with attachment appendages containing attachment channels, in an open position according to one embodiment.
Figure 53C:
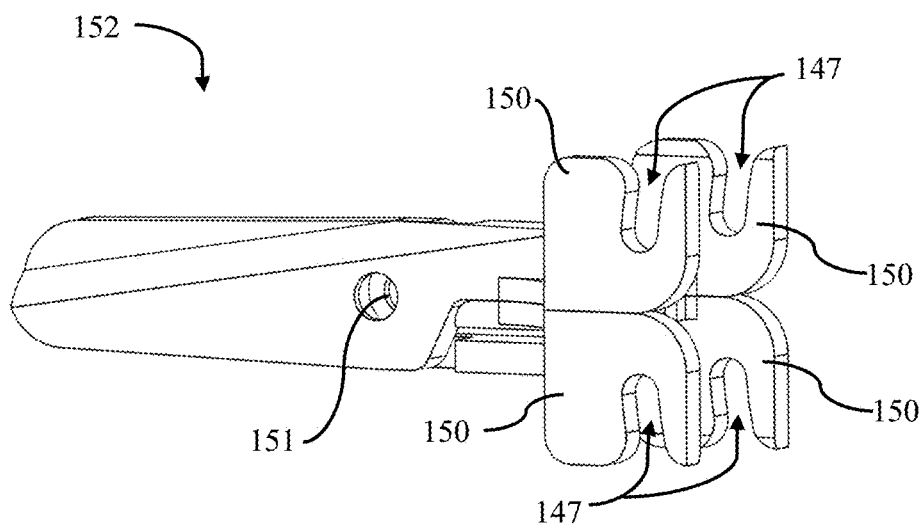
FIG. 53C is an isometric view of a tool, with attachment appendages containing attachment channels, in a closed position according to one embodiment.
Figure 53D:
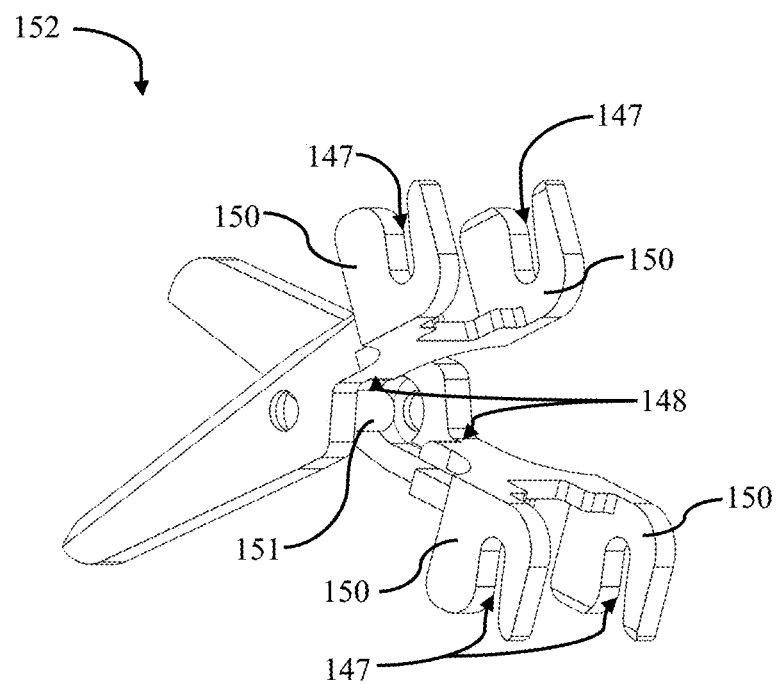
FIG. 53D is an isometric view of a tool with attachment appendages containing attachment channels, in an open position according to one embodiment.
Figure 54A:
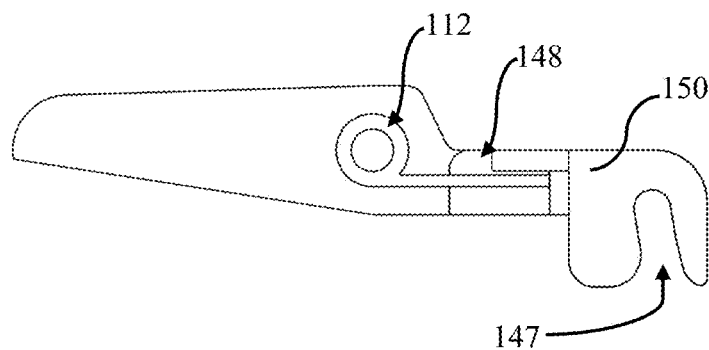
FIG. 54A is a cutaway view of a tool with attachment appendages containing attachment channels, according to one embodiment.
Figure 54B:
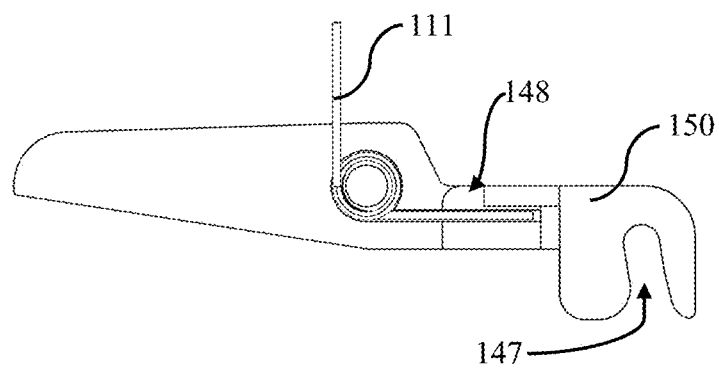
FIG. 54B is a cutaway view of a tool with attachment appendages containing attachment channels, according to one embodiment.
Figure 56A:
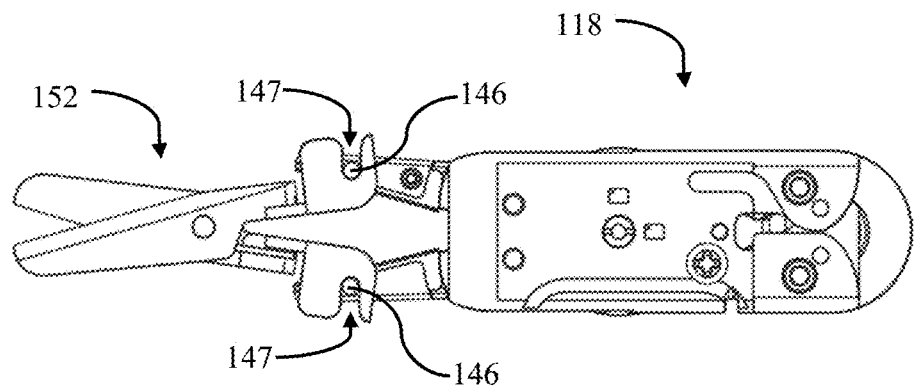
FIG. 56A is a side profile view of an embodiment of a universal grasper with attachment pins illustrating initial actuation of an embodiment of a tool with attachment appendages containing attachment channels, according to one embodiment.
Figure 56B:
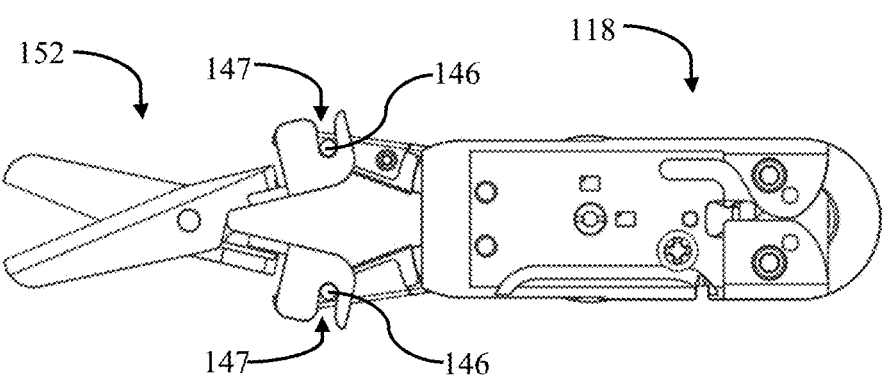
FIG. 56B is a side profile view of an embodiment of a universal grasper with attachment pins illustrating actuation of an embodiment of a tool with attachment appendages containing attachment channels, according to one embodiment.
Figure 56C:
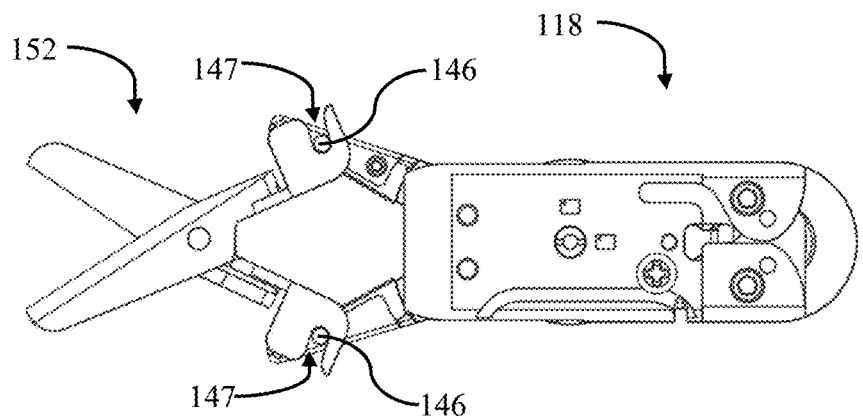
FIG. 56C is a side profile view of an embodiment of a universal grasper with attachment pins illustrating actuation of an embodiment of a tool with attachment appendages containing attachment channels, according to one embodiment.

As shown in FIG. 53B the side walls 150 of the attachment appendages 149 protrude from the proximal end of the levers 148, with each side wall 150 containing an attachment pin channel 147. As shown in FIGS. 53C-53D, the attachment pin channels 147 are configured to be curved in shape, with the curvature of said channels configured to allow the attachment pins 146 of the jaws of the universal grasper 118 to enter when the tool 152 is in a closed state, and retain the attachment pins 146 when the tool 152 is actuated. In these embodiments, located on the inner surface of the levers 148 are actuation channels 112, which are configured to house the actuator 111 of the tool 152 (FIGS. 54A-54B). As detailed above, the actuator 111 can be any mechanical actuation component or combination of components known in the art such as a torsion spring, a leaf spring, a cable or any other mechanical actuation component or combination of components known in the art capable of actuating a tool and/or instrument. The actuator 111 allows the jaws of the universal grasper 118 to interact with the levers 148 of the tool 152, resulting in said tool being capable of being manipulated from a first position and second position, including but not limited to an open and closed position. The actuator 111 is operably connected to both levers 148 of the tool 152, with said actuator 111 siting within the actuation channels 112 of both levers 148. The actuator 111 is configured to apply a force upon the attachment appendages 149 such that the attachment pins 146 of the jaws of the universal grasper 118 are retained in the attachment pin channels 147 as the levers 148 of the tool 152 and the jaws of the universal grasper 118 move towards an open position. In these embodiments, as the jaws of the universal grasper 118 initially move from a partially closed position towards an open position, the actuator 111 applies a force upon the levers 148 causing said levers to maintain contact with the pins on the jaws of the grasper. As the levers 148 move towards an open position, the attachment appendages 149 and the attachment channels 147 rotate with said levers 148, and the jaws of the universal grasper 118 rotate about a separate path. The diversion between the path defined by the channel 147 of the levers 148 and the path of rotation of the jaws of the universal grasper 118, is such that, the attachment pins 146 of the jaws of the universal grasper 118 contact the walls of the attachment pin channels 147 of the levers 148 causing the attachment pins 146 to be retained within said channels. This actuation sequence is shown in FIGS. 56A-56C.

Figure 55A:
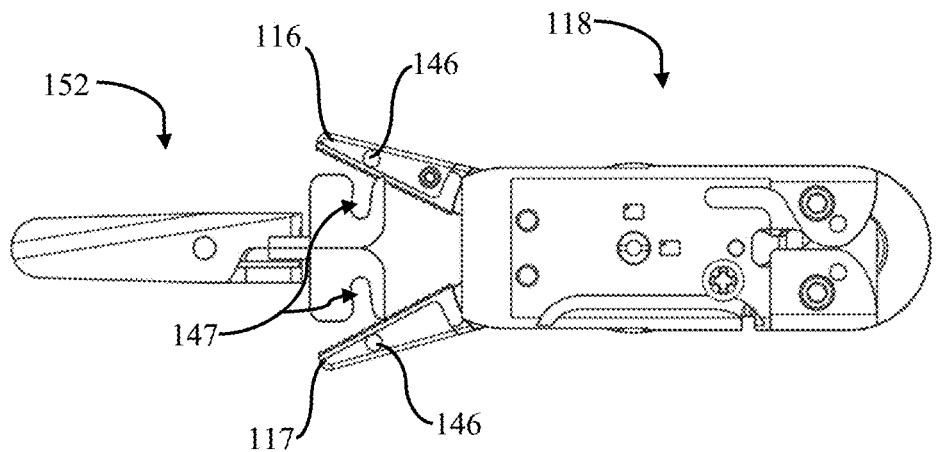
FIG. 55A is a side profile view of an embodiment of a universal grasper with attachment pins prior to mating with a tool with attachment appendages containing attachment channels, according to one embodiment.
Figure 55B:
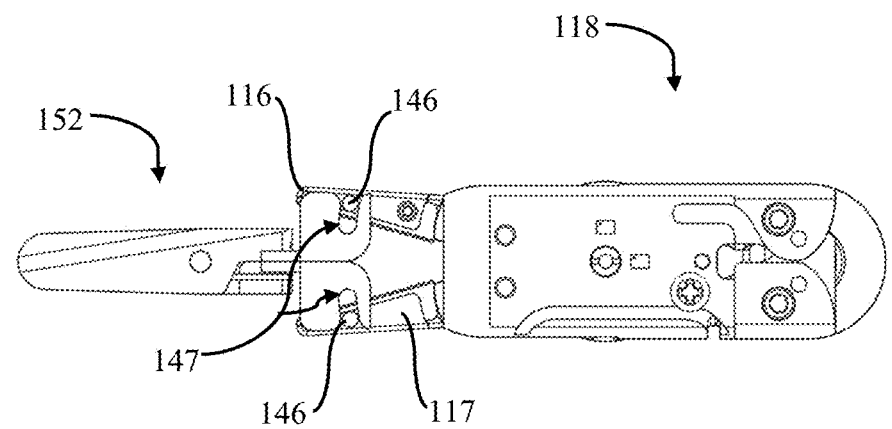
FIG. 55B is a side profile view of an embodiment of a universal grasper with attachment pins illustrating initial mating with a tool with attachment appendages containing attachment channels, according to one embodiment.
Figure 55C:
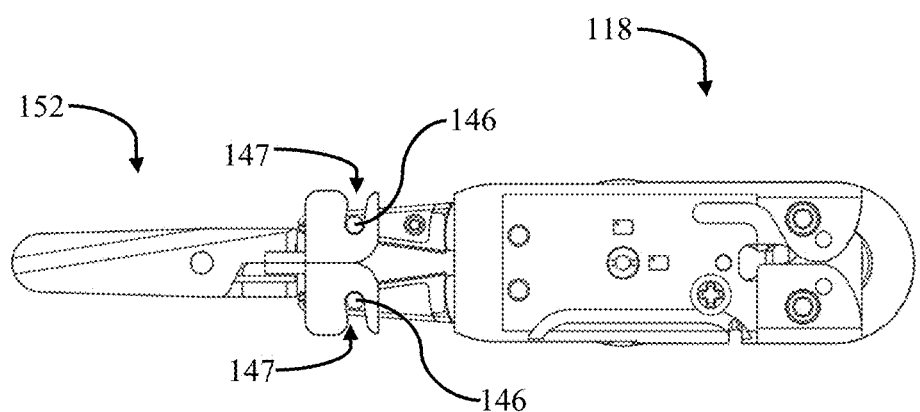
FIG. 55C is a side profile view of an embodiment of a universal grasper with attachment pins after mating with a tool with attachment appendages containing attachment channels, according to one embodiment.

As mentioned above, in order for the attachment pins 146 of the jaws of the universal grasper 118 to engage and enter their respective attachment pin channels 147, the tool 152 and the levers 148 of said tool must be in a closed position, as depicted in FIG. 55A. As depicted by the sequence shown in FIG. 55A-55C, with the levers 148 of the tool 152 in a closed position, as the jaws of the universal grasper 118 move from an open position towards a closed position, the attachment pins 146 of the jaws of the universal grasper 118 are forced into the attachment pin channels 147, with said channels guiding the attachment pins 146 until said pins reach the end of the channels 147, at which point the jaws of the universal grasper 118 and the tool 152 are coupled. As shown in FIG. 55C, when the attachment pins 146 have reached the end of their respective attachment pin channel 147, there is a degree of separation between the first jaw 116 and the second jaw 117, this separation ensures that the pins 146 constantly apply a force upon the channels 147. As the jaws of the universal grasper move towards an open state, the attachment pins 146 are retained in the attachment pin channels 147. During actuation of the tool 152, the attachment pins 146 transmit a force from the jaws of the universal grasper 118 such that the levers 148 of the tool 152 rotate about a fulcrum 151 from a first position to a second position, similar to the actuation of tools detailed above.

During actuation of the tool 152, the actuator 111 of said tool along with the attachment pin channels 147, constrain the attachment pins 146 within said channels. When the universal grasper 118 is coupled to the levers 148 of the tool 152, via the connection detailed above, in order to disengage the attachment pins 146 from the attachment pin channels 147, the tool 152 and the levers 148 of said tool must be in a closed position, which results from the jaws of the universal grasper 118 applying a force upon the levers 148 via the attachment pins 146. With the tool 152 and levers 148 of said tool in a closed position, the tool 152 is constrained in the closed position by clamping down on the distal end of said tool. In some embodiments, the introducer 126 is utilized to clamp the distal end of the tool 152, while in other embodiments the universal grasper 118 of one of the robotic arm 125 is utilized to clamp the tool 152 in a closed position. With the tool 152 clamped in a closed position, the path of the attachment pin channels 147 is aligned with the path of rotation of the jaws of the universal grasper 118 such that as the jaws from the universal grasper 118 move from a closed position towards an open position, the attachment pins 146 of the jaws of the universal grasper 118 traverse through the attachment pin channels 147 and exit said channels, at which point the jaws of the universal grasper 118 are in a fully open state.

In alternative embodiments, the above detailed connection is inverted. As depicted in the illustrative embodiment shown in FIG. 57B and FIG. 57C, in some embodiments, a tool 158 has a lever 153 which is outfitted with attachment pins 154. In one embodiment, tool 158 is configured as scissors, while in other embodiments tool 158 can take on a variety of configurations, including but not limited to needle drivers, forceps, grasper, retractor, surgical stapler, vessel sealer, cautery pin, or caliper.

Figure 59A:
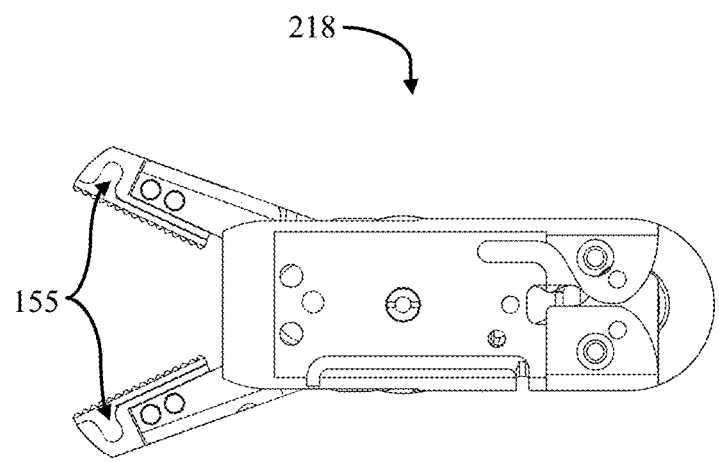
FIG. 59A is a side profile view of a universal grasper with jaws having attachment channels, in an open position according to one embodiment.
Figure 59B:
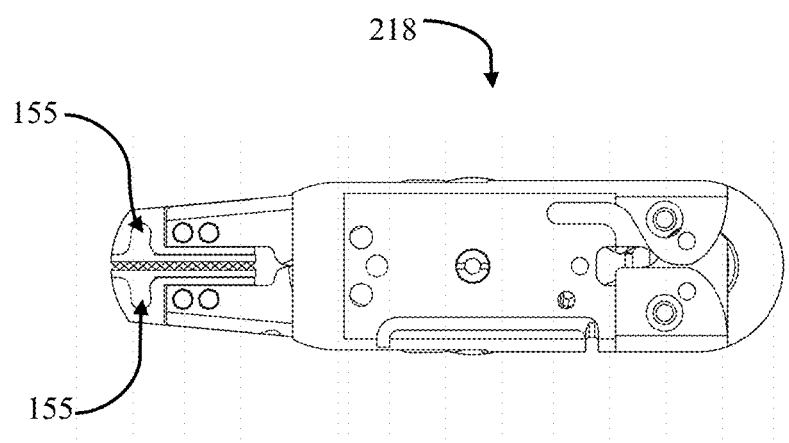

In some embodiments, the attachment pins 154 are configured to enter and mate with attachment channels 155 located on the jaws of a universal grasper 218. As depicted in the illustrative embodiment shown in FIGS. 59A-59B, in some embodiments attachment channels 155 are located on both jaws of the universal grasper 218. In some embodiments, the attachment channels 155 are located on both the left and right side of both jaws of the universal grasper 218. In one embodiment, the attachment channels 155 are located on the distal end of the jaws of the universal grasper 218, while in other embodiments the attachment channels 155 are located on the proximal end of the jaws of the universal grasper 218. The attachment channels 155 are configured to have a shape compatible to the attachment pins 154 of the lever 153 so as to allow the jaws of the universal grasper 218 to mate with the levers 153.

Figure 57A:
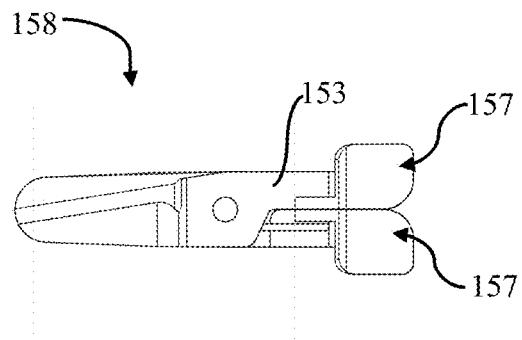
FIG. 57A is a side profile view of an embodiment of a tool with attachment appendages containing attachment pins according to one embodiment.
Figure 57B:
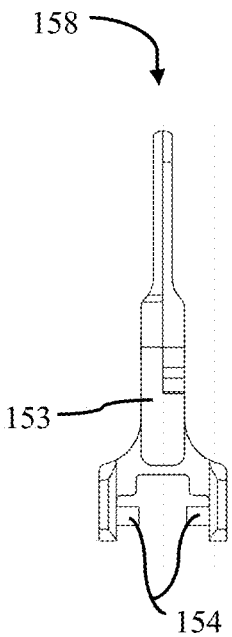
FIG. 57B is a top profile view of an embodiment of a tool with attachment appendages containing attachment pins according to one embodiment.
Figure 57C:
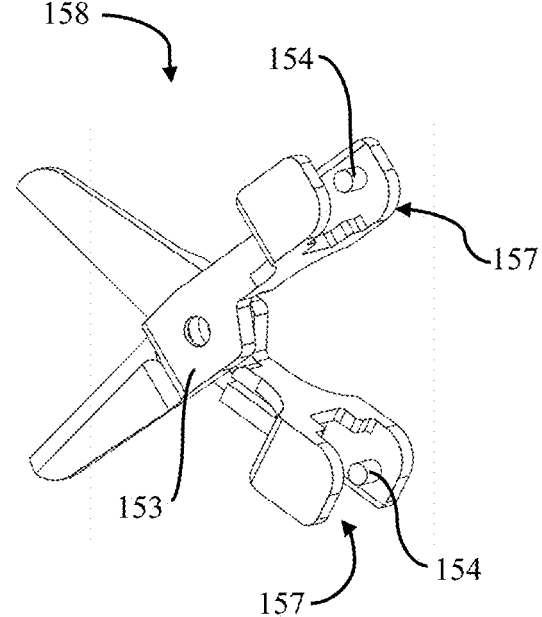
FIG. 57C is an isometric view of an embodiment of a tool with attachment appendages containing attachment pins according to one embodiment.
Figure 58A:
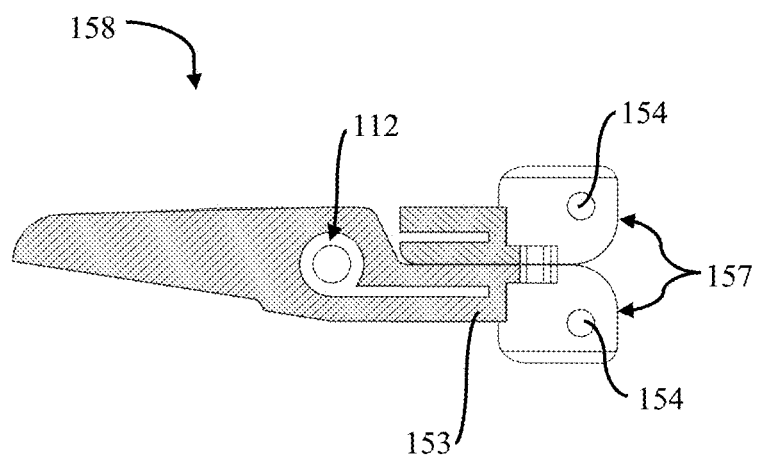
FIG. 58A is a cutaway view of a tool with attachment appendages containing attachment pins, according to one embodiment.
Figure 58B:
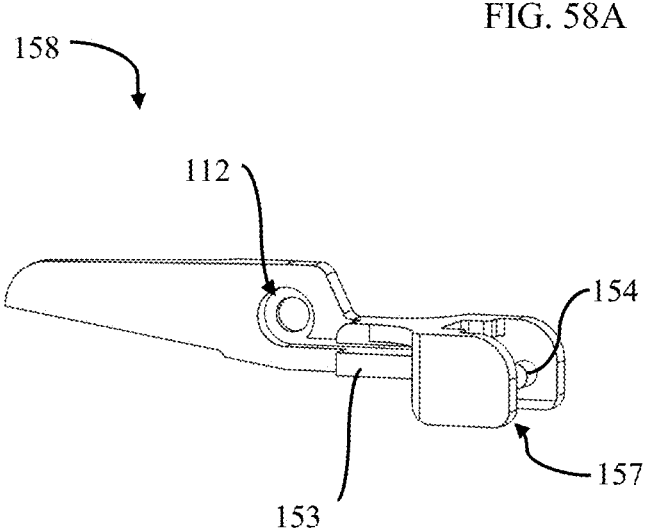
FIG. 58B is an isometric cutaway view of a tool with attachment appendages containing attachment pins, according to one embodiment.
Figure 60A:
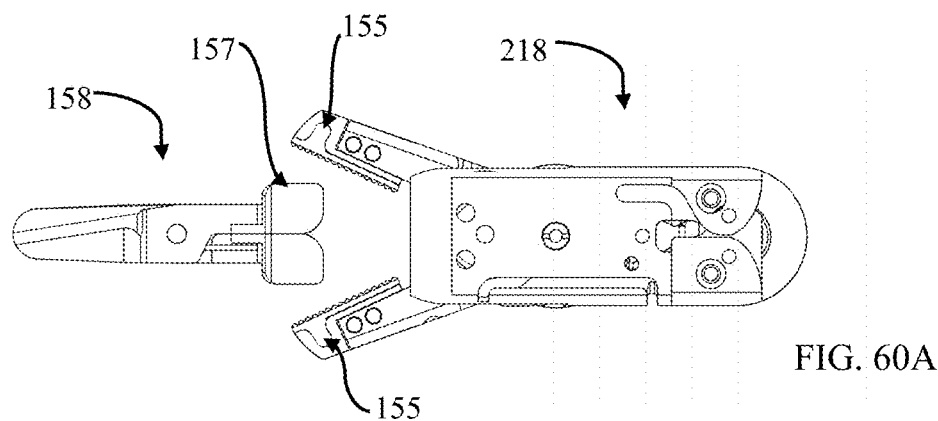
Figure 60B:
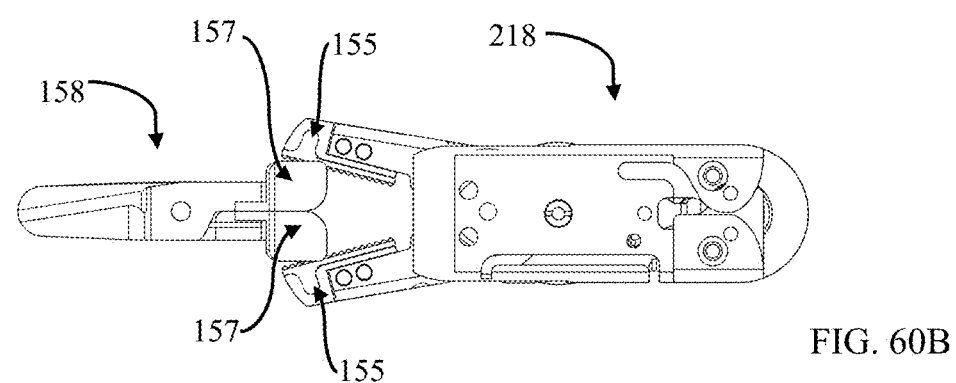
Figure 60C:
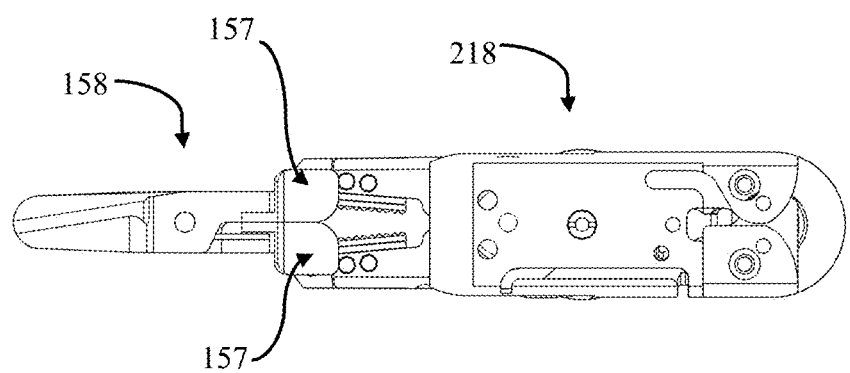
Figure 61A:
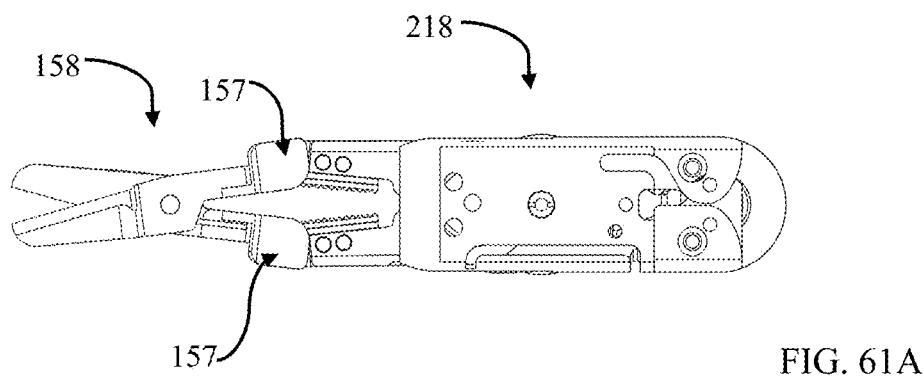
Figure 61B:
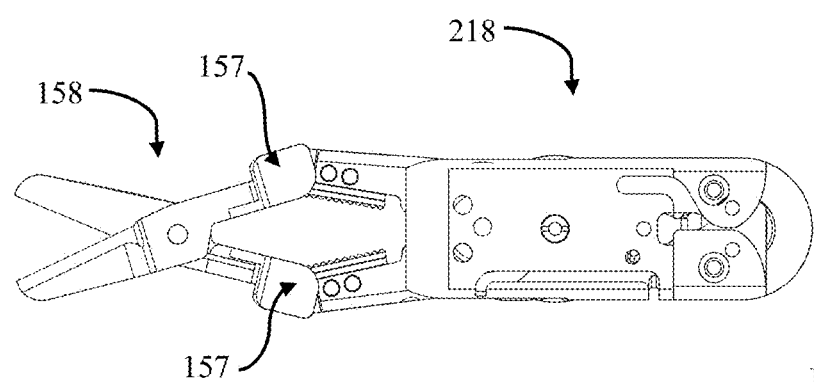
Figure 61C:
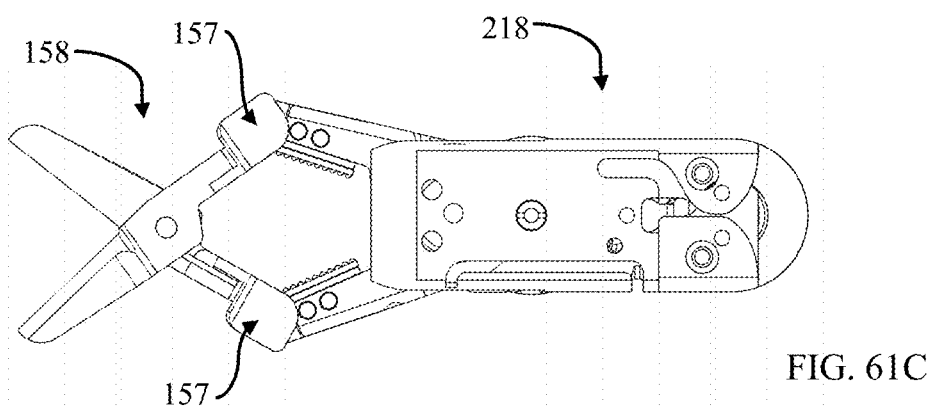

As depicted in the illustrative embodiment shown in FIGS. 57A and 57C, in some embodiments, located on the proximal end of the levers 153 are attachment appendages 157 having an inner surface. FIGS. 58A-58B, depicts a cutaway view of an illustrative embodiment of tool 158, highlighting the location of the attachment pins 154. In these embodiments, the attachment pins 154 are located on the inner surface of the attachment appendages 157. The attachment pins 154 are configured to mate with the attachment channels 155 of the universal grasper 218, forming a coupling between the universal grasper 218 and the levers 153. This mating and coupling sequence is illustrated in FIGS. 60A-60C. The attachment channels 155 are configured to be curved in shape, with the curvature of said channels configured to allow the attachment pins 154 of the levers 153 to enter the channels when the tool 158 is in a closed state, and retain the attachment pins 154 when the tool 158 is actuated. In addition, in some embodiments, located on the inner surface of levers 153 are actuation channels 112 (FIG. 58A), which are configured to house the actuator (not shown) of the tool 158. As detailed above, the actuator can be any mechanical actuation component or combination of components known in the art, such as a torsion spring, a leaf spring, a cable or other mechanical actuation component or combination of components known in the art capable of actuating a tool and/or instrument. The actuator allows the jaws of the universal grasper 218 to interact with the levers 153 of the tool 158, resulting in said tool being capable of being manipulated to multiple positions, such as from a first position to a second position, with said positions including but not limited to an open and/or closed position. The actuator is operably connected to both levers 153 of the tool 158, with said actuator siting within the actuation channels 112 of both levers 153. Additionally, the actuator is configured to apply a force upon the attachment appendages 157 of levers 153 such that attachment pins 154 of the levers 153 are retained in the attachment channels 155 of the jaws of universal grasper 218 as levers 153 and the jaws of universal grasper 218 move towards an open position. In these embodiments, as the jaws of universal grasper 218 initially move from a partially closed position towards an open position, actuator 111 applies a force upon levers 153 causing the attachment pins 154 to maintain contact with the attachment channels 155 of the jaws of universal grasper 218. As the levers 153 move towards an open position, the attachment appendages 157 and the attachment pins 154 operably connected to said appendages rotate with the levers 153, while the jaws of universal grasper 218 rotate about a separate path. The diversion between the path defined by the attachment pins 154 of levers 153 and the path of rotation of the jaws of universal grasper 218, is such that, the attachment pins 154 of levers 153 are retained in the attachment channels 155 of the jaws of universal grasper 218. This actuation sequence is shown in FIGS. 61A-61C.

Similar to the coupling detailed above, in order for the attachment pins 154 of levers 153 to mate and enter their respective attachment pin channels 155 on the jaws of universal grasper 218, the tool 158 and the levers 153 of said tool must be in a closed position, as depicted in FIG. 57A. As depicted by the sequence shown in FIGS. 60A-60C, with the levers 153 in a closed position, as the jaws of universal grasper 218 move from an open position towards a closed position, the attachment pins 154 (not shown in FIGS. 60A-60C) of levers will enter attachment channels 155 on the jaws of universal grasper 218, until said pins 154 reach the end of the channels 155, at which point the jaws of universal grasper 218 are coupled to tool 158. As shown in FIG. 60C, once the attachment pins 154 (not shown in FIG. 60C) have reached the end of their respective attachment channel 155, there is a degree of separation between the jaws of universal grasper 218, this separation ensures that said pins 154 constantly apply a force upon said channels 155 so said pins 154 are retained in their respective channel 155.

During actuation of tool 158, the jaws of universal grasper 218 transmit a force upon the attachment pins 154 of levers 153, such that said levers rotate about a fulcrum from one position to another. As tool 158 is actuated from one position to another, the actuator 111 of said tool along with the attachment pin channels 155, constrain the attachment pins 154 within said channels. In order to disengage the attachment pins 154 from the attachment pin channels 155, tool 158 and the levers 153 of said tool must be in a closed position, which results from the jaws of the universal grasper 218 applying a force upon levers 153 via the attachment pins 154. With tool 158 and levers 153 of said tool in a closed position, tool 158 is constrained in a closed position by clamping down on the distal end of said tool. In some embodiments, the introducer 126 is utilized to clamp the distal end of the tool 152 in a closed position, while in other embodiments the universal grasper of one of the robotic arm 125 is utilized or other methods detailed below are used to clamp the tool 158 in a closed position. With the tool 158 clamped in a closed position, the path of the attachment pin channels 155 is aligned with the path of rotation of the jaws of the universal grasper 218 such that as the jaws of universal grasper 218 move from a closed position towards an open position, the attachment pins 154 of the levers 153 traverse through the attachment channels 155 of the jaws of the universal grasper 218 and exit said channels, at which point the jaws of the universal grasper 218 are in a fully open state.

In some embodiments, the surgeon can elect to set a maximum opening limit of the universal grasper jaws while a tool is attached. In these embodiments, a surgeon can lock a tool in a specific orientation for an extended period of time and also limit the actuation range of motion of a tool for an extended period of time. Limiting the actuation range of motion of a tool, allows a surgeon to more precisely perform a surgical function in tight quarters, as well as allows a surgeon to elect actuation boundaries for the tool such that the surgeon is unable to move and/or actuate a tool past a desired position. Furthermore, setting maximum open limits of the universal grasper jaws allows a tool to be attached for an extended period of time until a surgeon is ready to disengage the tool. In these embodiments, maximum opening limits of the universal grasper jaws are obtained via various software commands and applications, which at a surgeon's election can be initiated and turned off.

Figure 27A:
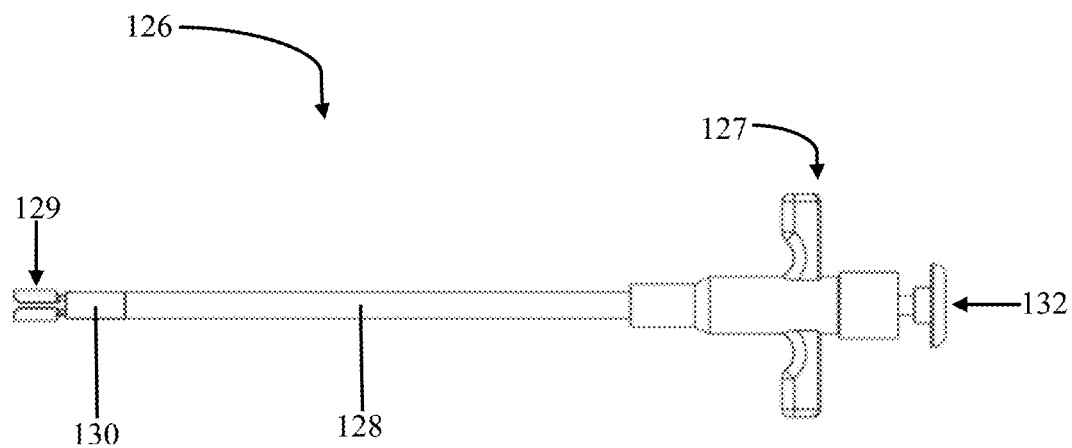
FIG. 27A is a left profile view of an introducer according to one embodiment.

In order for a surgeon to switch between different tools, he or she must first disengage the tool that is attached to a universal grasper. In one embodiment, an introducer 126 is used to disengage a tool or instrument, as well as to attach a new tool or instrument to a universal grasper. FIG. 27A depicts one embodiment of an introducer 126. In one embodiment, the introducer may be inserted and removed from a patient's body through a trocar. In some embodiments, the introducer is inserted through the same trocar and incision point as the robotic device. In other embodiments, the introducer is inserted through a separate trocar at a different incision point.

In one embodiment, the introducer contains an introducer handle 126, which is connected to the introducer shaft 128 with a tool engagement mechanism 129 located at the end of the shaft distal to the introducer handle 126 (FIG. 27A). In one embodiment, the introducer shaft 128 is a rigid shaft. In other embodiments, the introducer shaft 128 contains a flexible portion making it capable of flexing and bending, thus allowing the introducer 126 to be maneuvered to a specific position and orientation when inserted in the patient's body.

Figure 30:
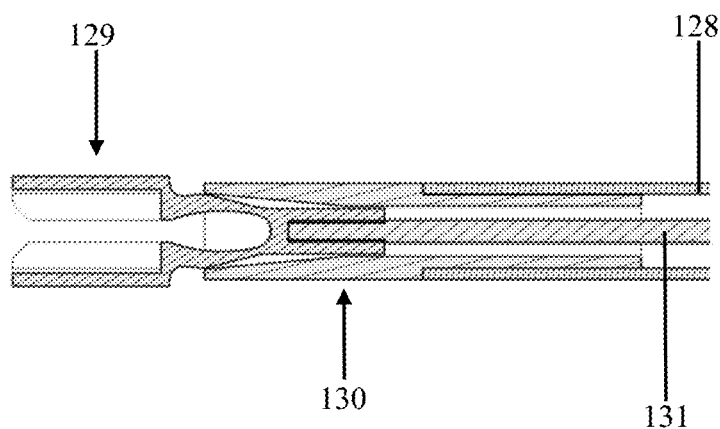
FIG. 30 is an enlarged cut away view of distal end of an introducer according to one embodiment.

In one embodiment, the tool engagement mechanism 129 is fabricated as one piece having two sides with an opening between the sides so to allow a tool to be engaged and disengaged. FIG. 30 shows one embodiment of the tool engagement mechanism 129. In other embodiments, the tool engagement mechanism 129 is fabricated as two pieces that are connected to one another via a welded connection, adhesive connection and/or any other connection known in the art. In some embodiments, the tool engagement mechanism 129 is fabricated out of biocompatible materials known in the art, including but not limited to biocompatible metals, biocompatible plastics and/or biocompatible ceramics.

In an alternative embodiment, the tool engagement mechanism 129 contains two sides that are mechanically coupled to each other so that the sides of the tool engagement mechanism 129 expand and contract in unison, creating a clamping motion. In these embodiments, no engagement tip 130 is found. In some embodiments, the sides of the tool engagement mechanism 129 are coupled to each other via linkage members, which couple to two linkage members that are coupled to the actuation rod 131, creating a four-bar linkage mechanism. In these embodiments, as the actuation rod 131 traverses distally, the sides of the tool engagement mechanism 129 spread apart creating an opening for a tool to be attached. When the actuation rod 131 traverses proximally in the introducer shaft 128 the sides of the tool engagement mechanism 129 move closer to each other creating a clamping motion, thus retaining said tool. In some embodiments, the linkage members are coupled to each other via pins. In other embodiments, the linkage members are coupled to each other via any standard attachment method known to those in the field such as a press-fit, rod and bolt, or any other existing attachment method. In some embodiments, the linkage members are replaced with pulleys and cables. In other embodiments one side of the tool engagement mechanism 129 is static with the other side of the tool engagement mechanism 129 being actuated to create a clamping motion. In further embodiments both sides of the engagement mechanism 129 move independently of each other.

Figure 28:
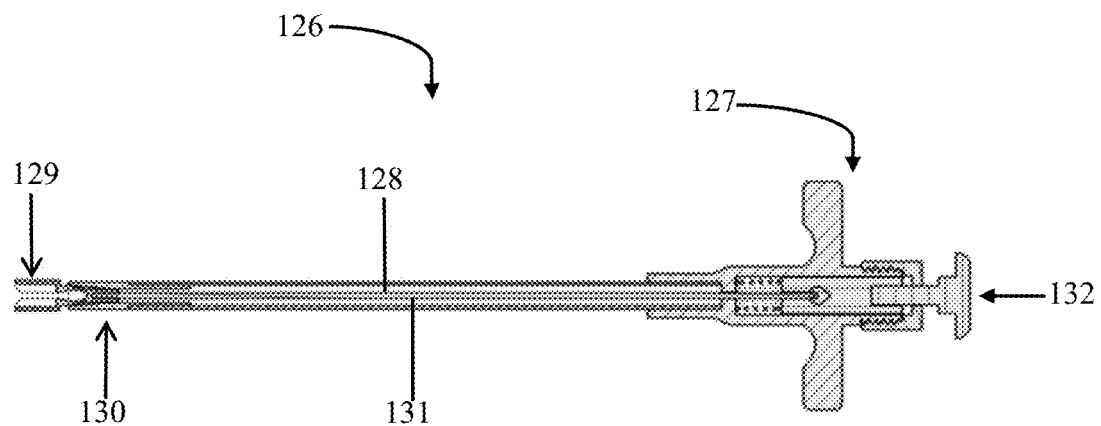
FIG. 28 is a cut away view of an introducer according to one embodiment.
Figure 29:
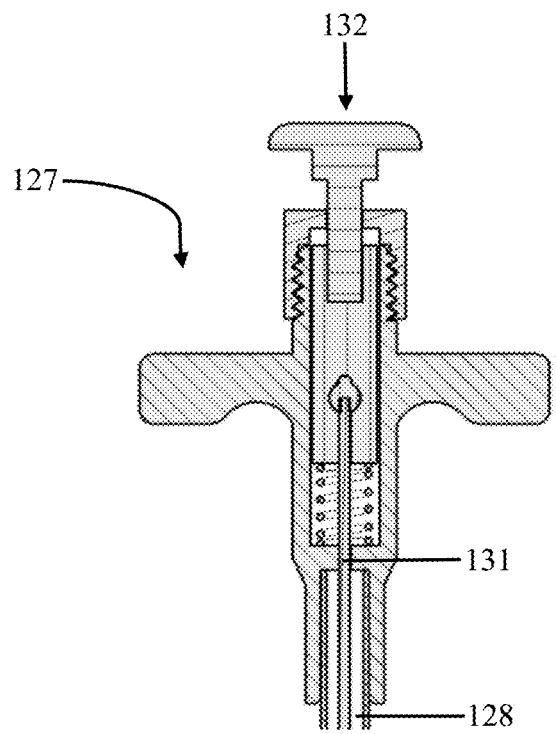
FIG. 29 is an enlarged cut away view of an introducer handle according to one embodiment.

As stated above, in one embodiment the introducer shaft 128 is rigid. In this embodiment located at the proximal end of the introducer handle 127 is an actuation button 132, which contains a spring. FIG. 29 shows a cut away view of one embodiment of the introducer handle 127 highlighting one embodiment of the actuation button 132. The spring is coupled to an actuation rod 131 that is contained inside the introducer shaft 128. As seen in FIG. 28, in some embodiments the actuation rod 131 runs from the actuation button 132 through the introducer shaft 128 to the distal end of the shaft where it couples to the tool engagement mechanism 129.

Figure 27B:
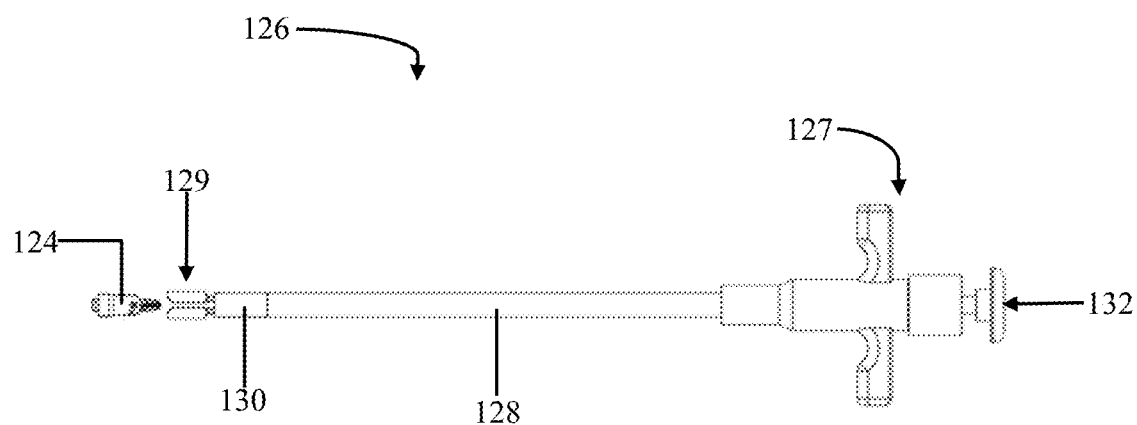
FIG. 27B is a left profile view of an introducer prior to engaging a tool according to one embodiment.
Figure 27C:
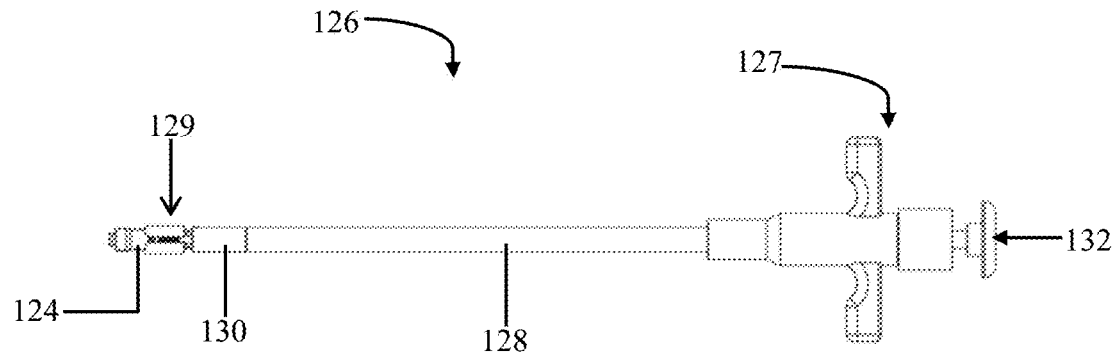
FIG. 27C is a left profile view of an introducer with a tool engaged according to one embodiment.
Figure 31:
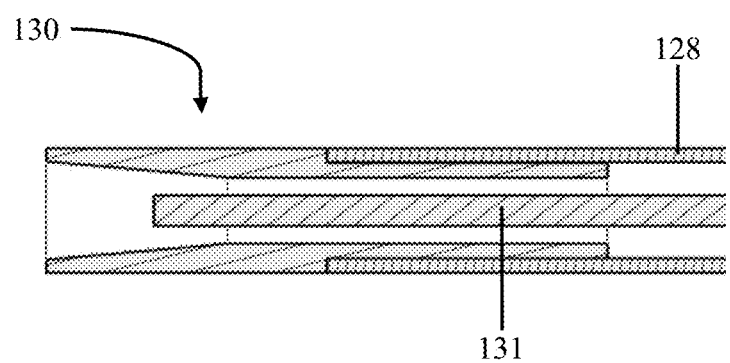
FIG. 31 is an enlarged cut away view of an engagement tip of an introducer according to one embodiment.

In some embodiments, located at the distal end of the introducer shaft 128 but proximal to the tool engagement mechanism 129 is an engagement tip 130, with the interior of the engagement tip 130 being tapered. FIG. 31 shows a cut away view of one embodiment of the engagement tip 130. When the actuation button 132 is depressed, a force is applied to the spring causing the spring to compress and exert a force on the actuation rod 131. The force exerted on the actuation rod 131 results in the actuation rod 131 traversing distally down the introducer shaft 128 causing the tool engagement mechanism 129 to extrude from the engagement tip 131, thus allowing the sides of the tool engagement mechanism 129 to separate creating a greater opening to allow a tool to engage and/or disengage from the tool engagement mechanism 129. FIG. 27B depicts one embodiment of an introducer prior to attachment to a tool. FIG. 27C depicts one embodiment of an introducer after a tool has been attached.

When the actuation button 132 is released, the spring decompresses resulting in the actuation rod 131 traversing proximally up the introducer shaft 128, which results in the proximal end of the tool engagement mechanism 129 to return inside the engagement tip 130. As the tool engagement mechanism 129 returns back inside the engagement tip 130, a force is applied on the sides of the tool engagement mechanism 129 due to the tapered interior of the engagement tip 130. The force applied on the sides of the tool engagement mechanism 129 causes the tool engagement mechanism 129 to close and clamp around a tool, thus retaining said tool. FIG. 27C depicts an embodiment of an introducer 126 after a tool has been attached.

In alternative embodiments, the introducer shaft 128 contains a flexible portion that is located distal to the introducer handle 127 but proximal to the engagement tip 130. In these embodiments, a surgeon is able to actively flex and position the distal end of the introducer shaft 128 to allow for ease of interchanging a tool. In some embodiments tension cables are routed through lumens located on the interior of the introducer shaft 128, which couple to the distal end of the flexible portion of the introducer shaft 128.

In other embodiments, tension cables are routed through lumens located on the exterior of the introducer shaft 128. In these embodiments, the tension cables are coupled to a tension mechanism that tension the tension cables causing the flexible portion of the introducer shaft 128 to flex and bend. In some embodiments, multiple tension cables are used to allow the surgeon to flex and bend the distal end of the introducer shaft 128 in numerous directions and positions. A variety of tension mechanisms can be used in different embodiments, including but not limited to pulleys, ratchets, capstans, gear trains, motors and/or other tensioning methods and combination of tensioning methods known in the field. In some embodiments, the tensioning mechanism has a locking system that allows a surgeon to keep the cables tensioned for an extended period of time. The locking system allows the surgeon to keep the introducer shaft 128 flexed in a desired position and orientation for an extended period of time.

In other embodiments only one tension cable is used to flex the distal end of the introducer shaft 128. In this embodiment, the introducer handle 127 contains a wheel, which is coupled to the introducer shaft 128 that allows the entire shaft to rotate when the surgeon rotates the wheel. This embodiment allows the surgeon to maneuver and position the tool engagement mechanism 129 to a desired orientation and location.

In some embodiments, the flexible portion of the introducer shaft 128 is constructed out of a flexible conduit. In these embodiments, the flexible conduit is fabricated out of biocompatible materials known in the art, including but not limited to biocompatible metals, biocompatible plastics, and/or biocompatible ceramics. The biocompatible materials are configured so as to allow the introducer shaft 128 to flex and bend and also return to its initial configuration.

Figure 27D:
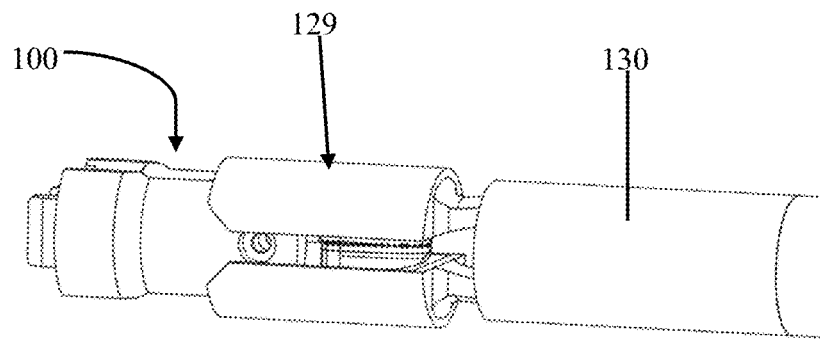
FIG. 27D is an enlarged left profile view of an introducer with a tool engaged according to one embodiment.
Figure 27E:
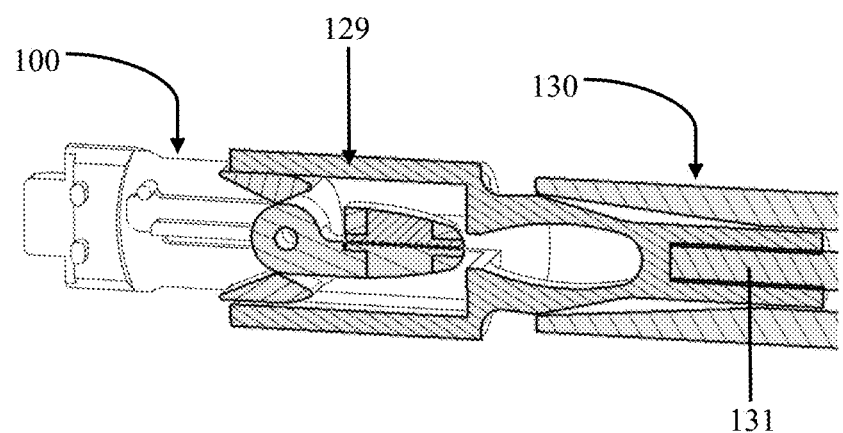
FIG. 27E is an enlarged cutaway view of an introducer with a tool engaged according to one embodiment.

In one embodiment, the tool engagement mechanism 129 is configured to fit around the distal end of a tool and clamp onto the tool hull 100 of a tool or instrument, thus rigidly affixing the tool hull 100 to the introducer 126 as depicted in the illustrative embodiment shown in FIG. 27D. FIG. 27E depicts an enlarged side cutaway view of an illustrative embodiment of a tool introducer, with the tool engagement mechanism 129 clamped around the tool hull 100 of a tool. In other embodiments, the tool engagement mechanism 129 is configured to fit around the components of a tool, clamping the tool in a closed state.

In an embodiment where a tool engagement mechanism 129 is firmly clamped on a tool hull 100, the surgeon moves the universal grasper jaws into a fully open state. As the universal grasper jaws move towards a fully open state, the TAPs 102 are released from the tool attachment pin channels 113. With the TAPs 102 no longer in the tool attachment pin channels 113, the tool hull 100 is only attached to the universal grasper 118 via the docking tabs 102. In order to remove the docking tabs 103 from the docking stations 115 the surgeon either pulls the introducer 126 away from the universal grasper 118, or maneuvers the universal grasper 118 away from the tool hull 100, thus separating the docking tabs 103 from the docking stations 115. With the tool disengaged from the universal grasper, the introducer 126 is removed from patient's body through the trocar. The surgeon is then free to remove the tool from the introducer 126, attach a new tool to the introducer 126 and insert the introducer 126 back in to the patient's body, thus allowing the universal grasper 118 to mate with the new tool. In other embodiments, the tool engagement mechanism 129 may fashion to a tool via any standard attachment method known to those in the field such as magnet connection, press-fit or any other existing attachment techniques.

In an alternative embodiment, a tool rack is inserted into the patient's body and used to store and hold tools when not in use. The tool rack is inserted into the patient through a trocar and temporarily attached to the interior body cavity of the patient by means of support. The support may be string, pins, adhesive, magnets or any other appropriate attachment means known in the field.

In a different embodiment, the tool rack may be externally supported. In one embodiment, the tool rack may contain a support shaft, which is affixed to the tool rack. The tool rack will be inserted in to the patient's body through a trocar, with the support shaft traversing through the trocar outside the patient's body where it is attached to a rigid structure. The support shaft can have a variety of shapes and sizes, which allow it to traverse through a trocar. In different embodiments, the support shaft may be substituted for a cable or wire, thus allowing it traverse through narrower spaces.

In an alternative embodiment, the tool rack may be magnetized allowing it to be externally supported via magnets situated outside of a patient's body. In this embodiment, the tool rack will be constructed of a biocompatible magnetic material, and will couple with magnets located outside of the patient's body and firmly pressed against a cavity wall, thus giving the appearance of a free-floating structure. In some embodiments, the tool rack will also contain a detachable support shaft for insertion and removal from the body.

In one embodiment, the tool rack is constructed as one row with means to hold a plurality of tools. Appropriate means may include magnets, clamps, clips or any other appropriate attachment means known in the field. In one embodiment, the tool rack contains storage slots for each individual tool. The storage slots contain a coupling mechanism that couples with a tool, allowing the tool to disengage from a universal grasper. Additionally, the coupling mechanism also allows for a universal grasper to engage a tool that is held in a storage slot. This allows a surgeon to interchange between a suite of tools with ease, as the surgeon can store and dock idle tools on the rack when not in use and engage a new tool from the rack at his or her convenience.

In a different embodiment, the tool rack is constructed as a set of rows attached to each other. The rows are collapsible to allow the rack to fit through a trocar. The rows are equipped with means to hold a plurality of tools. Appropriate means may include magnets, clamps, clips or any other appropriate attachment means known in the field. In addition, in an alternative embodiment, the rows may be equipped with storage slots containing a coupling mechanism that allows a tool to engage and disengage from the storage slot. In some embodiments, the tool rack is configured to be able to fit through the same trocar as the robotic device. In alternative embodiments, the tool rack may be inserted through a separate trocar.

Additionally, in some embodiments the tool rack may be outfitted with an irrigation system that allows for the removal of body tissue or any material that may inhibit a tool from disengaging or engaging with a universal grasper. The irrigation system would release an appropriate amount of water to remove any particles or materials at a surgeon's command. In an alternative embodiment, a brush or other tool with bristles would be attached to a tool rack, which would allow a surgeon to remove any unwanted particles or materials from the device. Other means and methods may be utilized to clean a tool or instrument, such as removing the tool from the patient's body with an introducer and manually cleaning the tool or instrument, or other known practices in the field including but not limited to, using a suction system.

In addition, in one embodiment, one of the robotic arms can be outfitted with a brush tool or other refuse removal tool or instrument. In this embodiment, the surgeon uses one robotic arm to clean the other. The surgeon maneuvers a robotic arm equipped with a brush tool or other refuse removal tool or instrument to a position and orientation that allows the surgeon to expel any materials that may interfere with the use, engagement or disengagement of a tool. Additionally, this embodiment also allows a surgeon to expel any materials or items that may be entangled or captured in the docking system of a tool rack.

Figure 50A:
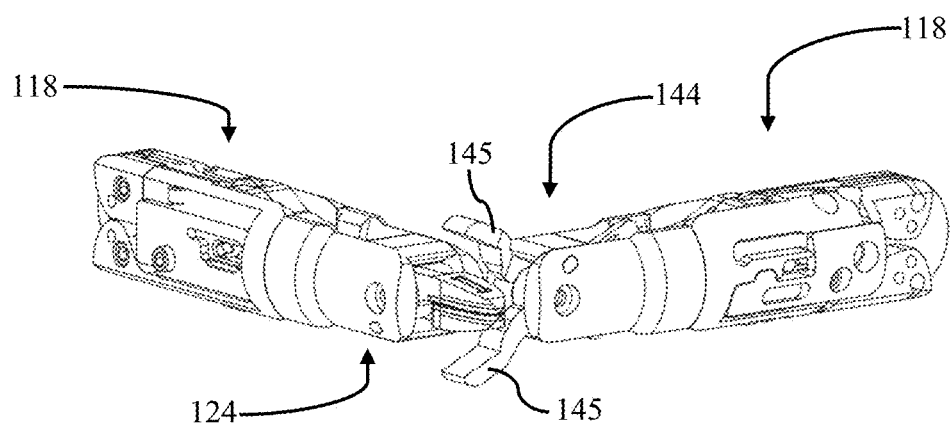
FIG. 50A is an isometric view of a disengagement tool coupled to a universal grasper prior to clamping around a tool according to one embodiment.
Figure 50B:
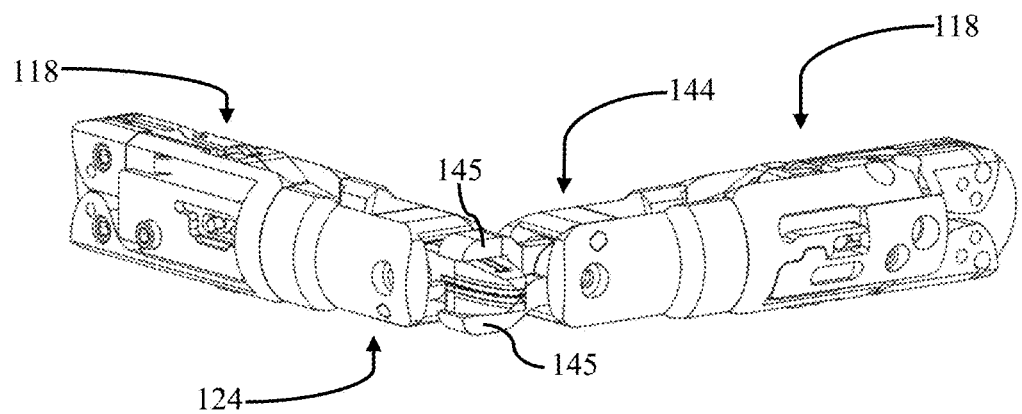
FIG. 50B is an isometric view of a disengagement tool after clamping around a tool according to one embodiment.
Figure 51A:
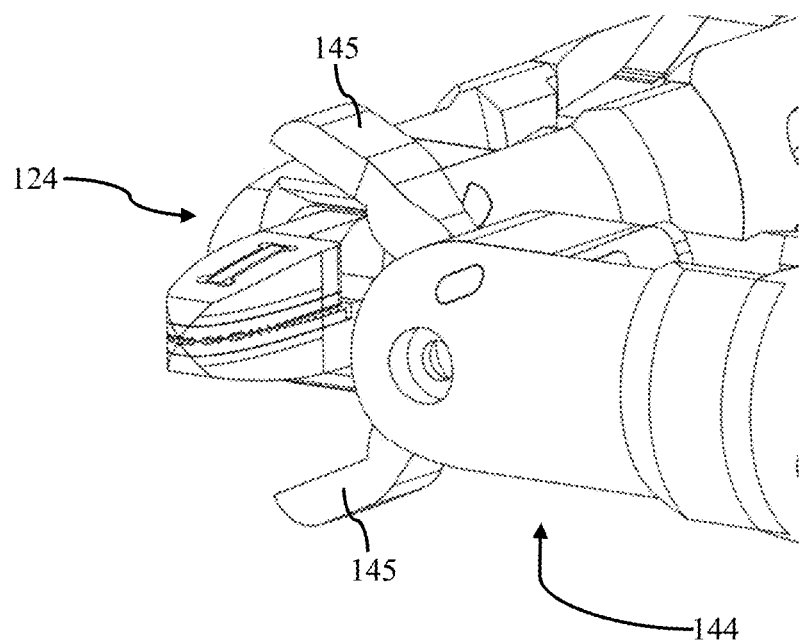
FIG. 51A is an enlarged isometric view of a disengagement tool prior to clamping around a tool according to one embodiment.
Figure 51B:
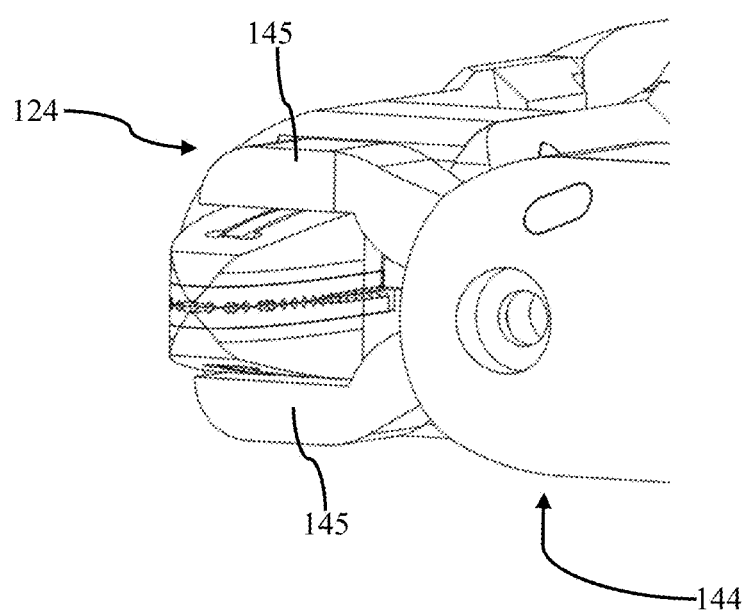
FIG. 51B is an enlarged isometric view of a disengagement tool after clamping around a tool according to one embodiment.

In other embodiments, a disengagement tool 144 is attached to a universal grasper to engage and disengage tools. FIG. 49A-FIG. 49D show multiple views of an illustrative embodiment of a disengagement tool 144. In these embodiments, a surgeon utilizes the disengagement tool 144, which operably couples to the universal grasper 118 of one of the robotic arms to disengage a tool from the other robotic arm. In these embodiments, the disengagement tool 144 couples to the universal grasper 118 utilizing the same technique detailed above for attaching a tool to the universal grasper 118. In one embodiment, the disengagement tool 144 has two clamping members 145 configured to fit around the instrument components of a tool 124. FIG. 51A depicts an illustrative embodiment of a disengagement tool 144 with the clamping members 145 in an open position prior to clamping around the instrument components of a tool 124. FIG. 51B depicts an illustrative embodiment of a disengagement tool 144 with the clamping members 145 clamped around the instrument components of a tool 124. In this embodiment, the disengagement tool 144 is fabricated as a jaw containing two clamping members 145 configured to fit around the instrument components of a tool 124, and clamp around said components in order to inhibit the components from being actuated, while simultaneously holding the tool 124 in place, thus allowing the universal grasper 118 to disengage from the tool 124. FIG. 50A depicts an illustrative embodiment of a disengagement tool 144 coupled to a universal grasper 118, with the clamping members 145 in an open state prior to clamping around the instrument components of a tool 124. FIG. 50B depicts an illustrative embodiment of a disengagement tool 144 coupled to a universal grasper 118, with the clamping members 145 clamped around the instrument components of a tool 124. In one embodiment, each of the clamping members are affixed to a tool actuation lever 109, which mate and ride along the actuation mating surfaces 114 of the jaw of the universal grasper 118, allowing the universal grasper 118 to actuate the disengagement tool in the same manner detailed above for tools containing two actuation levers 109. In some embodiments, the clamping members 145 are operably coupled to one another to allow for both clamping members 145 to move in unison. This coupling is fashioned via any standard connection method know to those in the field such as a linkage coupling, cables, welded connection, or any other existing coupling techniques known. In other embodiments, the clamping members 145 are configured to be independently movable, allowing the clamping members 145 to be orientated in different positions in order to clamp around tools with various shapes and/or sizes. In alternative embodiments, one of the clamping members 145 is rigidly fixed, with the other clamping member configured to move and clamp around the instrument components of a tool. In addition, the clamping members 145 of the disengagement tool 144 can take on a variety of shapes, and sizes in different embodiments, permitting the disengagement tool 144 to facilitate with the disengagement of tools having instrument components with various shapes and sizes. Additionally, in some embodiments the clamping members 145 are configured to clamp around the side of the instrument components of the tool 124, such as depicted in the illustrative embodiment shown in FIG. 50A and FIG. 50B. In alternative embodiments, the clamping members 145 are configured to clamp around the front of the instrument components of the tool 124.

In other embodiments, the clamping members 145 of the disengagement tool 144 are configured to fit around the tool hull 100 of a tool 124. In these embodiments, the clamping members 145 clamp around a tool hull 100 of a tool 124, constraining the tool hull 100 from moving, and thus allowing the tool 124 to be disengaged from the universal grasper 118. In addition to disengaging tools, the disengagement tool 144 can also be utilized to attach a tool 124 to a universal grasper 118 so that said tool can be utilized.

In an alternative embodiment, the jaws or jaw portions of a universal grasper are configured to disengage and/or engage a tool and/or instrument. In this embodiment, a surgeon uses the universal grasper of one robotic arm to disengage a tool attached to the universal grasper of the other robotic arm. In this embodiment, the tool is disengaged from a universal grasper utilizing the same technique detailed above. In one embodiment, the jaws of the universal grasper are configured to fit and clamp around a tool hull 100 of a tool and/or instrument, thus constraining the tool hull 100 from moving, allowing said tool to be disengaged. In another embodiment, the jaws of the universal grasper are configured to fit around and clamp the components of a tool, thus constraining the tool from being actuated, and allowing said tool to be disengaged.

Tools—Different Tools

As mentioned above, a surgeon uses a variety of different tools during an operation. In order for a surgeon to have the capacity necessary perform a vast range of different types of surgery, a multitude of tools is required. The Virtual Reality Tool System has satisfied this need by developing a suite of tools that can be utilized with the Virtual Reality Surgical Device. A suite of tools can contain a wide range of tools that a surgeon can customize and switch out based on the type of tools needed to perform a specific operation. A suite of tools can consist of static tools, actuated tools, electrified tools and/or a combination of all three. The tools can be configured in variety of sizes, thus allowing the tools to be inserted through different sized trocars.

Static tools are tools, which contain no moving components and are instead rigidly fixed to a tool hull or housing 100. An example of some static tools that could be found in a tool suite, include but are not limited to, cautery hooks, scalpels, cautery pens, surgical probes, and/or biopsy punches. Actuated tools are tools that contain moving components actuated lever(s) and actuator(s). Some examples of actuated tools that may be found in a tool suite, include but are not limited to surgical scissors, needle drivers, forceps, graspers, retractors, staplers, vessel sealers, surgical drills and/or calipers. Electrified tools are tools that contain electrical current, such as a cautery grasper, or tools that are electrically actuated such as a drill.

Figure 17A:
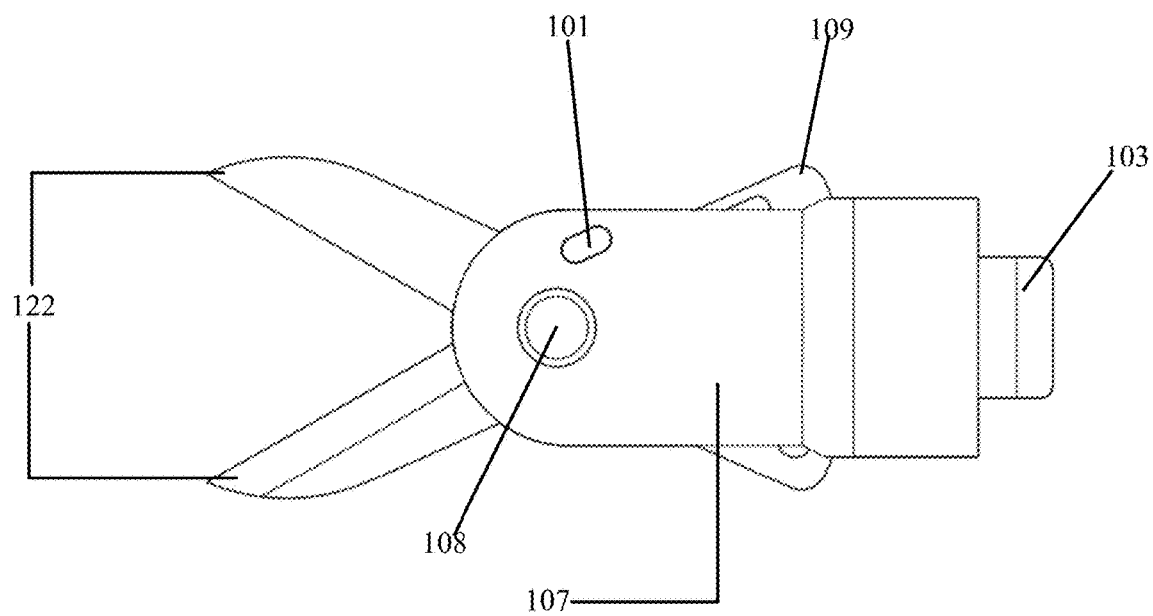
FIG. 17A is a left profile view of a scissor tool in an open position according to one embodiment.
Figure 17B:
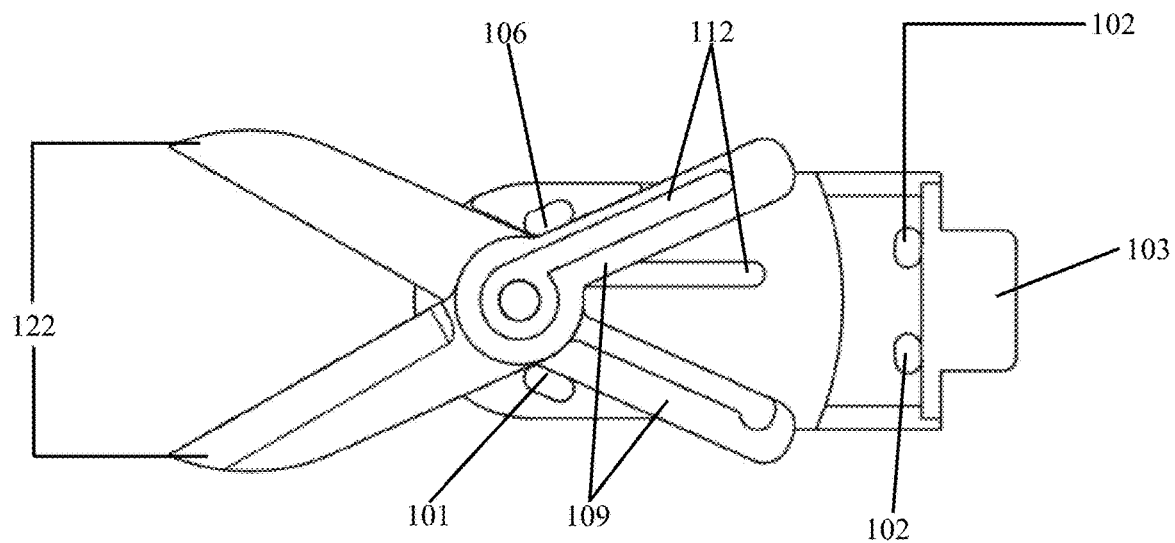
FIG. 17B is a cutaway view of the right side of a scissor tool in an open position according to one embodiment.
Figure 18A:
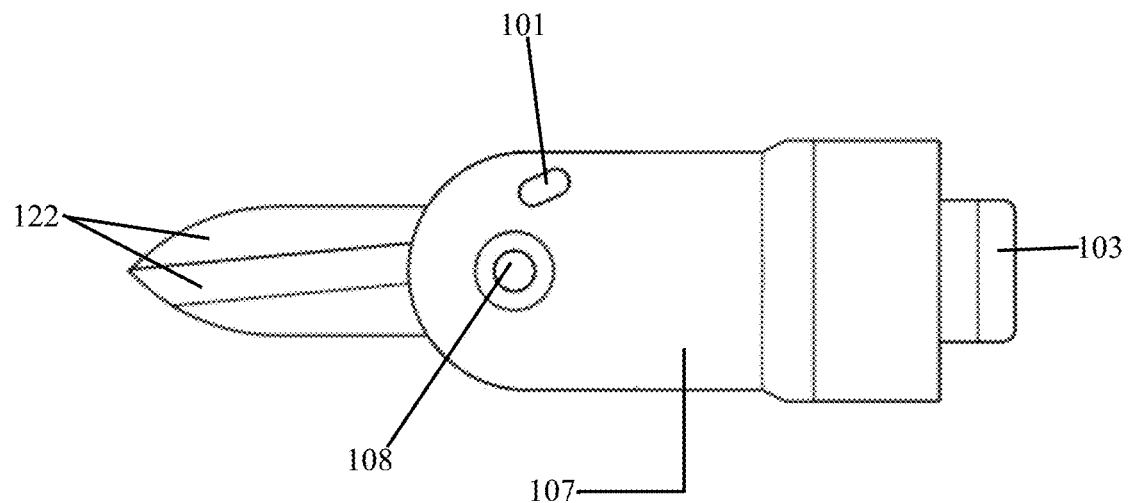
FIG. 18A is a left profile view of a scissor tool in a closed position according to one embodiment.
Figure 18B:
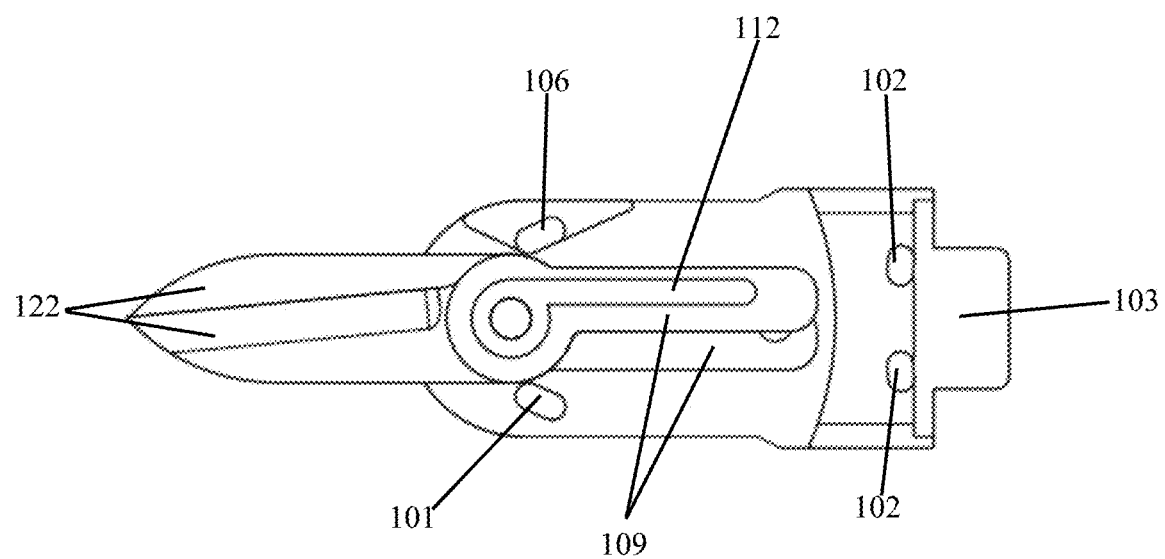
FIG. 18B is a cutaway view of the right side of a scissor tool in a closed position according to one embodiment.
Figure 19A:
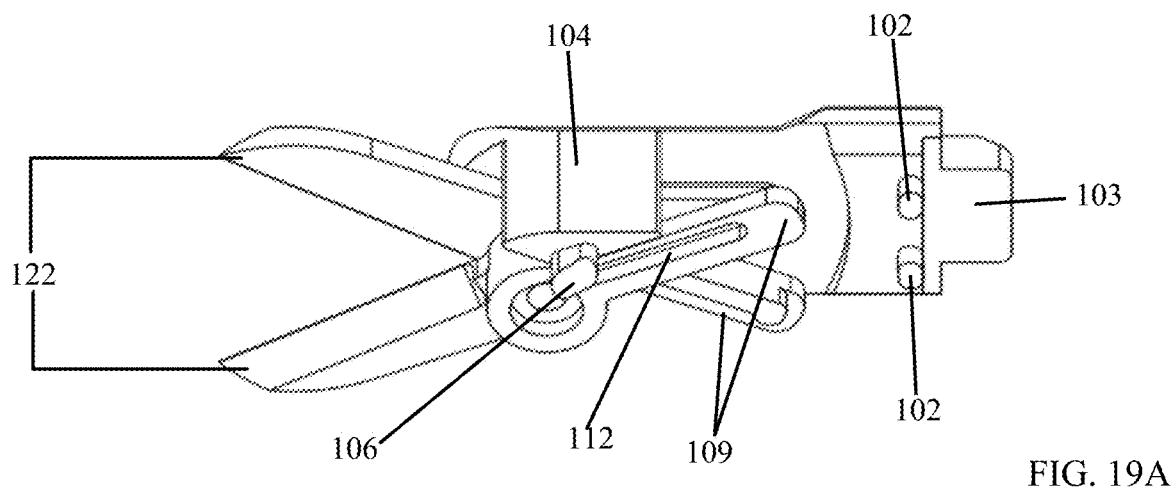
FIG. 19A is an isometric cutaway view of the right side of a scissor tool according to one embodiment.
Figure 19B:
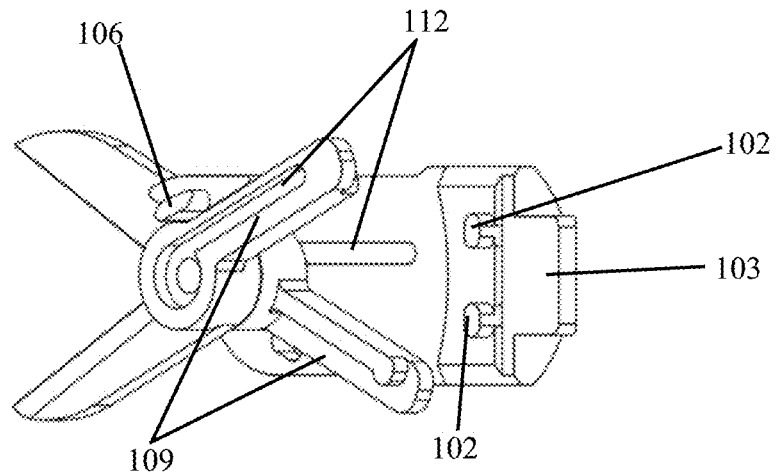
FIG. 19B is a rear side isometric cutaway view of a scissor tool according to one embodiment.
Figure 20:
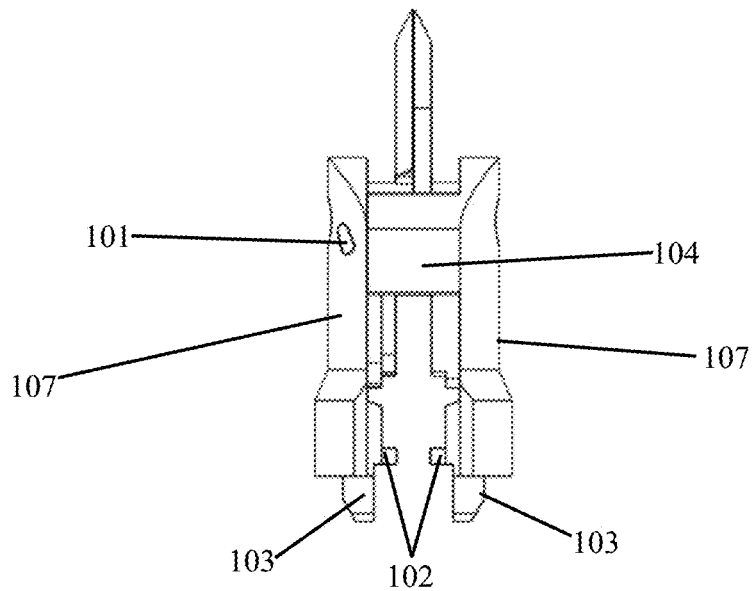
FIG. 20 is a top profile view of a scissor tool according to one embodiment.

FIG. 20 shows a top view of a scissor tool according to one embodiment. During an operation a surgeon may utilize a variety of types of scissors to perform different operation tasks, such as cutting, and/or suturing. The scissor tool contains two blades 122 as depicted in the exemplary embodiment shown in FIG. 19A. In one embodiment, each blade 122 is affixed to a tool actuation lever 109 (FIG. 19B) and is capable of being actuated. FIG. 17A and FIG. 17B show side views of one embodiment of a scissor tool with its blades 122 in an open state. FIG. 17B shows a side cutaway view of one embodiment of a scissor tool, illustrating the position of the tool actuation levers 109 when blades 122 are in an open state. FIG. 18A and FIG. 18B show side views of one embodiment of a scissor tool with its blades 122 in a closed state. FIG. 18B illustrates the position of the tool actuation levers 109 when the scissor blades 122 are in a closed state.

In one embodiment, the blades 122 can be actuated in unison and in other embodiments the blades 122 can be actuated independently of each other. In an alternative embodiment, only one blade 122 may be affixed to a tool actuation lever 109 allowing that blade 122 to be actuated and with the other blade 122 being rigidly affixed to the tool hull 100.

In one embodiment, the blades 122 are constructed with a beveled edge. The angle of the bevel may vary in embodiments, with a lower bevel angle providing the surgeon with a sharper edge for more precise incisions and a larger bevel angle providing the surgeon with a more durable edge for larger incisions. Additionally, in other embodiments a scissor tool is constructed to configure different types of surgical scissors including but not limited to iris scissors, blunt-sharp scissors, suture scissors, corneal scissors, or any other type of scissor known or used in the medical field.

Figure 22A:
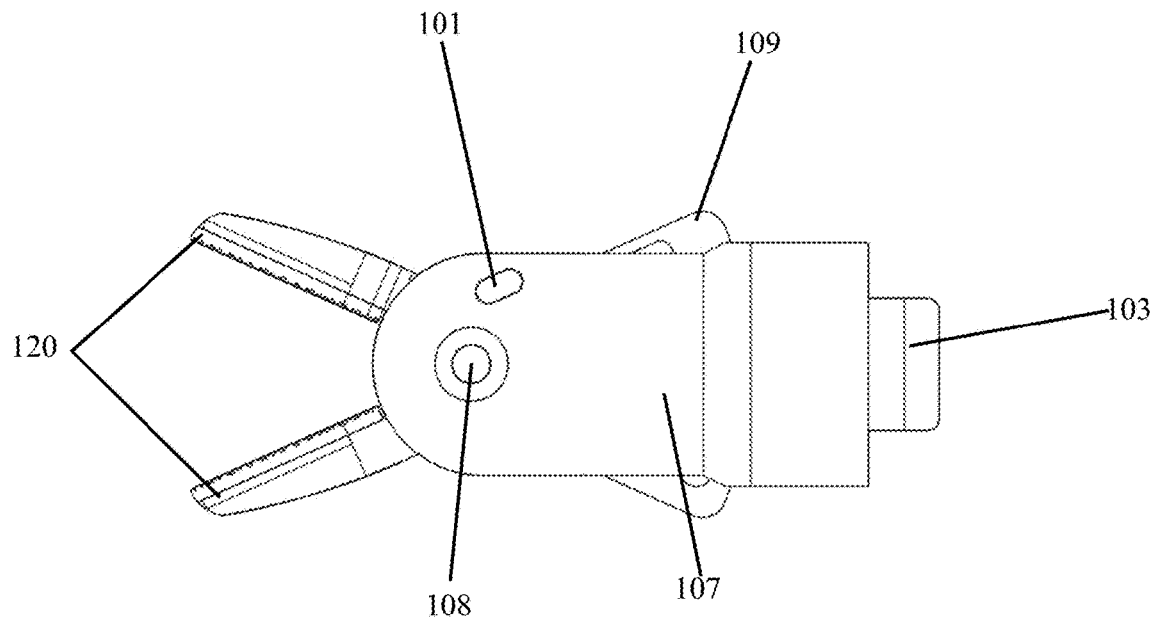
FIG. 22A is a left profile view of a needle driver tool in an open position according to one embodiment.
Figure 22B:
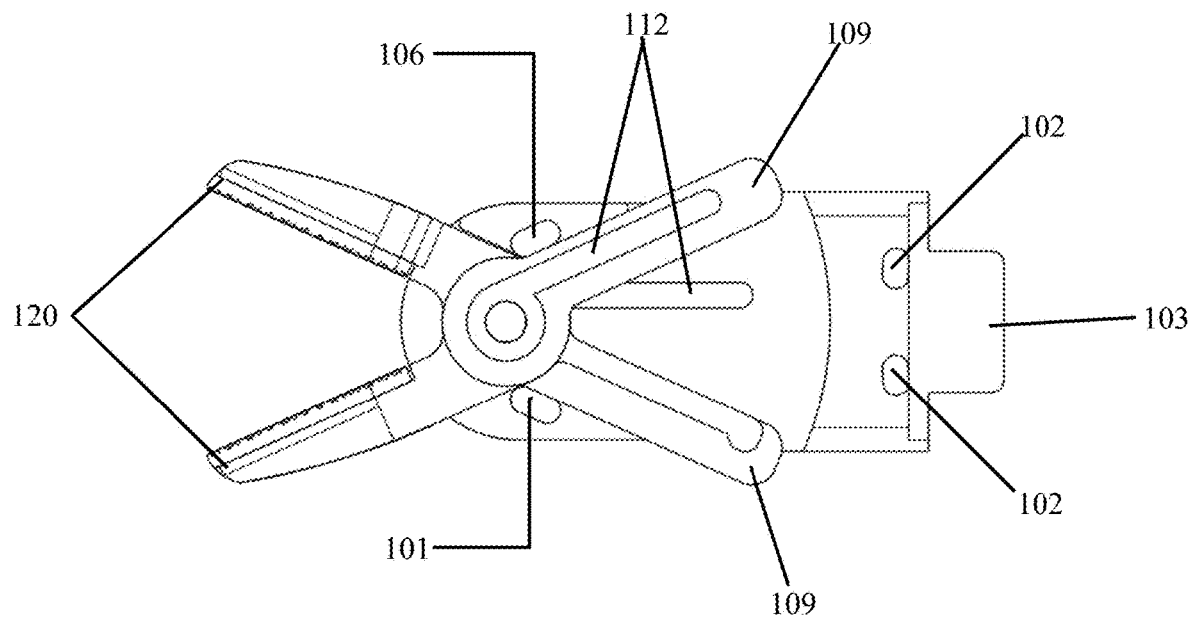
FIG. 22B is a cutaway view of the right side of a needle driver tool in an open position according to one embodiment.
Figure 23A:
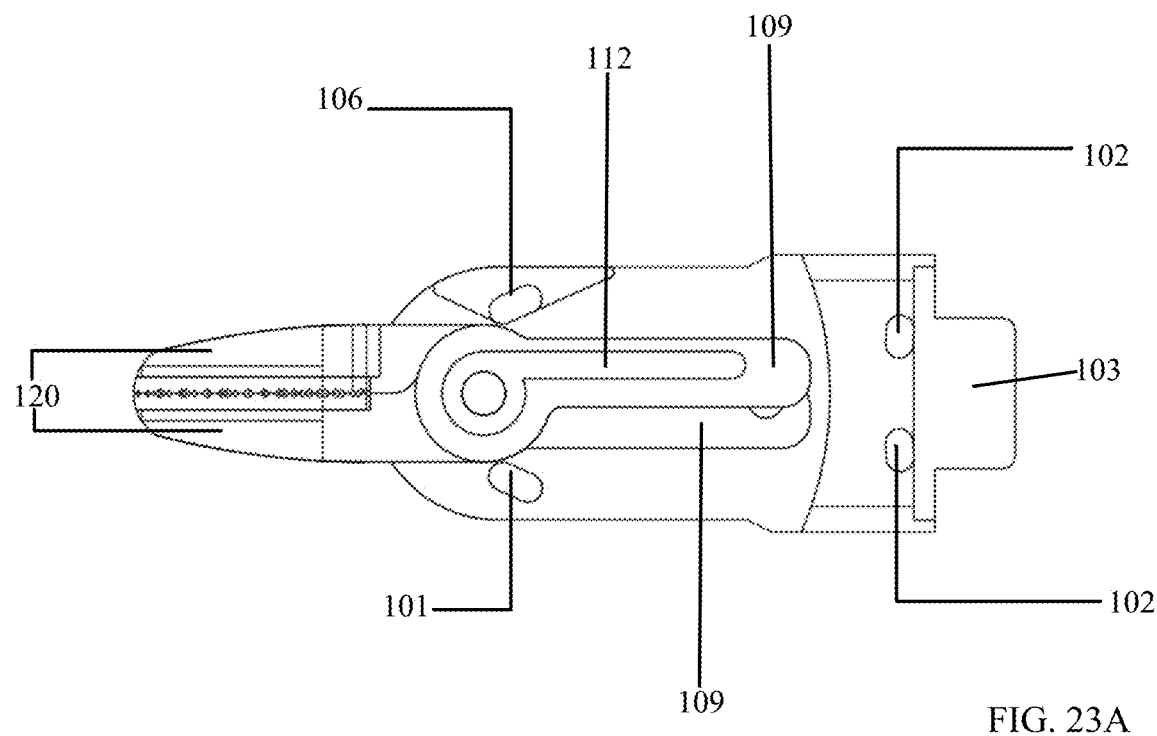
FIG. 23A is a cutaway view of a right side of a needle driver tool in a closed position according to one embodiment.
Figure 23B:
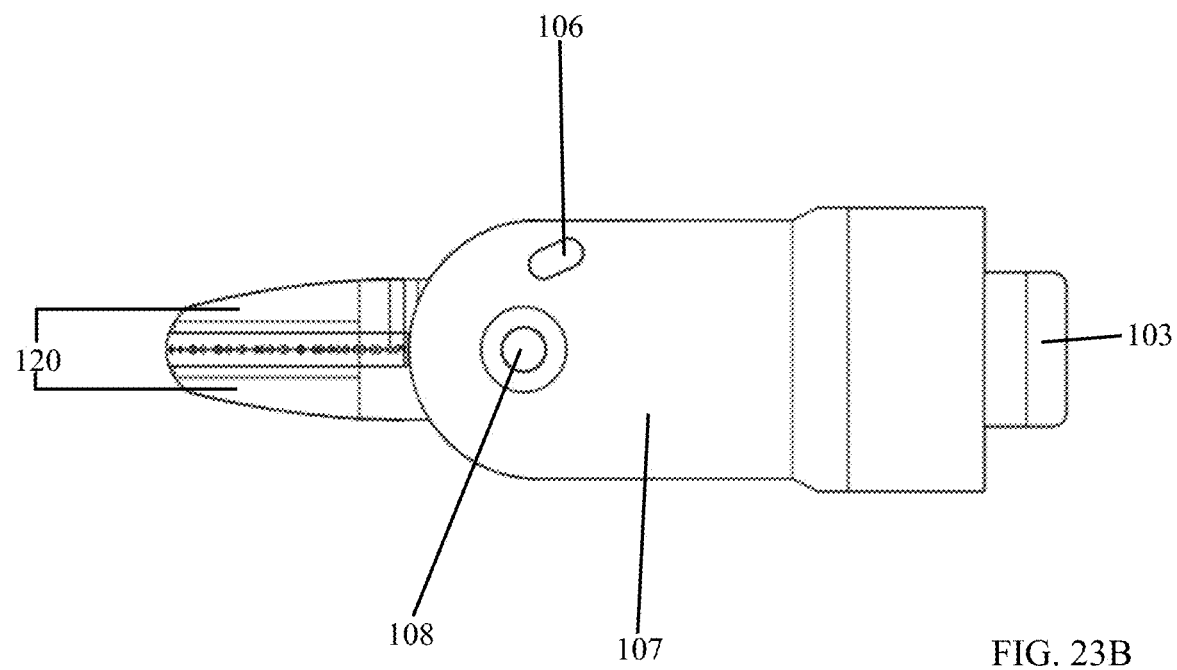
FIG. 23B is a left profile view of a needle driver tool in a closed position according to one embodiment.
Figure 24:
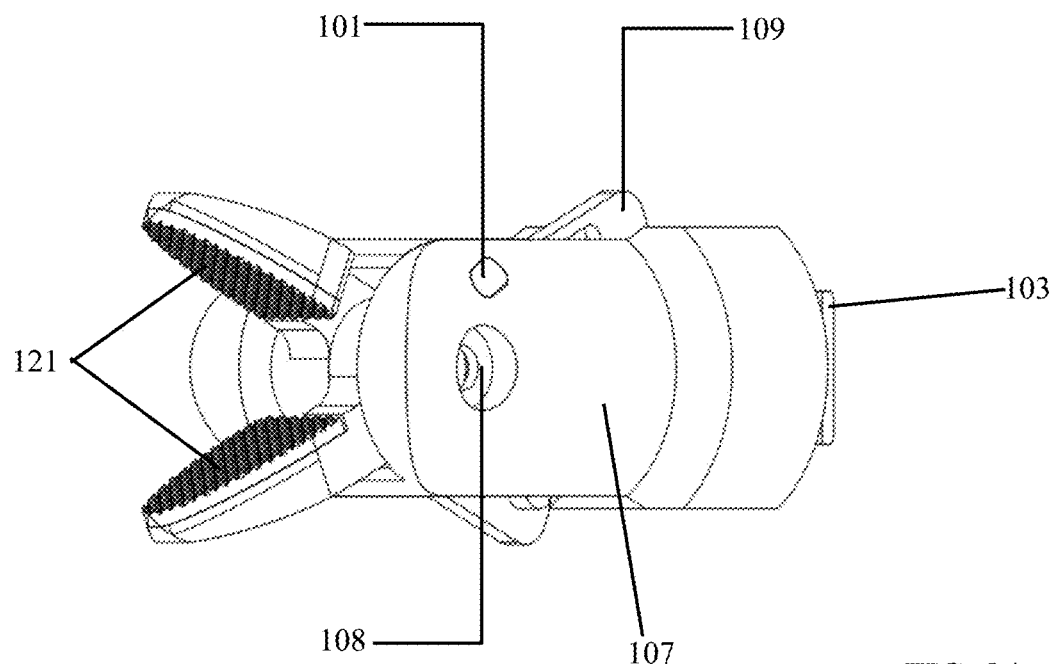
FIG. 24 is an isometric view of a needle driver tool according to one embodiment.
Figure 25:
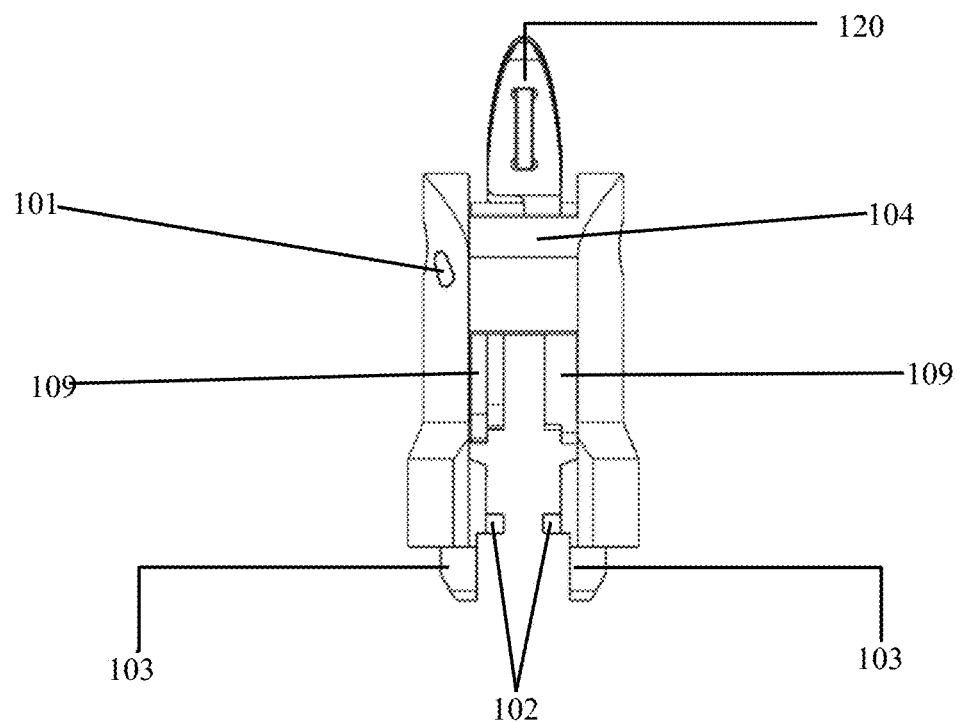
FIG. 25 is a top profile view of a needle driver tool according to one embodiment.

FIG. 24 and FIG. 25 show isometric views of a needle driver tool according to one embodiment. In one embodiment, a needle driver tool contains two needle driver-clamping jaws 120 as depicted in the exemplary embodiment shown in FIG. 22A and FIG. 22B. In some embodiments located on each engaging surface of the needle driver-clamping jaws 120 are textured surfaces 121 (FIG. 24). The textured surfaces 121 are configured to allow a surgeon to engage a tiny needle or multiple needles without the needle or needles experiencing any movement during utilization. FIG. 23A and FIG. 23B shows one embodiment of the needle driver-clamping jaws in a closed position, with FIG. 23A depicting the state of the tool actuation levers 109 when the jaws are in a closed state. Essentially, the textured surfaces 121 make it easier for a surgeon to grip and maneuver needles during an operation. In different embodiments textured surfaces 121 are configured to accommodate a variety of needle shapes and sizes. The textured surfaces 121 can take on numerous configurations such as a knurled surface, crosshatch surface or any other type of surface known to those in the field. The needle driver-clamping jaws 120 are configured in such a way to allow the textured surfaces 121 to align and couple with each other during actuation, thus allowing a needle to be grasped and constrained by the jaws.

Figure 26A:
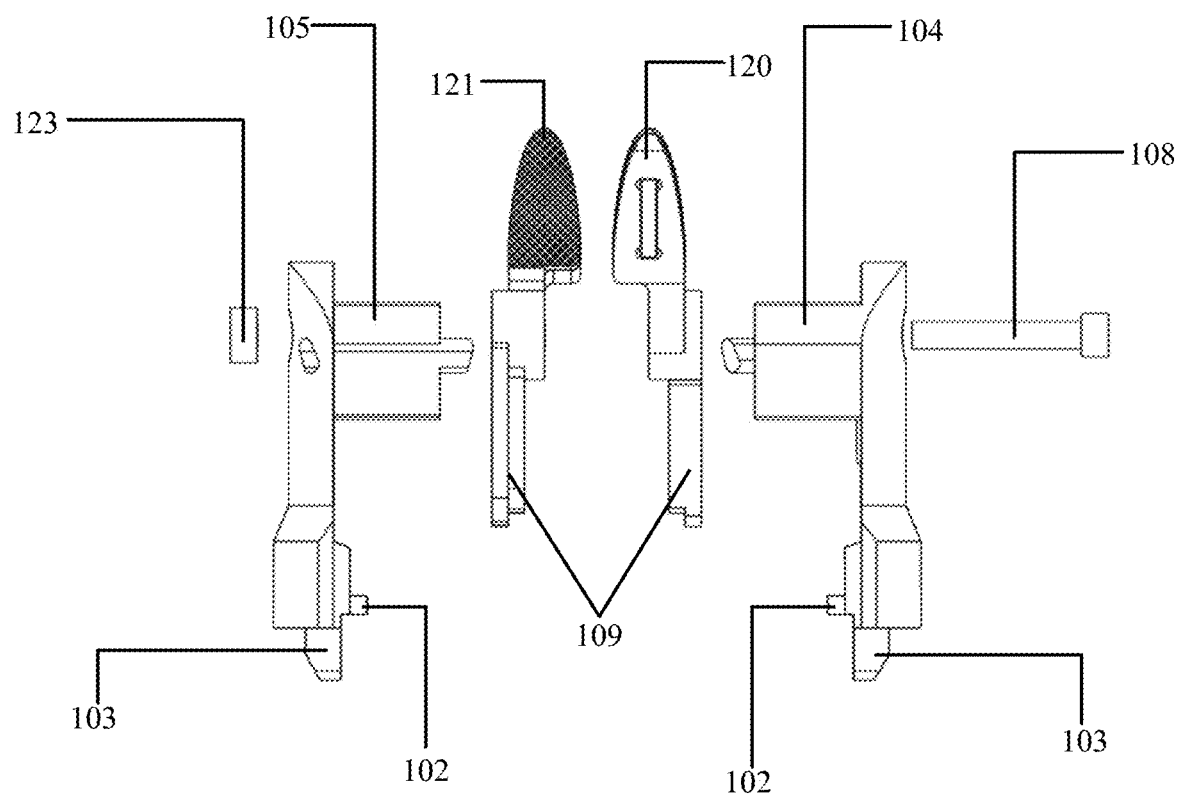
FIG. 26A is a top exploded view of a needle driver tool according to one embodiment.
Figure 26B:
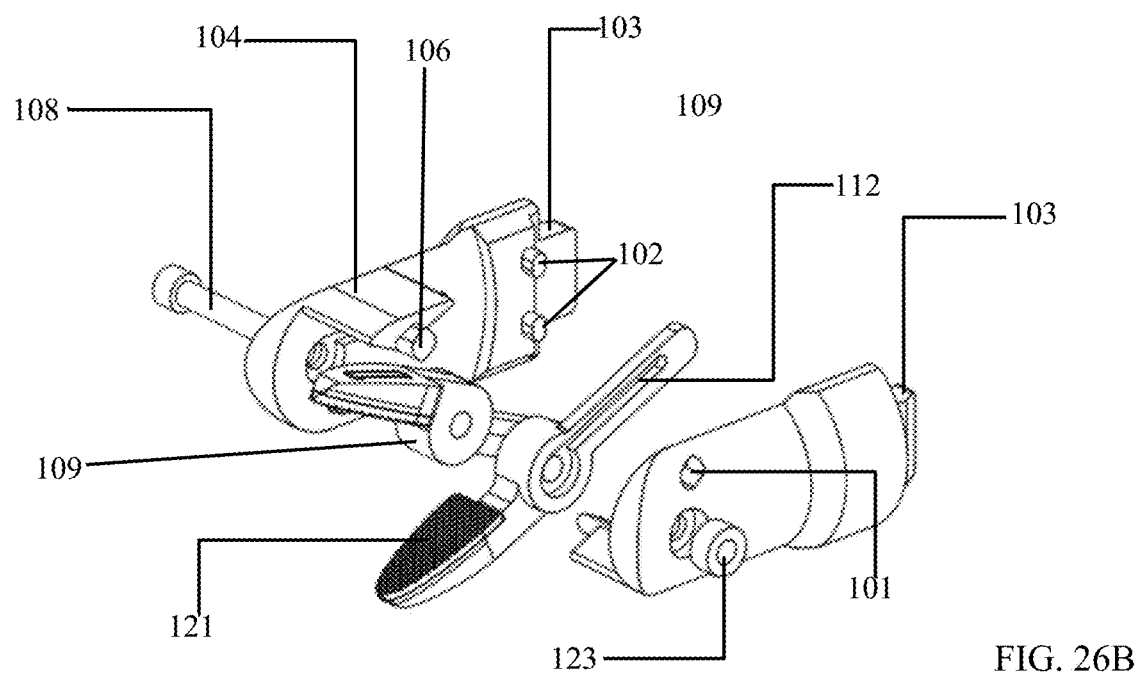
FIG. 26B is an exploded isometric view of a needle driver tool according to one embodiment.

In one embodiment, each needle driver-clamping jaw 120 is affixed to a tool actuation lever 109 as depicted in the exemplary embodiment shown in FIG. 26A and FIG. 26B. In this embodiment, each jaw can be actuated in unison. In a different embodiment, each jaw may be actuated independently of the other one. In an alternative embodiment, only one needle driver-clamping jaw 120 may be affixed to a tool actuation lever 109 allowing that jaw to be actuated, with the other jaw being rigidly affixed to a tool hull 100.

Additionally, in different embodiments tools can take on a variety of configurations, with some embodiments of tools having tool hulls, while other embodiments of tools may comprise levers with attachment appendages, as detailed above.

The invention claimed is:

1. A system comprising:
   a. a grasper comprising:
      i. a grasper housing having a distal end and a proximal end, the grasper housing defining a docking opening at the distal end, the docking opening having a shape, and
      ii. a jaw at the distal end of the grasper housing, the jaw including a first jaw portion and a second jaw portion, the first and second jaw portions being movably opposed, at least one of the first and second jaw portions comprises at least one actuation mating surface;
   b. a tool comprising:
      i. a tool housing having a distal end and a proximal end and defining an inner surface,
      ii. a docking assembly defined by the tool housing at the proximal end of the tool housing, the docking assembly comprising a first protrusion extending proximally from the proximal end of the tool housing and having a first protrusion shape complementary to the shape of the docking opening, and
      iii. an operative assembly at the distal end of the tool housing, the operative assembly comprising:
         1. a fulcrum operably coupled to the tool housing,
         2. a first lever operably connected to the fulcrum,
         3. an instrument operably coupled to the first lever, and
         4. an actuator operably coupled to the tool housing and the first lever; and
   c. a robotic device operably coupled to the proximal end of the grasper and configured to actuate the first and second jaw portions of the grasper between a first jaw position and a second jaw position.

2. The device of claim 1, wherein the first protrusion of the docking assembly of the tool is configured to cooperate with the docking opening of the grasper housing to constrain the tool in all axes relative to the grasper.

3. The device of claim 1, wherein the first lever comprises a proximal end configured to ride along the at least one actuation mating surface of one of the first or second jaw portions of the grasper.

4. The device of claim 1, wherein, when the tool is coupled to the grasper, at least one of the first and second jaw portions of the grasper is configured to apply a force on the first lever to rotate the first lever about the fulcrum from a first lever position to a second lever position.

5. The device of claim 4, wherein the actuator is configured to retain an energy from the force applied by the at least one of the first and second jaw portions.

6. The device of claim 5, wherein the actuator is configured to release the energy retained by said actuator as a force upon the at least one lever to rotate the at least one lever about the fulcrum from the second lever position to the first lever position.

7. The device of claim 1, wherein the actuator is configured to apply a force upon the first lever to bias the first lever in a first direction.

8. The device of claim 1, wherein the first jaw portion is fixed relative to the grasper housing and the second jaw portion is movable relative to the first jaw portion.

9. The device of claim 1, wherein the tool housing comprises a plurality of tool housing segments, wherein the plurality of tool housing segments define a tool housing interior, and wherein the plurality of tool housing segments are coupled by at least one support.

10. The device of claim 9, wherein the actuator operably coupled to the tool housing is operably coupled to the interior of one of the plurality of tool housing segments.

11. The device of claim 1, wherein at least one of the first and second jaw portions defines a channel having a channel shape and the docking assembly further comprises a second protrusion extending from the inner surface of the tool housing that has a second protrusion shape complementary to the channel shape.

12. The device of claim 11, wherein the first protrusion of the docking assembly is configured to cooperate with the docking opening of the grasper housing and the second protrusion of the docking assembly is configured to cooperate with the channel of the at least one of the first and second jaw portions of the grasper to constrain the tool in all axes relative to the grasper.

13. The device of claim 1, wherein the first and second jaw portions are independently movable.

14. The device of claim 1, wherein the first jaw portion comprises:
   a. an electrically conductive contact portion at a distal end of the jaw portion, and
   b. an electrical conductor coupled to the conductive contact portion;
   c. wherein the first jaw portion is electrically insulated.

15. The device of claim 1, wherein the first and second jaw portions are electrically conductive and the first jaw portion is coupled to a first electrical conductor and the second jaw portion is coupled to a second electrical conductor, wherein the system further comprises a power supply coupled to the first and second electrical conductors for supplying electrical power to the first and second jaw portions and wherein the first and second jaw portions are electrically insulated.

16. The device of claim 1, the operative assembly of the tool further comprising a second lever operably coupled to the fulcrum, a second instrument operably coupled to the second lever, and wherein the first and second levers each comprise a proximal end and the first and second jaw portions of the grasper each comprise at least one actuation mating surface.

17. The device of claim 16, wherein the proximal end of the first lever is configured to ride along the at least one actuation mating surface of the first jaw portion and the proximal end of the second lever is configured to ride along the at least one actuation mating surface of the second jaw portion.

18. The device of claim 16, wherein the first and second levers are configured to move independently of one another.

19. The device of claim 16, the operative assembly of the tool further comprising a second actuator operably coupled to the tool housing and the second lever.

20. The device of claim 1, wherein the instrument of the operative assembly is one of surgical scissors, needle driver, forceps, grasper, retractor, surgical stapler, vessel sealer, surgical drill, cautery pen, cautery hook or caliper.

21. The device of claim 1, wherein the instrument comprises a first component and a second component, wherein the first component is operably coupled to the first lever and the second component is operably coupled to a second lever.

22. The device of claim 1, wherein the first jaw portion of the grasper further comprises a force-open channel having a force-open channel shape and wherein the first lever of the tool further comprises a proximal end comprising a projection having a projection shape complementary to the force-open channel.

23. The device of claim 22, wherein, when the tool couples to the grasper, the projection of the first lever is configured to cooperate with the force-open channel of the first jaw portion of the grasper to allow the projection to pass through the force-open channel and maintain a clearance over the first jaw portion.

24. The device of claim 23, wherein, the first jaw portion of the grasper is configured to apply a force upon the projection of the first lever as the first jaw portion moves from the second jaw position to the first jaw position to rotate the first lever about the fulcrum from a second lever position to a first lever position.

25. The device of claim 1, wherein the first jaw portion of the grasper further comprises a first force-open channel having a first force-open channel shape and the first lever of the operative assembly of the tool further comprises a proximal end with a first projection having a first projection shape complementary to the first force-open channel of the first jaw portion and wherein the second jaw portion of the grasper further comprises a second force-open channel having a second force-open channel shape and the operative assembly of the tool further comprises a second lever having a second instrument and a proximal end having a second projection having a second projection shape complimentary to the second force-open channel of the second jaw portion.

26. The device of claim 1, wherein the grasper housing further defines a plurality of docking openings, each of the plurality of docking opening having a shape, and wherein the docking assembly of the tool further comprises a plurality of first protrusions extending proximally from the proximal end of the tool housing and each of the plurality of first protrusions having a corresponding shape complementary to the shape of one of the plurality of docking openings, and wherein the plurality of first protrusions of the docking assembly of the tool are configured to cooperate with the plurality of docking openings of the grasper housing to constrain the tool in all axes relative to the grasper.

27. The device of claim 1, wherein the first jaw portion defines a plurality of channels, each of the plurality of channels having a channel shape and the second jaw portion defines a plurality of channels, each of the plurality of channels having a channel shape, and wherein the docking assembly of the tool further comprises a plurality of second protrusions extending from the inner surface of the tool housing, each of the plurality of second protrusions having a corresponding second protrusion shape complementary to the channel shape of the plurality of channels of the first jaw portion and the channel shape of the plurality of channels of the second jaw portion.

28. The device of claim 1, wherein the first protrusion of the docking assembly of the tool comprises a first magnetic contact having a first magnetic contact shape and the docking opening of the grasper housing comprises a second magnetic contact having a second magnetic contact shape complementary to the first magnetic contact of the first protrusion, wherein the first magnetic contact of the first protrusion of the docking assembly of the tool is configured to cooperate with the second magnetic contact of the docking opening of the grasper to constrain the tool in all axes relative to the grasper.

* * * * *